United States Patent
Cheng et al.

(10) Patent No.: US 11,149,062 B2
(45) Date of Patent: Oct. 19, 2021

(54) HDAC INHIBITORS AND METHODS OF TREATMENT USING THE SAME

(71) Applicant: UWM Research Foundation, Inc., Milwaukee, WI (US)

(72) Inventors: Yi-Qiang Cheng, Trophy Club, TX (US); M. Mahmun Hossain, Franklin, WI (US); Douglas Steeber, Cedarburg, WI (US); Karyn Frick, Bayside, WI (US); Steven Clark, Shorewood, WI (US); Joseph Ulicki, Menomonee Falls, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 313 days.

(21) Appl. No.: 15/755,701

(22) PCT Filed: Oct. 29, 2015

(86) PCT No.: PCT/US2015/058167
§ 371 (c)(1),
(2) Date: Feb. 27, 2018

(87) PCT Pub. No.: WO2017/039726
PCT Pub. Date: Mar. 9, 2017

(65) Prior Publication Data
US 2018/0258135 A1    Sep. 13, 2018

Related U.S. Application Data

(60) Provisional application No. 62/211,304, filed on Aug. 28, 2015.

(51) Int. Cl.
| | |
|---|---|
| C07K 5/062 | (2006.01) |
| C07C 323/52 | (2006.01) |
| A61K 38/00 | (2006.01) |

(52) U.S. Cl.
CPC .......... *C07K 5/0606* (2013.01); *C07C 323/52* (2013.01); *A61K 38/00* (2013.01)

(58) Field of Classification Search
None
See application file for complete search history.

(56) References Cited

U.S. PATENT DOCUMENTS

| | | |
|---|---|---|
| 8,148,102 B2 | 4/2012 | Cheng |
| 8,217,076 B2 | 7/2012 | Williams et al. |
| 2006/0018921 A1 | 1/2006 | Levenson et al. |
| 2006/0128660 A1 | 6/2006 | Rajski et al. |
| 2009/0131390 A1 | 5/2009 | Ganesan et al. |
| 2010/0261878 A1 | 10/2010 | Cheng |
| 2011/0053856 A1 | 3/2011 | Or et al. |
| 2012/0039909 A1 | 2/2012 | Tsai et al. |
| 2012/0101147 A1 | 4/2012 | Tsai et al. |
| 2014/0051680 A1 | 2/2014 | Jacques et al. |

FOREIGN PATENT DOCUMENTS

| | | |
|---|---|---|
| CN | 104529842 | * 4/2015 |
| WO | WO 2008/062201 | 5/2008 |

OTHER PUBLICATIONS

CN 104529842 machine translation accessed from patents.google.com on Feb. 12, 2020 (Year: 2015).*
Halsall "Histone deacetylase inhibitors for cancer therapy: An evolutionarily ancient resistance response may explain their limited success" Bioessays 38: 1102-1110 (Year: 2016).*
Rana "Understanding Failure and Improving Treatment Using HDAC Inhibitors for Prostate Cancer" Biomedicines 2020, 8, 22 (Year: 2020).*
Didonna "The promise and perils of HDAC inhibitors in neurodegeneration" Annals of Clinical and Translational Neurology 2015; 2(1): 79-101 (Year: 2015).*
Gowda "Selenium-containing histone deacetylase inhibitors for melanoma management" Cancer Biology & Therapy 13:9, 756-765 (Year: 2012).*
Stanford "Alzheimer's Prevention, Treatment and Research—A Q&A with Dr. Frank Longo" accessed from stanfordhealthcare.org (Year: 2016).*
Albert Bowers, et. al, "The Total Synthesis and Biological Mode of Action of Largazole: A Potent Class I Histone Deacetylase (HDAC) Inhibitor", J Am Chem Soc., 130(33): 11219-11222 (2008).
Andrews, K. T.; et al., HDAC inhibitors in parasitic diseases. Immunol. Cell Biol. 2012, 90, 66-77.
Bernstein, B. E., et al., "The mammalian epigenome," Cell 2007, 128, 669-681.
Bertrand, P., "Inside HDAC with HDAC inhibitors," European Journal of Medicinal Chemistry. 2010, 45, 2095-2116.
Beurel, E. "HDAC6 regulates LPS-tolerance in astrocytes," PLoS One 2011, 6, e25804.
Bolden, J. E.; et al., "Anticancer activities of histone deacetylase inhibitors," Nature Rev. Drug Discovery 2006, 5, 769-784.
Bots, M.; et al., "Rational Combinations Using HDAC Inhibitors," Clinical Cancer Res 2009, 15, 3970.
Butler, L. M.; et al., "Suberoylanilide Hydroxamic Acid, an Inhibitor of Histone Deacetylase, Suppresses the Growth of Prostate Cancer Cells in Vitro and in Vivo," Cancer Research 2000, 60, 5165-170.
Chen, Y., et al., (2003),"Total synthesis of the depsipeptide FR-901375," J Org Chem 68, 8902-8905.
Cheng, Y. Q.; et al.; "Characterization of a Gene Cluster Responsible for the Biosynthesis of Anticancer Agent FK228 in *Chromobacterium violaceum* No. 968," Appl Environ Microbiol 2007, 73, 3460.
Chuang, D. M.; et al., "Multiple roles of HDAC inhibition in neurodegenerative conditions," Trends Neurosci. 2009, 32, 591-601.

(Continued)

*Primary Examiner* — Adam Weidner
(74) *Attorney, Agent, or Firm* — Michael Best & Friedrich LLP

(57) ABSTRACT

Disclosed herein are novel HDAC inhibitors. The HDAC inhibitors may be used in methods of treating cancer. The HDAC inhibitors may be used in methods of treating a neurological disorder.

16 Claims, 15 Drawing Sheets

(56) References Cited

OTHER PUBLICATIONS

Cole, K. E.; et al., "Structural Basis of the Antiproliferative Activity of Largazole, a Depsipeptide Inhibitor of the Histone Deacetylases," J Am Chem Soc 2011, 133, 12474.
De Ruijter, A. J.; et al., "Histone deacetylases (HDACs): Characterization of the classical HDAC family," Biochem. J. 2003, 370, 737-749.
Dokmanovic, M.; Clarke, et al., "Histone deacetylase inhibitors: Overview and perspectives," Mol. Cancer Res. 2007, 5, 981-989.
Emanuele, S.; et al., "Histone deacetylase inhibitors: Apoptotic effects and clinical implications," International Journal of Oncology, 2008, 33, 637-646.
Fass, D. M., et al., "Histone Acetylation and Deacetylation. In Epigenetic Regulation and Epigenomics: Advances in Molecular Biology and Medicine," (Wiley-VCH Vrlag & Co. KGaA: Weinheim, 2012; pp. 515-561.
FDA, "Oncology Drug Product Approvals in 2009," J Natl Cancer Inst 2010, 102, 219.
Finnin, M. S., et al., "Structures of a histone deacetylase homologue bound to the TSA and SAHA inhibitors," Nature 1999, 401, 188-193.
Gal-Yam, E. N.; et al., "Cancer Epigenetics: Modifications, Screening, and Therapy," Annual review of medicine 2008, 59, 267.
Glaser, K. B.; et al., "Gene expression profiling of multiple histone deacetylase (HDAC) inhibitors: defining a common gene set produced by HDAC inhibition in T24 and MDA carcinoma cell lines," Mol. Cancer Ther. 2003, 2, 151-163.
Grant, S.; et al., "Vorinostat," Nat. Rev. Drug Discovery. 2007, 6, 21-22.
Gray, S. G., "Epigenetic treatment of neurological disease," Epigenomics 2011, 3, 431-450.
Gray, S. G.; et al., "Rationale for the use of histone deacetylase inhibitors as a dual therapeutic modality in multiple sclerosis," Epigenetics 2006, 1, 67.
Grayson, D. R.; et al., "Is there a future for histone deacetylase inhibitors in the pharmacotherapy of psychiatric disorders," Mol. Pharmacol. 2010, 77, 126-135.
Greshock, T. J., et al., "Improved total synthesis of the potent HDAC inhibitor FK228 (FR-901228)," Org Lett 10, 2008, 613-616.
Guan, J.-S.; et al., "HDAC2 negatively regulates memory formation and synaptic plasticity," Nature 2009, 459, 55-60.
Haberland M, et al., "The many roles of histone deacetylases in development and physiology: implications for disease and therapy," Nat Rev Genet 2009, 10:32-42.
Howman, R. A.; et al., "New drug therapies in peripheral T-cell lymphoma," Expert Rev Anticancer Ther 2011, 11, 457.
Hubbert, C.; et al., "HDAC6 is a microtubule-associated deacetylase," Nature 2002, 417, 455-458.
Johnstone, R. W. "Histone-deacetylase inhibitors: novel drugs for the treatment of cancer," National Review Drug Discovery, 2002, 1, 287-299.
Jones, P. A.; et al., "The Epigenomics of Cancer," Cell 2007, 128, 683.
Kalin, J. H.; et al., "Creating zinc monkey wrenches in the treatment of epigenetic disorders," Current Opinion in Chemical Biology, 2009, 13, 263.
Karagiannis, T. C.; et al., "Will broad-spectrum histone deacetylase inhibitors be superseded by more specific compounds?" Leukemia 2007, 21, 61-65.
Kazantsev, A. G., et al., "Therapeutic application of histone deacetylase inhibitors for central nervous system disorders," Nature Reviews Drug Discovery, 2008, 7, 854.
Kelly, W. K., et al., "Phase I Study of an Oral Histone Deacetylase Inhibitor, Suberoylanilide Hydroxamic Acid, in Patients With Advanced Cancer," Journal of Clinical Oncology, 2005, 23, 3923.
Khan, O.; et al., "HDAC inhibitors in cancer biology: emerging mechanisms and clinical applications," Immunology Cell Biology, 2012, 90, 85-94.
Kilgore, M., et. al. "Inhibitors of Class 1 Histone Deacetylases Reverse Contextual Memory Deficits in a Mouse Model of Alzheimer's Disease," Neuropsychopharmacology, 35(4), 870-880. (2010).
Lane, A. A.; et al., "Histone deacetylase inhibitors in cancer therapy," Journal Clinical Oncology, 2009, 27, 5459-5468.
Li, K. W., et al., "Total synthesis of the antitumor depsipeptide FR-901,228", Journal of American Chemical Society, 118, 7237-7238, 1996.
Ma, X.; et al., "Histone Deacetylase Inhibitors Current Status and Overview of Recent Clinical Trials," Drugs 2009, 69, 1911.
Makala et al, "FK228 analogues induce fetal hemoglobin in human erythroid progenitors," 2012, Anemia. Article ID 428137, 13 pages.
Mann, B. S.; et al., "FDA Approval Summary: Vorinostat for Treatment of Advanced Primary Cutaneous T-Cell Lymphoma," The oncologist 2007, 12, 1247.
Marks, P. A., "Histone deacetylase inhibitors: a chemical genetics approach to understanding cellular functions," Biochimica et Biophysica Acta 2010, 1799:717-725.
Marks, P. A.; et al., "Histone Deacetylase Inhibitors," Advance in Cancer Research, 2004, 91, 137-168.
McQuown, S. C.; et al., "HDAC3 is a critical negative regulator of long-term memory formation," Journal of Neuroscience, 2011, 31, 764-774.
Minucci, S.; et al., "Histone deacetylase inhibitors and the promise of epigenetic treatments for cancer," Nature Reviews Cancer. 2006, 6, 38-51.
Miyake, K.; et al., "Expression of hypoxiainducible factor-1alpha, histone deacetylase 1, and metastasis associated protein 1 in pancreatic carcinoma: correlation with poor prognosis with possible regulation," Pancreas 2008, 36 (3), 105 e1-e9.
Newkirk et al. "Discovery, biological activity, synthesis and potential therapeutic utility of naturally occurring histone deacetylase inhibitors," 2009. Natural Products Reports. 26: 1293-1320.
Plumb, J. A.; et al., "Pharmacodynamic Response and Inhibition of Growth of Human Tumor Xenografts by the Novel Histone Deacetylase Inhibitor PXD101," Molecular Cancer Therapeutics, 2003, 2, 721.
Potharla, V. Y.; et al., "New Insights into the Genetic Organization of the FK228 Biosynthetic Gene Cluster in Chromobacterium violaceum No. 968," Applied Environmental Microbiology, 2011, 77, 1508.
Ptak, C.; Petronis, A. "Epigenetics and complex disease: from etiology to new therapeutics," Annual review of pharmacology and toxicology 2008, 48, 257.
Richon, V. M., et al., "Second generation hybrid polar compounds are potent inducers of transformed cell differentiation," Proc Natl Acad Sci U S A 93, 5705-5708, 1996.
Rikimaru, T., et al., "Clinical significance of histone deacetylase 1 expression in patients with hepatocellular carcinoma," Oncology 2007, 72, 69-74.
Hill, R.A., et al., Hot off the press. 2008. Natural Product Reports, 25: 997-1000.
Ropero, S.; et al., "The role of histone deacetylases (HDACs) in human cancer," Molecular Oncology, 2007, 1, 19-25.
Rotilli, D.; et al., "Non-cancer uses of histone deacetylase inhibitors: effects on infectious diseases and beta-hemoglobinopathies," Curr. Top. Med. Chem. 2009, 9, 272-291.
Salmi-Smail, C., et al., "Modified cap group suberoylanilide hydroxamic acid histone deacetylase inhibitor derivatives reveal improved selective antileukemic activity," Journal of Medicinal Chemistry, 53, 3038-3047, 2010.
Sandhu, P., et al "Disposition of vorinostat, a novel histone deacetylase inhibitor and anticancer agent, in preclinical species," Drug Metab Letters, 2007, 1, 153.
Stolze, S.C., et al., "Challenges in the Syntheses of Peptidic Natural Products," Synthesis, 44, 1755-1777, 2012.
Schrump, D. S. "Cytotoxicity mediated by histone deacetylase inhibitors in cancer cells: mechanisms and potential clinical implications," Clinical Cancer Research, 2009, 15, 3947.
Shi, B., "The development and potential clinical utility of biomarkers for HDAC inhibitors," Drug Discoveries and Therapeutics, 2013, 7, 129.
Shoemaker, R. H. "The NCI60 human tumour cell line anticancer drug screen," Nature Reviews Cancer 6, 813-823, 2006.

(56) References Cited

OTHER PUBLICATIONS

Spange, S.; et al., "Acetylation of non-histone proteins modulates cellular signalling at multiple levels," The International Journal of Biochemistry and Cell Biology, 2009, 41, 185-198.

Vecsey, C. G., et. al. "Histone Deacetylase Inhibitors Enhance Memory and Synaptic Plasticity via CREB: CBPDependent Transcriptional Activation," The Journal of Neuroscience : The Official Journal of the Society for Neuroscience, 27(23), 6128-6140. (2007).

Verdin, E.; et al., "Class II histone deacetylases Versatile regulators," Trends Genet. 2003, 19, 286-293.

Wagner JM, et al., "Histone deacetylase (HDAC) inhibitors in recent clinical trials for cancer therapy," Clinical Epigenetics 2010, 1:117-136.

Wang, C., et al., "Discovery and activity profiling of thailandepsins A through F, potent histone deacetylase inhibitors, from Burkholderia thailandensis E264," Medical Chemistry Communications, 3, 976-981, 2012.

Wang, C.; et al., "Thailandepsin A," Acta Crystallographica Section E, Structure Reports, Online 2011, 67, 02948.

Wang, C.; et al., "Thailandepsins: Bacterial Products with Potent Histone Deacetylase Inhibitory Activities and Broad-Spectrum Antiproliferative Activities," Journal Natural Products, 2011, 74, 2031.

Wang, C.; et al., "An FAD-dependent pyridine nucleotide-disulfide oxidoreductase is involved in disulfide bond formation in FK228 anticancer depsipeptide," Chemical Biology, 16, 585, 2009.

Wang, H.; et al., "New patented histone deacetylase inhibitors," Expert opinion on therapeutic patents, 2009, 19, 1727.

Weichert, W.; et al., "Histone deacetylases 1, 2 and 3 are highly expressed in prostate cancer and HDAC2 expression is associated with shorter PSA relapse time after radical prostatectomy," British Journal of Cancer, 2008, 98, 604-610.

Weichert, W.; et al., "Class I histone deacetylase expression has independent prognostic impact on human colorectal cancer: Specific role of class I histone deacetylases in vitro and in vivo," Clinical of Cancer Research, 2008, 14, 1669-1677.

Wen, S., et al., "Macrolactamization versus macrolactonization: total synthesis of FK228, the depsipeptide histone deacetylase inhibitor," Journal of Organic Chemistry, 73, 9353-9361, 2008.

Zhaoyang, L.; et al., "A subnanogram API LC/MS/MS quantitation method for depsipeptide FR901228 and its preclinical pharmacokinetics," Journal of Pharmaceutical and Biomedical Analysis 2000, 22, 33.

Wesener, S. R.; et al., "Reconstitution of the FK228 biosynthetic pathway reveals cross talk between modular polyketide synthases and fatty acid synthase," Applied Environmental Microbiology, 2011, 77, 1501.

Wiech NL, et al., "Inhibition of histone deacetylases: a pharmacological approach to the treatment of non-cancer disorders," Curr Top Med Chem, 2009, 9:257-271.

Wilson, A. J., et al., "Thailandepsins are new small molecule class I HDAC inhibitors with potent cytotoxic activity in ovarian cancer cells: a preclinical study of epigenetic ovarian," Journal of Ovarian Research, 2012, 5, 12.

Witt, O.; et al., "HDAC family: What are the cancer relevant targets," Cancer Lett. 2009, 277, 8-21.

Yoo, C. B.; et al., "Epigenetic therapy of cancer: past, present and future," Nature Reviews Drug Discovery, 2006, 5, 37.

Zhang, Y.; et al., "Two catalytic domains are required for protein deacetylation," Journal of Biological Chemistry, 2006, 281, 2401-2404.

Zhang, Y., et al., "HDAC-6 interacts with and deacetylates tubulin and microtubules in vivo," The EMBO Journal, 2003, 22, 1168-1179.

Zou, H., et al., "Characterization of the two catalytic domains in histone deacetylase 6," Biochemical and Biophysical Research Communications, 2006, 341, 45-50.

PCT/US2015/058167 International Search Report and Written Opinion of the International Searching Authority dated Jan. 21, 2016 (13 pages).

\* cited by examiner

Parental compounds

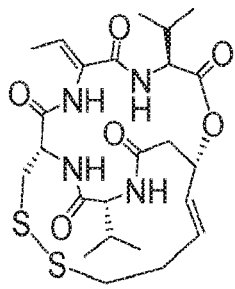

FK228 (istodax®)

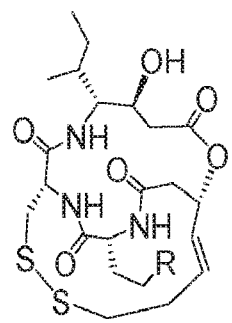

Thailandepsin A (R=SCH₃)
Thailandepsin B (R=CH₂CH₃)

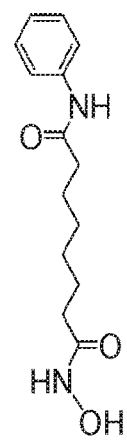

SAHA (Zolinza®)

Designer compounds

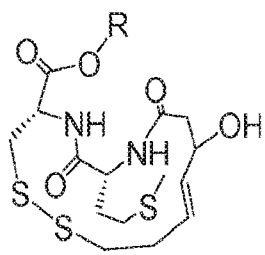

Cpd1 / Cpd1'

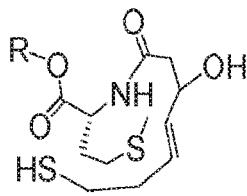

Cpd2 / Cpd2'

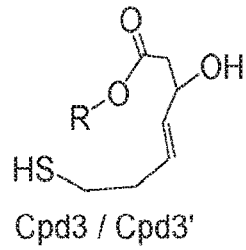

Cpd3 / Cpd3'

Cpd set 1:
Cpds 1-3 (R=H) and
Cpds 1'-3' (R=CH₃).

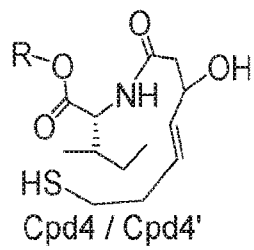

Cpd4 / Cpd4'

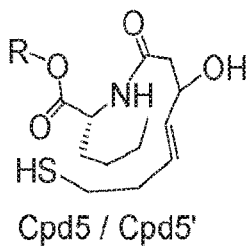

Cpd5 / Cpd5'

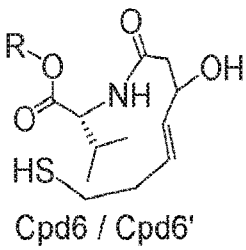

Cpd6 / Cpd6'

Cpd set 2:
Cpds 4-6 (R=H) and
Cpds 4'-6' (R=CH₃).

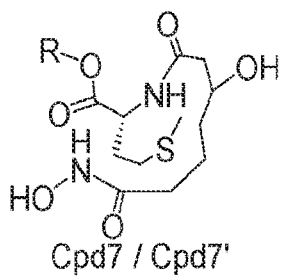

Cpd7 / Cpd7'

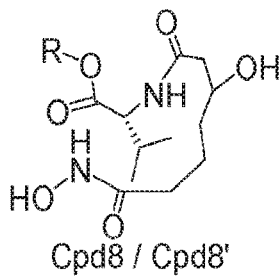

Cpd8 / Cpd8'

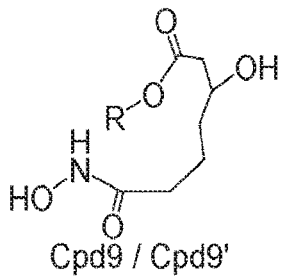

Cpd9 / Cpd9'

Cpd set 3:
Cpds 7-9 (R=H) and
Cpds 7'-9' (R=CH₃).

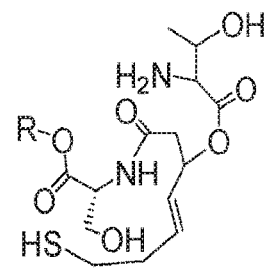

Cpd10 / Cpd10'

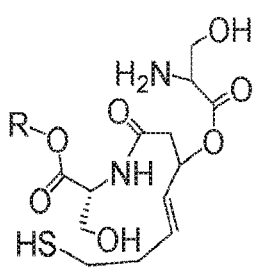

Cpd11 / Cpd11'

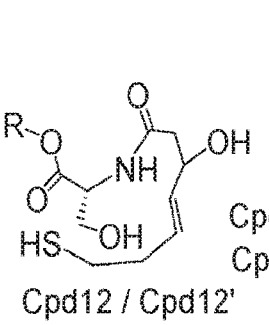

Cpd12 / Cpd12'

Cpd set 4:
Cpds 10-12 (R=H) and
Cpds 10'-12' (R=CH₃).

FIG. 1

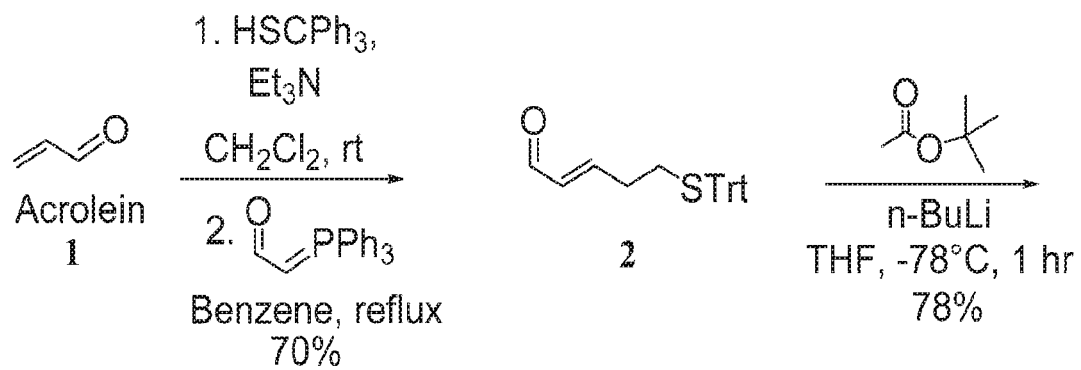
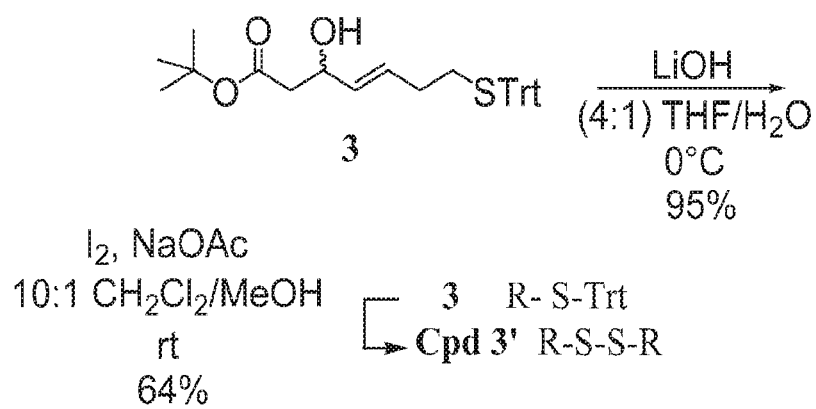
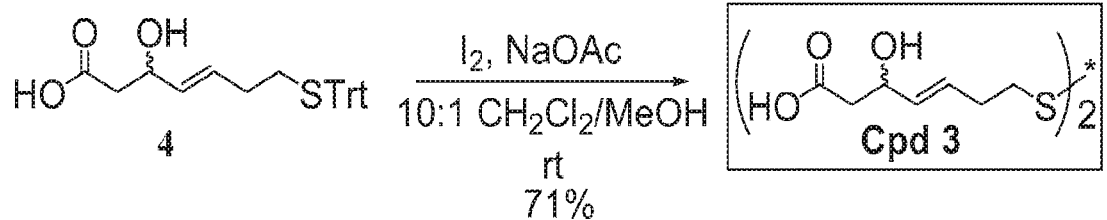
FIG. 2A

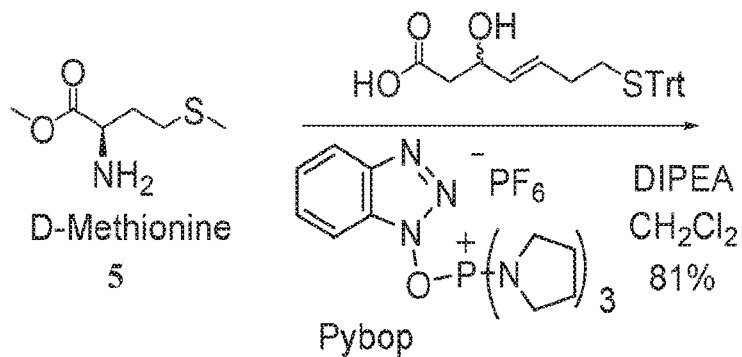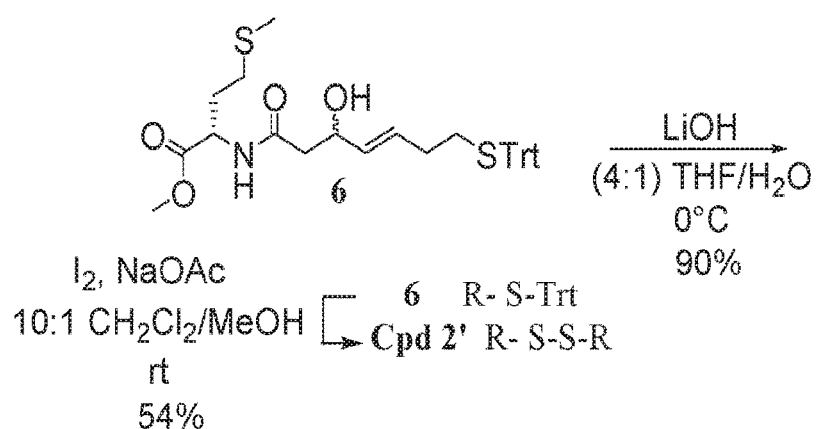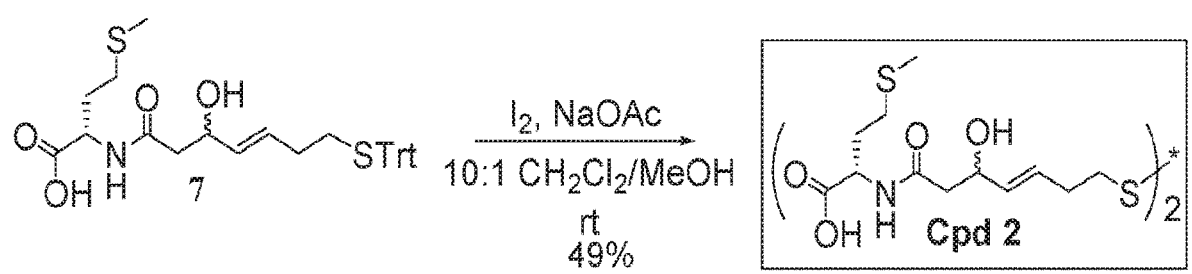
FIG. 2B

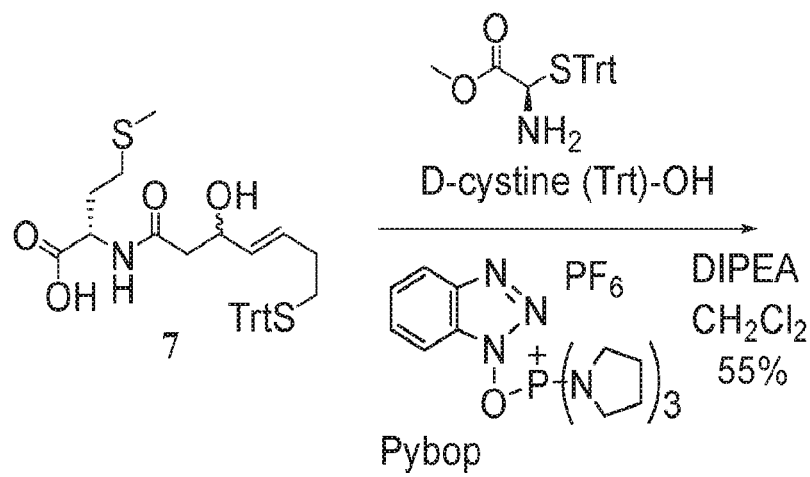
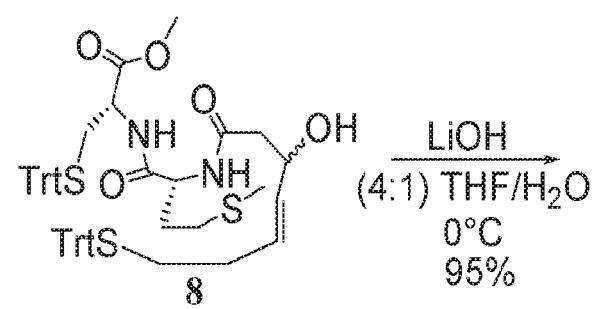
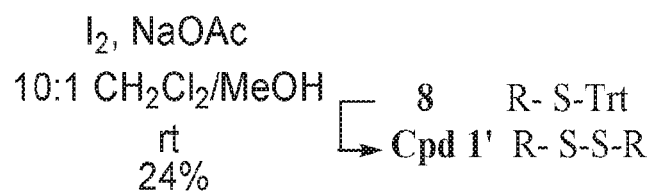
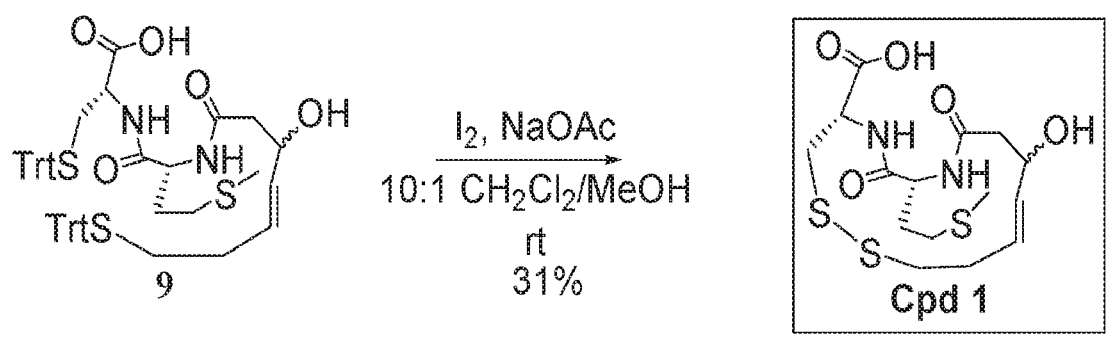
FIG. 2C

HDAC INHIBITORS AND METHODS OF TREATMENT USING THE SAME

CROSS-REFERENCE TO RELATED APPLICATIONS

This application claims priority to U.S. Provisional Patent Application No. 62/211,304, filed Aug. 28, 2015, which is incorporated herein by reference in its entirety.

STATEMENT REGARDING FEDERALLY SPONSORED RESEARCH

This invention was made with government support under grant 1 R01 CA152212 awarded by the United States National Institutes of Health. The government has certain rights in the invention.

FIELD

This disclosure relates to novel HDAC inhibitors and methods and compositions including the same for treating cancer and neurodegenerative disorders.

INTRODUCTION

The epigenome of eukaryotic cells is delicately maintained by several classes of enzymes including DNA methyltransferases, histone acetyltrans-ferases, and histone deacetylases (HDACs). Aberrant modifications of DNA or histones often lead to diseases including cancer, central nerve system (CNS) disorders, and autoimmune diseases. Consequently, epigenetic intervention of some of those enzymes has emerged as a promising avenue toward disease therapy. In particular, selective inhibition of HDACs by small molecules often leads to a cascade of chromatin remodeling, tumor suppressor gene reactivation, apoptosis, and regression of cancer. HDAC inhibitors have thus gained much attention in recent years as a new class of anticancer agents. One synthetic HDAC pan-inhibitor, SAHA (suberoyl anilide hydroxamic acid, vorinostat, ZOLINZA®, Merck, Kenilworth, N.J.) and one natural product HDAC inhibitor (a class I selective inhibitor), FK228 (depsipeptide, romidepsin, ISTODAX®, Celgene Corporation, Summit, N.J.), have been approved by FDA for the treatment of two types of T-cell lymphoma. Other HDAC inhibitors (mostly synthetic molecules) are in various stages of preclinical or clinical trials as single agents or in combination with other chemotherapy drugs for diverse cancer types. However, many of the currently available HDAC inhibitors are highly toxic and/or have poor solubility.

Memory deficits are common to aging and neurodegenerative diseases like Alzheimer's Disease. Because the U.S. population is rapidly aging, the incidence of memory dysfunction is anticipated to increase exponentially. Pharmacological interventions that prevent or delay memory loss associated with aging would substantially improve quality of life for affected individuals, increase their productivity, and decrease the health care costs for those with memory loss and dementia. Although memory dysfunction is a significant impediment to independent living and diminishes workforce productivity, few available treatments effectively prevent or reverse memory impairments. Current medications to treat Alzheimer's Disease and other dementias are marginally effective and mostly effective only in early dementia, but not in later dementia. Therefore, there is significant need for more effective therapies to improve cognition in an aging population.

SUMMARY

In an aspect, the disclosure relates a compound according to Formula (I):

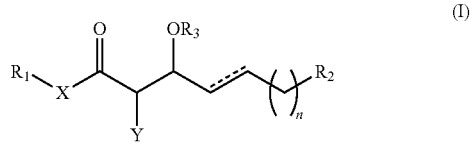

and stereoisomers and salts thereof;
wherein X is NH or O or a direct bond;
$R_1$ is H, $C_{1-10}$ alkyl, aryl, heteroaryl, or —NH—CHR$_a$C(O)—OR$_4$;
$R_a$ is an amino acid side chain, H, $C_{1-10}$ alkyl, $C_{1-10}$ heteroalkyl, aryl, or heteroaryl;
$R_4$ is H, $C_{1-10}$ alkyl, heteroaryl, or aryl;
$R_2$ is SH, SeH, or C(O)NHOH, or the compound can form a disulfide or diselenide dimer at the $R_2$ position;
$R_3$ is H, $C_{1-10}$ alkyl, heteroaryl, aryl, or —C(O)R$_5$;
$R_5$ is $C_{1-10}$ alkyl, heteroaryl, aryl, or —CH(N(R$_N$)$_2$)(CR'R"OR$_O$);
R' is H or $C_{1-10}$ alkyl, heteroaryl, or aryl;
R" is H or $C_{1-10}$ alkyl, heteroaryl, or aryl;
each $R_N$ is independently H, $C_{1-10}$ alkyl, heteroaryl, or aryl;
$R_O$ is H, $C_{1-10}$ alkyl, heteroaryl, or aryl;
Y is H, $C_{1-10}$ alkyl, heteroaryl, aryl, or halogen;
n is an integer from 0 to 5;
wherein if X is a direct bond, then $R_1$ is —NH—CHR$_a$C(O)—OR$_4$; and
wherein the dashed bond indicates the presence of an optional double bond.

In a further aspect, the disclosure relates to a compound according to Formula (II):

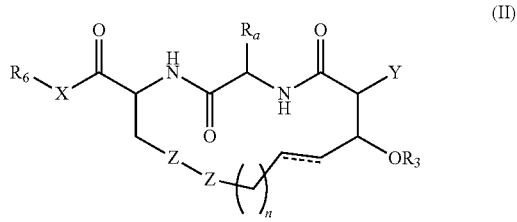

and stereoisomers and salts thereof;
wherein Z is S or Se;
X is NH or O or a direct bond;
$R_6$ is H, $C_{1-10}$ alkyl, heteroaryl, aryl, or —NH—CHR$_a$C(O)—OR$_4$;
$R_a$ is an amino acid side chain, H, $C_{1-10}$ alkyl, $C_{1-10}$ heteroalkyl, aryl, or heteroaryl;
$R_4$ is H, $C_{1-10}$ alkyl, heteroaryl, or aryl;
$R_3$ is H, $C_{1-10}$ alkyl, heteroaryl, aryl, or —C(O)R$_5$;
$R_5$ is $C_{1-10}$ alkyl, heteroaryl, aryl, —CH(N(R$_N$)$_2$)(CR'R"OR$_O$);
R' is H, $C_{1-10}$ alkyl, heteroryl, or aryl;
R" is H, $C_{1-10}$ alkyl, heteroaryl, or aryl;

each $R_N$ is independently H, $C_{1-10}$ alkyl, heteroaryl, or aryl;

$R_O$ is H or $C_{1-10}$ alkyl, heteroaryl, or aryl;

Y is H, $C_{1-10}$ alkyl, heteroaryl, aryl, or halogen;

wherein if X is a direct bond, then $R_6$ is —NH—CHR$_a$C(O)—OR$_4$;

n is an integer from 0 to 5; and wherein the dashed bond indicates the presence of an optional double bond.

In some embodiments, X is a direct bond and $R_1$ or $R_6$ is —NH—CHR$_a$C(O)—OR$_4$. In some embodiments, X is NH. In some embodiments, X is O. In some embodiments, $R_a$ is H, $C_{1-10}$ alkyl, aryl, heteroaryl, or halogen. In some embodiments, $R_a$ is an amino acid side chain. In some embodiments, the amino acid is an aliphatic amino acid, hydroxyl- or sulfer- or selenium-containing amino acid, cyclic amino acid, aromatic amino acid, or basic amino acid. In some embodiments, the amino acid is an aliphatic amino acid or a hydroxyl- or sulfer- or selenium-containing amino acid. In some embodiments, the amino acid is glycine, alanine, isoleucine, leucine, serine, valine, or methionine. In some embodiments, the amino acid is isoleucine, serine, valine, or methionine. In some embodiments, $R_1$ is H. In some embodiments, $R_1$ is $C_{1-10}$ alkyl. In some embodiments, $R_1$ is $C_{1-4}$ alkyl. In some embodiments, $R_2$ is SH. In some embodiments, $R_2$ is SeH. In some embodiments, the compound forms a disulfide dimer at the $R_2$ position. In some embodiments, the compound forms a diselenide dimer at the $R_2$ position. In some embodiments, $R_3$ is H. In some embodiments, $R_3$ is —C(O)R$_5$. In some embodiments, $R_5$ is —CH(N(R$_N$)$_2$)(CR'R"OR$_O$). In some embodiments, at least one $R_N$ is H. In some embodiments, both $R_N$ are H. In some embodiments, $R_O$ is H. In some embodiments, one of R' and R" is H and the other is $C_{1-10}$ alkyl. In some embodiments, one of R' and R" is methyl. In some embodiments, both R' and R" are H. In some embodiments, $R_4$ is H. In some embodiments, $R_4$ is $C_{1-10}$ alkyl. In some embodiments, $R_4$ is methyl or ethyl. In some embodiments, Y is H. In some embodiments, Z is S. In some embodiments, Z is Se. In some embodiments, the optional double bond is present.

In some embodiments, the compound is selected from the following:

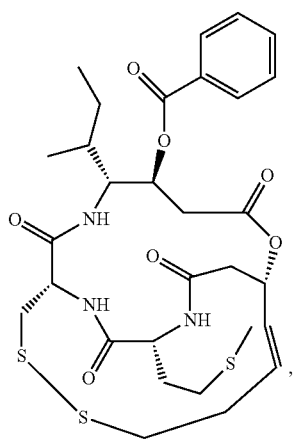

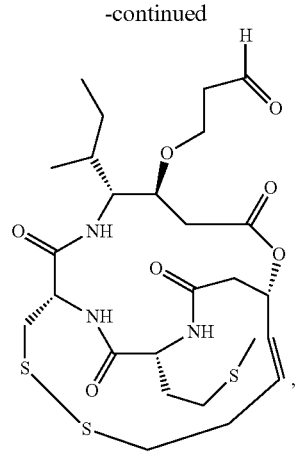

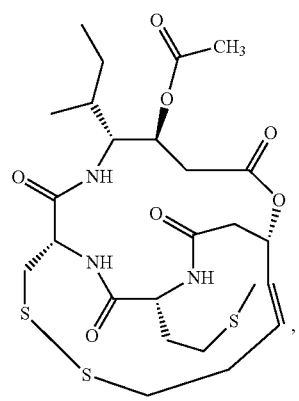

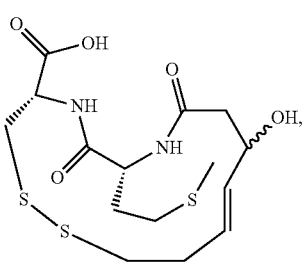

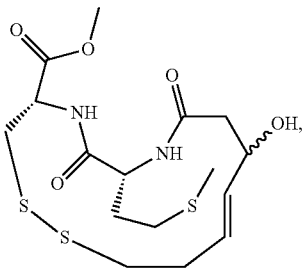

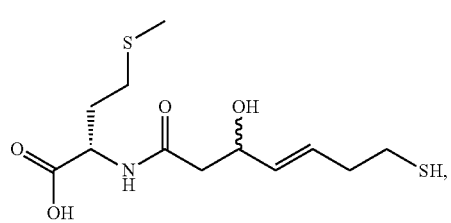

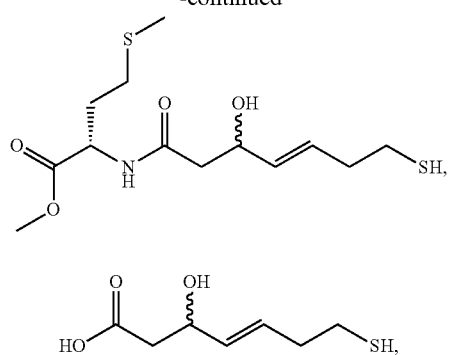
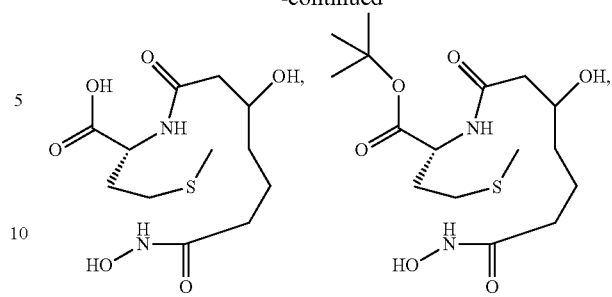
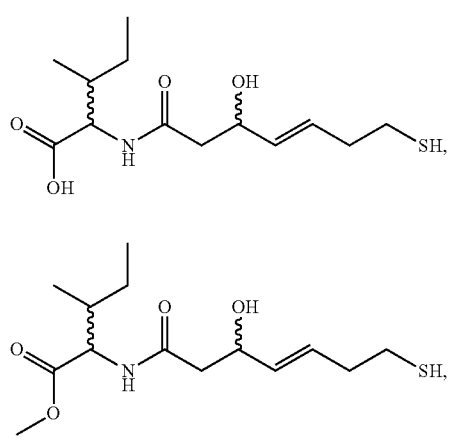
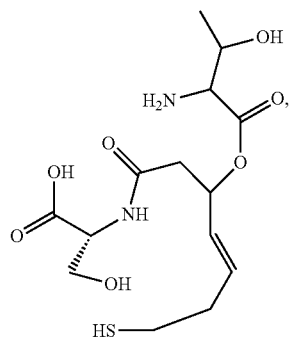
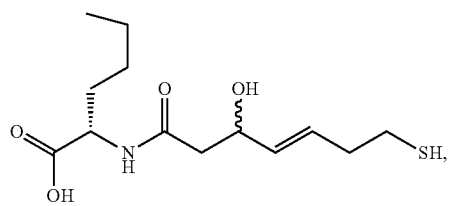
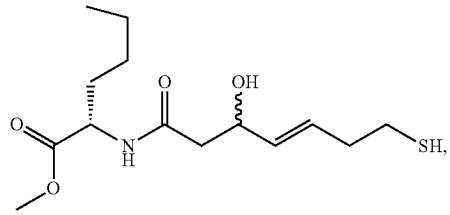
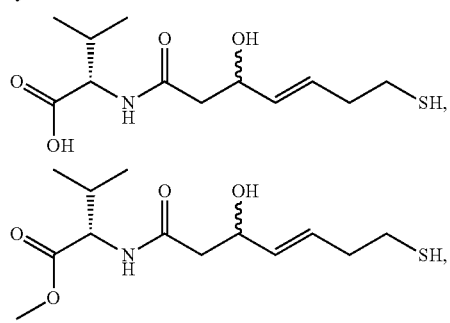
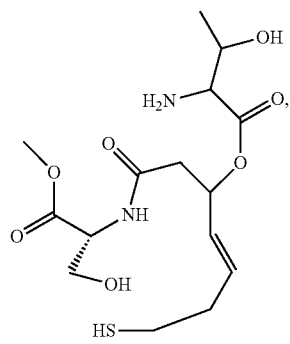

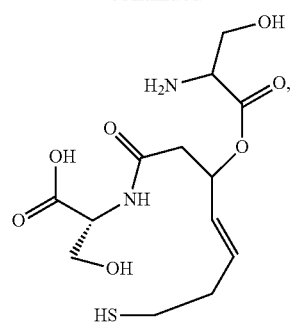
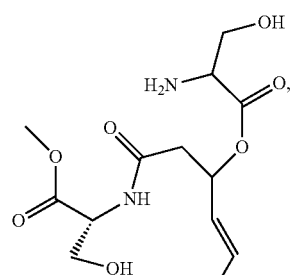
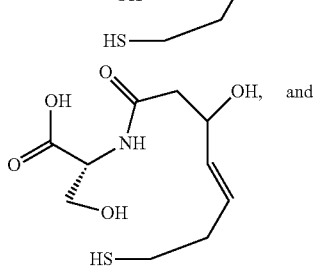
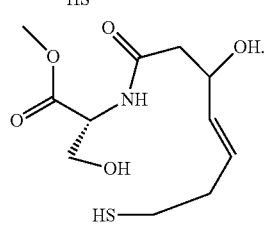
In some embodiments, the compound is not at least one of the following compounds:
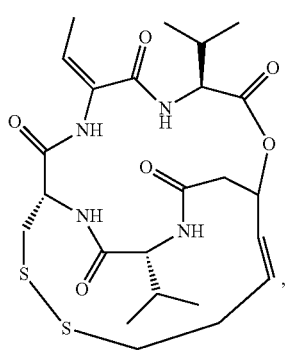
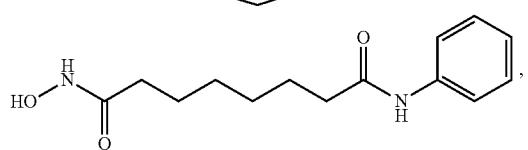
TDP-A
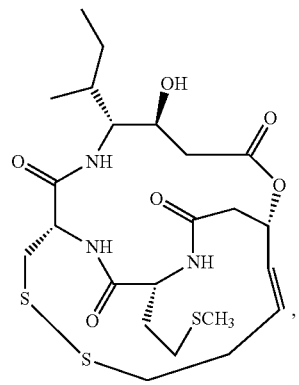
TDP-B
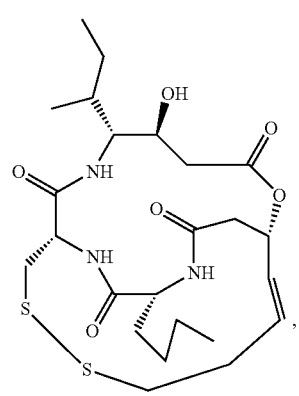
TDC1
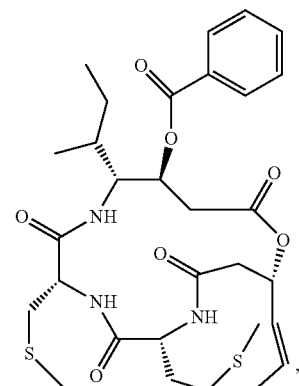
TDC2
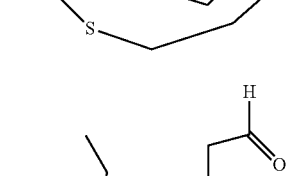
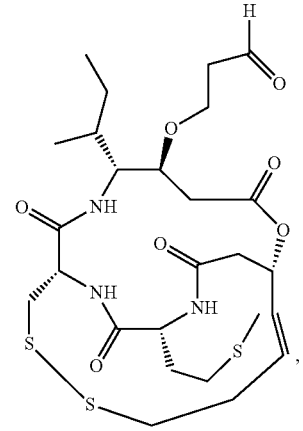

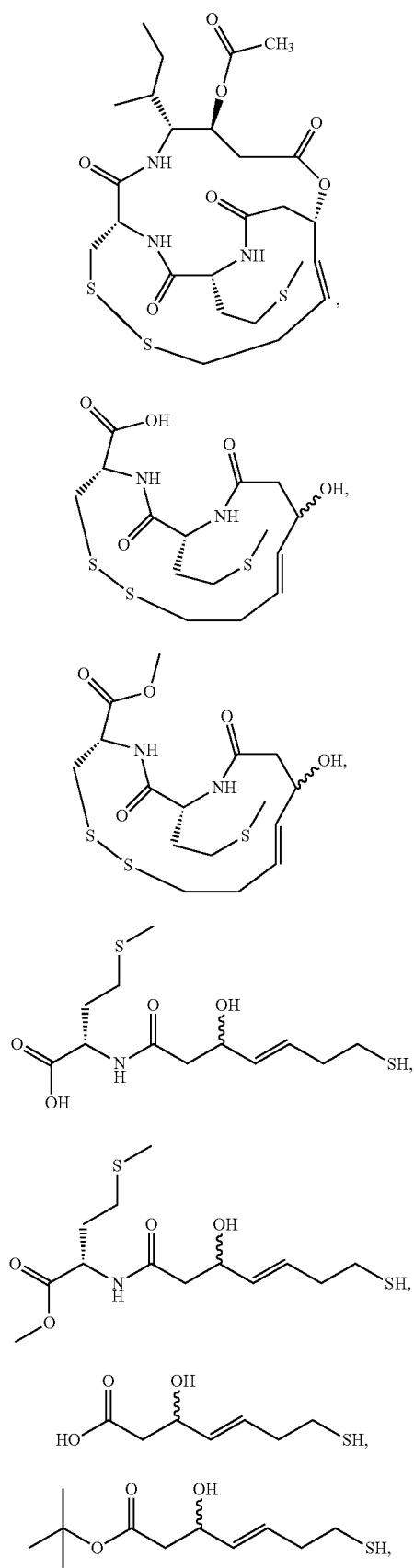
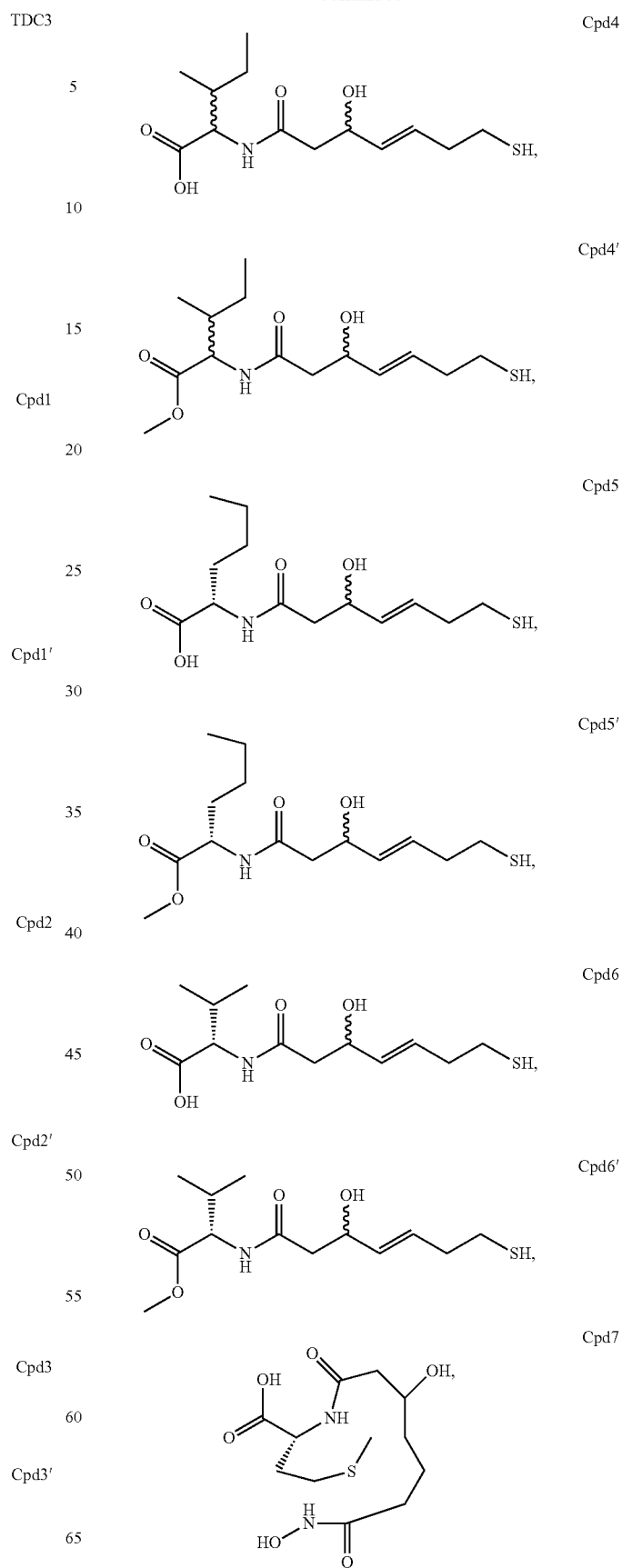

-continued

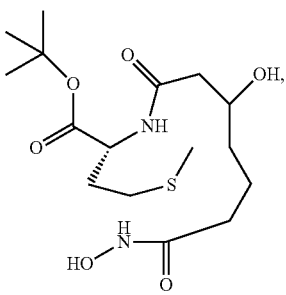

Cpd7'

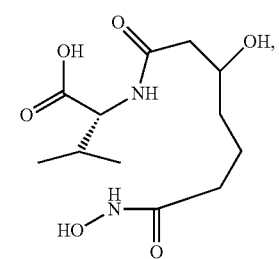

Cpd8

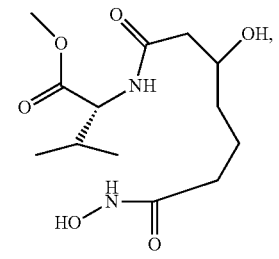

Cpd8'

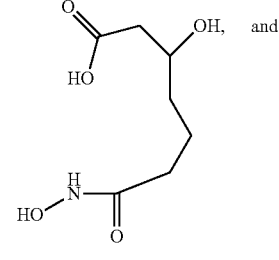

Cpd9

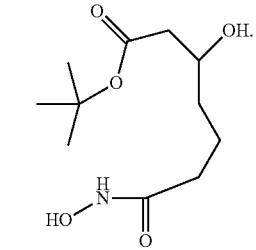

Cpd9'

Another aspect of the disclosure provides a pharmaceutical composition including a compound as disclosed herein and a pharmaceutically acceptable carrier.

Another aspect of the disclosure provides a method of treating cancer. The method includes administering an effective amount of a compound as disclosed herein to a subject in need thereof. In some embodiments, the cancer is selected from colon, melanoma, ovarian, T cell lymphoma, and renal cancer.

Another aspect of the disclosure provides a method of treating a subject with a neurological disorder. The method includes administering an effect amount of a compound as disclosed herein to a subject in need thereof. In some embodiments, the neurological disorder is selected from dementia, memory deficit, memory dysfunction, memory loss, cognition defects, amyotrophic lateral sclerosis, Alzheimer's Disease, Parkinson's Disease, Huntington's Disease, mood disorder, substance abuse, and schizophrenia. In some embodiments, the neurological disorder is selected from dementia, memory deficit, memory dysfunction, memory loss, cognition defects, and Alzheimer's Disease. In some embodiments, the mood disorder is selected from depression and bipolar disorder.

Another aspect of the disclosure provides a method of enhancing memory and/or improving cognition. The method includes administering an effect amount of a compound as disclosed herein to a subject in need thereof.

Another aspect of the disclosure provides a method of inhibiting a HDAC in a subject in need thereof. The method includes administering an effect amount of a compound as disclosed herein to the subject.

The disclosure provides for other aspects and embodiments that will be apparent in light of the following detailed description and accompanying Figures.

BRIEF DESCRIPTION OF THE DRAWINGS

FIG. 1 shows the structure of HDAC inhibitors.
FIG. 2 is a schematic for the synthesis of compounds Cpd1, Cpd1', Cpd2, Cpd2', Cpd3, and Cpd3'.

DETAILED DESCRIPTION

Figure 3:
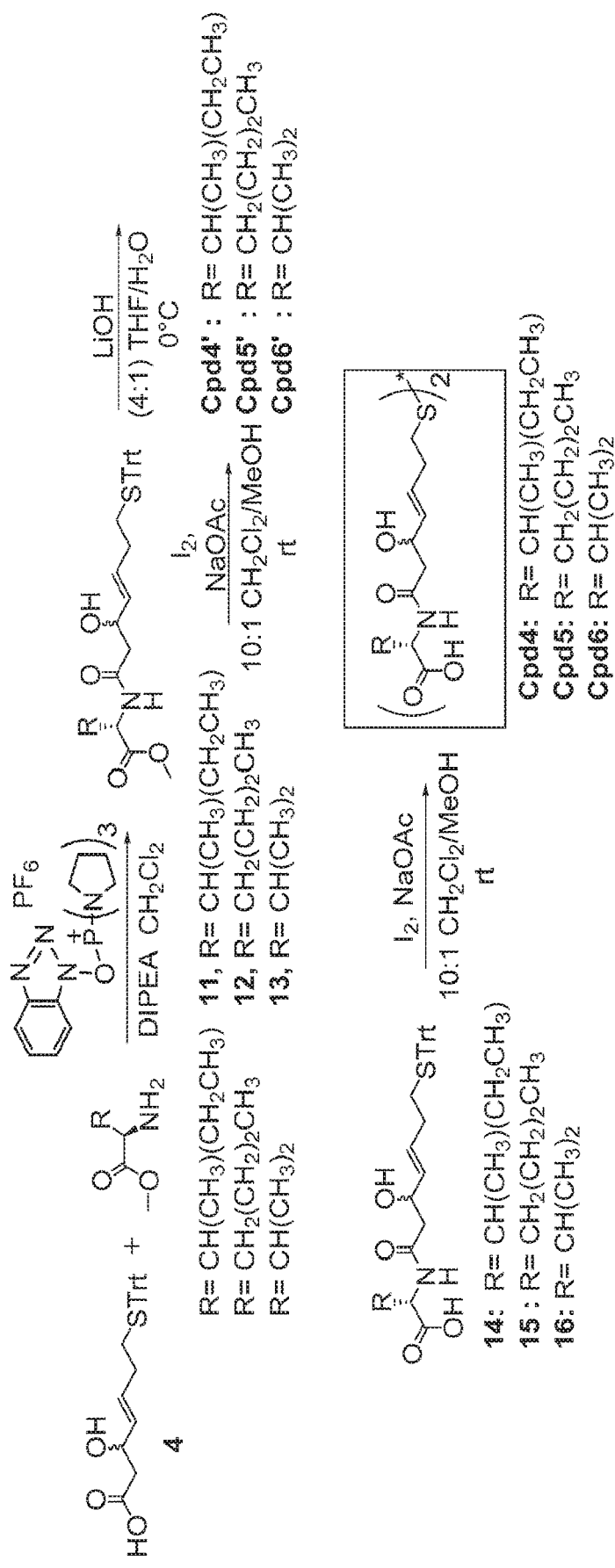
FIG. 3 is a schematic for the synthesis of compounds Cpd4, Cpd4', Cpd5, Cpd5', Cpd6, and Cpd6'.

Natural product-based histone deacetylase (HDAC) inhibitors such as thailandepsin and romidepsin (FK228), as shown in FIG. 1, are usually potent and moderately isoform-selective, but they are often associated with poor solubility and excessive cytotoxicity. In an attempt to overcome these limitations, as detailed herein, modification of the hydroxyl moiety of thailandepsin A (TDP-A) generated three new derivatives with a benzoyl, an ethyl formate, or an acetyl group. Cytotoxicity and solubility of these derivatives (TDC1, TDC2, and TDC3) was greatly reduced compared to TDP-A, but the HDAC inhibitory and antiproliferative activity of the derivatives was decreased against a number of tumor cell lines. A series of novel compounds based on the scaffolds of thailandepsin A, thailandepsin B, and FK228, were also designed and synthesized from molecular modeling. As detailed herein, all of the novel compounds had significantly improved solubility and much less cytotoxicity compared to the parent natural product-based HDAC inhibitors and also retained potent HDAC inhibitory activity towards class I HDACs, particularly HDAC1. The novel HDAC inhibitors detailed herein are efficacious in various methods of treatment, for example, for treating cancer and neurodegenerative disorders.

1) DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987; the entire contents of each of which are incorporated herein by reference.

The term "acyl" refers to an alkylcarbonyl, cycloalkylcarbonyl, heterocyclylcarbonyl, arylcarbonyl, or heteroarylcarbonyl substituent, any of which may be further substituted (e.g., with one or more substituents).

The term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms, and $C_1$-$C_4$ alkyl indicates that the alkyl group may have from 1 to 4 (inclusive) carbon atoms. An alkyl group may be optionally substituted. Examples of $C_1$-$C_4$ alkyl groups include methyl, ethyl, n-propyl, isopropyl, n-butyl, sec-butyl, and tert-butyl.

The term "alkenyl" refers to a straight or branched hydrocarbon chain having one or more double bonds. Examples of alkenyl groups include, but are not limited to, allyl, propenyl, 2-butenyl, 3-hexenyl, and 3-octenyl groups. One of the double bond carbons may optionally be the point of attachment of the alkenyl substituent. An alkenyl group may be optionally substituted.

The term "alkynyl" refers to a straight or branched hydrocarbon chain having one or more triple bonds. Examples of alkynyl groups include, but are not limited to, ethynyl, propargyl, and 3-hexynyl. One of the triple bond carbons may optionally be the point of attachment of the alkynyl substituent. An alkynyl group may be optionally substituted.

The term "amino acid" refers to molecules containing an amine group, a carboxylic acid group, and a side chain that varies between different amino acids. Amino acids are well known to those skilled in the art. Amino acids include alpha-amino acids of the general formula $H_2NCHRCOOH$, where R is an amino acid side chain comprising an organic substituent, as well as uniquely structured amino acids such as, for example, proline. Amino acids include, for example, isoleucine, leucine, alanine, asparagine, glutamine, lysine, aspartic acid (aspartate), glutamic acid (glutamate), methionine, cysteine, phenylalanine, threonine, tryptophan, glycine, valine, proline, serine, tyrosine, arginine, histidine, norleucine, ornithine, taurine, selenocysteine, selenomethionine, lanthionine, 2-aminoisobutyric acid, dehydroalanine, hypusine, citrulline, 3-aminopropanoic acid, gamma-aminobutryic acid, and the like. Amino acids include aliphatic amino acids, including glycine, alanine, valine, leucine, isoleucine, and other hydrocarbon side chains. Amino acids include hydroxyl- or sulfer- or selenium-containing amino acids, including serine, cysteine, selenocysteine, threonine, and methionine. Amino acids include cyclic amino acids, including proline. Amino acids include aromatic amino acids, including phenylalanine, tyrosine, and tryptophan. Amino acids include basic amino acids, including histidine, lysine, and arginine. Amino acids include acidic amino acids and their amide, including aspartate, glutamate, asparagine, and glutamine. Accordingly, the term "amino acid side chain" refers to the various organic substituent groups (e.g., "R" in $H_2NCHRCOOH$) that differentiate one amino acid from another. A "derivative" of an amino acid side chain refers to an amino acid side chain that has been modified structurally (e.g., through chemical reaction to form new species, covalent linkage to another molecule, etc.). The terms "amino acid" and "amino acid side chain" refer to both natural and unnatural amino acids.

The term "aryl" refers to an aromatic monocyclic, bicyclic, or tricyclic hydrocarbon ring system, wherein any ring atom capable of substitution can be substituted (e.g., with one or more substituents). Examples of aryl moieties include, but are not limited to, phenyl, naphthyl, and anthracenyl.

The term "arylalkyl" refers to an alkyl moiety in which an alkyl hydrogen atom is replaced with an aryl group. Arylalkyl includes groups in which more than one hydrogen atom has been replaced with an aryl group. Examples of arylalkyl groups include benzyl, 2-phenylethyl, 3-phenylpropyl, 9-fluorenyl, benzhydryl, and trityl groups.

The term "cycloalkyl" as used herein refers to nonaromatic, saturated or partially unsaturated cyclic, bicyclic, tricyclic, or polycyclic hydrocarbon groups having 3 to 12 carbons (e.g., 3, 4, 5, 6 or 7 carbon atoms). Any ring atom can be substituted (e.g., with one or more substituents). Cycloalkyl groups can contain fused rings. Fused rings are rings that share one or more common carbon atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl, and norbornenyl.

The term "halo" or "halogen" as used herein refers to any radical of fluorine, chlorine, bromine, or iodine.

The term "haloalkyl" as used herein refers to an alkyl in which one or more hydrogen atoms are replaced with a halogen, and includes alkyl moieties in which all hydrogens have been replaced with halogens (e.g., perfluoroalkyl such as $CF_3$).

The term "heteroalkyl" as used herein, means an alkyl group, as defined herein, in which one or more of the carbon atoms has been replaced by a heteroatom selected from S, O, P, and N. Representative examples of heteroalkyls include, but are not limited to, alkyl ethers, secondary and tertiary alkyl amines, amides, and alkyl sulfides.

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P, and Si (e.g., carbon atoms and 1-3, 1-6, or 1-9 heteroatoms independently selected from O, N, S, P, and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include, but are not limited to, radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines, and purines.

The term "heterocyclyl" as used herein refers to a non-aromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si, and P (e.g., carbon atoms and 1-3, 1-6, or 1-9 heteroatoms of O, N, S, Si, and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

The term "hydroxy" refers to an —OH radical. The term "alkoxy" refers to an —O-alkyl radical. The term "aryloxy" refers to an —O-aryl radical. The term "haloalkoxy" refers to an —O-haloalkyl radical.

The term "substituent" refers to a group "substituted" on an alkyl, alkenyl, alkynyl, cycloalkyl, heterocyclyl, aryl, arylalkyl, or heteroaryl group at any atom of that group. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C=O), phosphonate, sulfinyl, sulfonyl, sulfonate, sulfonamino, sulfonamido, thioamido, thiol, thioxo (e.g., C=S), and ureido. In embodiments, substituents on a group are independently any one single, or any combination of the aforementioned substituents. In embodiments, a substituent may itself be substituted with any one of the above substituents.

The above substituents may be abbreviated herein, for example, the abbreviations Me, Et, and Ph represent methyl, ethyl, and phenyl, respectively. A more comprehensive list of the abbreviations used by organic chemists appears in the first issue of each volume of the Journal of Organic Chemistry; this list is typically presented in a table entitled Standard List of Abbreviations. The abbreviations contained in said list, and all abbreviations used by organic chemists of ordinary skill in the art, are hereby incorporated by reference.

For compounds, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—.

In accordance with a convention used in the art, the group:

is used in structural formulas herein to depict the bond that is the point of attachment of the moiety or substituent to the core or backbone structure.

The term "about" as used in connection with a numerical value throughout the specification and the claims denotes an interval of accuracy, familiar and acceptable to a person skilled in the art. In general, such interval of accuracy is ±10%.

The term "cancer" may include sarcoma, carcinoma, lymphoma, adenoma, melanoma, myeloid leukemia, lymphatic leukemia, blastoma, glioma, astrocytoma, mesothelioma, or a germ cell tumor. The cancer may include, but is not limited to, ovarian, lung, small cell lung, head, colorectal, rectal, gastric, heart, liver, pancreatic, bladder, prostate, colon, breast, testicular, brain, skin, esophageal, tracheal, head and neck, lymphoid, leukemia, glioblastoma, vulvar, melanoma, mesothelioma, renal, thyroid, soft tissue, and bone cancer. In certain aspects as disclosed herein, cancer includes renal, colon, melanoma, ovarian, and T cell lymphoma cancers.

"Carrier" means one or more compatible substances that are suitable for administration to a subject. Carrier includes solid or liquid fillers, diluents, hydrotopes, surface-active agents, and encapsulating substances. "Compatible" means that the components of the composition are capable of being commingled with an HDAC inhibitor, and with each other, in a manner such that there is no interaction which would substantially reduce the efficacy of the composition under ordinary use situations. Carriers must be of sufficiently high purity and sufficiently low toxicity to render them suitable for administration to the mammal being treated. The carrier can be inert, or it can possess pharmaceutical benefits, cosmetic benefits, or both. Suitable carriers, excipients, etc. can be found in standard pharmaceutical texts, for example, Remington's Pharmaceutical Sciences, 18th edition, Mack Publishing Company, Easton, Pa., 1990.

The term "histone deacetylase" or "HDAC" as used herein refers to the histone deacetylase polypeptide. HDAC refers to an enzyme that removes acetyl groups (O=C—CH$_3$) from an ε-N-acetyl lysine amino acid on a histone, allowing the histones to wrap the DNA more tightly. In particular, the term HDAC refers to any mammalian HDAC, for example, isoforms 1, 2, 3, 4, 5, 6, 7, 8, 9, 10, and 11 (that is, HDAC1, HDAC2, HDAC3, HDAC4, HDAC5, HDAC6, HDAC7, HDAC8, HDAC9, HDAC10, and HDAC11). In certain aspects, HDAC is a human HDAC. HDAC may include a class I HDAC (HDAC1, HDAC2, HDAC3, or HDAC8, or a combination thereof). HDAC may include a class II HDAC (HDAC4, HDAC5, HDAC6, HDAC7, HDAC9, or HDAC10, or a combination thereof). HDAC may include a class IIA HDAC (HDAC4, HDA 5, HDAC7, or HDAC9, or a combination thereof). HDAC may include a class IIB HDAC (HDAC6 or HDAC10, or a combination thereof). HDAC may include a class III HDAC (SIRT 1, SIRT2, SIRT3, SIRT4, SIRT5, SIRT6, or SIRT7, or a combination thereof). HDAC may include a class IV HDAC (HDAC11).

The term "inhibitor" encompasses agents that inhibit the activity of one or more polypeptides or proteins. For example, an inhibitor may indirectly or directly bind and inhibit the activity of the polypeptide or protein, including binding activity or catalytic activity. An inhibitor may prevent expression of the polypeptide or protein, or inhibit the ability of the polypeptide or protein to mediate binding or reaction with its target.

An inhibitor is said to competitively inhibit binding of a HDAC to a given target if it preferentially binds to that HDAC to the extent that it blocks, to some degree, binding of the HDAC to the target. Competitive inhibition can be determined by any method known in the art, for example, competition ELISA assays. An inhibitor can be said to competitively inhibit binding of the HDAC to a given target by at least 90%, at least 80%, at least 70%, at least 60%, or at least 50%.

The term "neurological disorder" as used herein includes central nervous system disorders and neurodegenerative disorders. Examples of neurological disorders include, for example, dementia, memory deficit, memory dysfunction, memory loss, cognition defects, cognitive impairment, amyotrophic lateral sclerosis, Alzheimer's Disease, Parkinson's Disease, Huntington's Disease, mood disorders (such as, for example, depression and bipolar disorder), substance abuse, and schizophrenia. Neurodegeneration refers to the progressive loss of structure or function of neurons, including death of neurons.

The term "sample" as used herein includes any biological fluid or issue, such as whole blood, serum, muscle, saliva, urine, synovial fluid, bone marrow, cerebrospinal fluid, nasal secretions, sputum, amniotic fluid, bronchoalveolar lavage fluid, lung tissue, peripheral blood mononuclear cells, total white blood cells, lymph node cells, spleen cells, tonsil cells, or skin, or a combination thereof. In some aspects, a sample is blood or a fraction thereof. Samples can be obtained by any means known in the art.

The term "specific" or "specifically binds" generally refers to when a compound binds a polypeptide or other target more readily than it would bind to another polypeptide or target. According to this definition, an inhibitor "specifically binds" to an HDAC isoform when it binds to that HDAC isoform more readily than it would bind to another HDAC isoform.

The terms "subject" or "patient" as used herein refer to any subject, particularly a mammalian subject, for whom diagnosis, prognosis, or therapy of a disease or disorder is desired. As used herein, the terms "subject" or "patient" include any human or nonhuman animal. The term "nonhuman animal" includes all vertebrates, e.g., mammals and non-mammals, such as nonhuman primates, sheep, dogs, cats, horses, cows, bears, chickens, amphibians, reptiles, and rodents.

As used herein the terms "treat," "treatment," or "treatment of" (e.g., in the phrase "treating a patient having a disease or disorder") refers to reducing the potential for a disease or disorder, reducing the occurrence of the disease or disorder, and/or a reduction in the severity of the disease or disorder, preferably, to an extent that the subject no longer suffers discomfort and/or altered function due to it (for example, a relative reduction in symptoms when compared to untreated patients). For example, treating can refer to the ability of a therapy when administered to a subject, to prevent a disease or disorder from occurring and/or to cure or to alleviate disease symptoms, signs, or causes. Treating also refers to mitigating or decreasing at least one clinical symptom and/or inhibition or delay in the progression of the condition and/or prevention or delay of the onset of a disease or illness. Thus, the terms "treat," "treating," or "treatment of" (or grammatically equivalent terms) refer to both prophylactic and therapeutic treatment regimes. In some aspects, the term "treating" refers to inhibiting or reducing HDAC activity or levels in a patient in need thereof.

A "therapeutically effective" or "effective" amount as used herein is an amount of a therapeutic agent that provides some improvement or benefit to a subject having a disease or disorder. Thus, a "therapeutically effective" amount is an amount that provides some alleviation, mitigation, and/or decrease in at least one clinical symptom of the disease or disorder. Clinical symptoms associated with the diseases and disorders that can be treated by the methods and systems of the disclosure are well known to those skilled in the art. In some embodiments, "therapeutically effective" amount is an amount that provides some alleviation, mitigation, and/or decrease in at least one clinical symptom of the disease or disorder. Clinical symptoms associated with the disease or disorder that can be treated by the methods and systems of the disclosure are well known to those skilled in the art. Further, those skilled in the art will appreciate that the therapeutic effects need not be complete or curative, as long as some benefit is provided to the subject. In some aspects, a "therapeutically effective" or "effective" amount as used herein refers to an amount of a compound or a composition comprising a compound, which is effective, upon single or multiple dose administrations to a subject, in treating a cell, or curing, alleviating, relieving or improving a symptom of the disorder in a subject. An effective amount of the compound or composition may vary according to the application. In the context of treating a disorder, an effective amount may depend on factors such as the disease state, age, sex, and weight of the individual, and the ability of the compound to elicit a desired response in the individual. As an example, an effective amount of a compound is an amount that produces a statistically significant change in a given parameter as compared to a control, such as in cells (e.g., a culture of cells) or a subject not treated with the compound. In some aspects, the term "therapeutically effective" or "effective" refers to an amount of a therapeutic agent that is capable of reducing HDAC activity or levels in a patient in need thereof.

As used herein, a "sufficient amount" or "an amount sufficient to" achieve a particular result in a patient having a disease or disorder refers to an amount of a therapeutic agent (e.g., a compound) that is effective to produce a desired effect, which is optionally a therapeutic effect (i.e., by administration of a therapeutically effective amount). In some aspects, such particular result is a reduction or inhibition of HDAC activity or levels in a patient in need thereof.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The terms "a" (or "an"), as well as the terms "one or more" and "at least one" can be used interchangeably herein. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2) HISTONE DEACETYLASES (HDACS)

Acetylation regulates many protein functions such as protein-protein interactions, DNA recognition, and protein stability, and acts as a signaling mechanism that is similar to phosphorylation. Histone acetylation and deacetylation in eukaryotic cells is delicately maintained by histone acetyltransferases (HATs) and histone deacetylases (HDACs). These enzymes are responsible for the modifications to chromatin structures and regulation of transcription. In general, HAT activity leads to an increase in gene transcription through the opening of the chromatin framework by adding acetyl groups. HDACs catalyze the removal of the acetyl groups on lysine residues located on the $NH_2$ terminal tails of core histones, which restores the positive charge of the lysine residue, enabling the lysine residue to interact with negatively charged phosphate in the DNA backbone, and leads to changes in gene expression by chromatin condensation. As a result, inhibition of HDAC activity can result in a general hyperacetylation of histones, which is followed by relaxation of the DNA conformation. These posttranslational modifications are essential for the regulation of many cellular processes. Inhibition of HDAC activity can result in increased transcription, decreased transcription, reactivation, inactivation, de-repression, or repression of various genes through changes in DNA conformation.

There are 18 known human HDACs that are grouped into four classes based on their size, number of catalytic sites, subcellular localization, and sequence homology to yeast counterparts. Class I (HDACs 1, 2, 3, and 8), class IIA (HDACs 4, 5, 7, and 9), class IIB (HDACs 6 and 10), and class IV (HDAC 11) are the $Zn^{2+}$-dependent enzymes. Class III proteins called sirtuins (SIRTs 1-7) are defined by their dependency on the coenzyme, electron transporter, $NAD^+$. HDAC1, HDAC2, and HDAC8 may act as transcription corepressors. The class I HDACs are predominantly located in the nucleus, while class II HDACs are in the nucleus and cytoplasm. Class I HDACs are widely expressed in most cells, whereas class II and IV show various degrees of tissue specificity. $Zn^{2+}$-dependent HDACs, including class I and class II enzymes, are related to tumorigenesis and development and are highly expressed in numerous types of cancers such as prostate cancer, colorectal cancer, gastric cancer, pancreatic cancer, and hepatocellular carcinoma.

Suitable polypeptide sequences of HDACs and the polynucleotides encoding the polypeptide sequences are known by those of skill in the art. HDAC1 may comprise a polypeptide of an amino acid sequence according to GenBank Accession No. NM_004964. HDAC2 may comprise a polypeptide of an amino acid sequence according to GenBank Accession No. Q92769 or NM_001527. HDAC3 may comprise a polypeptide of an amino acid sequence according to GenBank Accession No. NM_003883. HDAC4 may comprise a polypeptide of an amino acid sequence according to GenBank Accession No. NM_006037. HDAC5 may comprise a polypeptide of an amino acid sequence according to GenBank Accession No. NM_005474. HDAC6 may comprise a polypeptide of an amino acid sequence according to GenBank Accession No. NM_006044. HDAC7 may comprise a polypeptide of an amino acid sequence according to GenBank Accession No. AY302468. HDAC8 may comprise a polypeptide of an amino acid sequence according to GenBank Accession No. NM_018486. HDAC9 may comprise a polypeptide of an amino acid sequence according to GenBank Accession No. NM_178423. HDAC10 may comprise a polypeptide of an amino acid sequence according to GenBank Accession No. NM_032019. HDAC111 may comprise a polypeptide of an amino acid sequence according to GenBank Accession No. NM_024827.

3) HDAC INHIBITORS

Provided herein are novel HDAC inhibitors. HDAC inhibitors may include polypeptides, polynucleotides, or compounds that reduce or inhibit the activity or level of a HDAC. An HDAC inhibitor may inhibit all HDAC isoforms. An HDAC inhibitor may inhibit at least one HDAC isoform. An HDAC inhibitor may inhibit multiple or a combination of HDAC isoforms. An HDAC inhibitor may inhibit a class I HDAC (HDAC1, HDAC2, HDAC3, or HDAC8) or a combination thereof. An HDAC inhibitor may inhibit a class II HDAC (HDAC4, HDAC5, HDAC6, HDAC7, HDAC9, or HDAC10) or a combination thereof. An HDAC inhibitor may inhibit a class IIA HDAC (HDAC4, HDA 5, HDAC7, or HDAC9) or a combination thereof. An HDAC inhibitor may inhibit a class IIB HDAC (HDAC6 or HDAC10) or a combination thereof. An HDAC inhibitor may inhibit a class IV HDAC (HDAC11). An HDAC inhibitor may inhibit HDAC1. An HDAC inhibitor may inhibit HDAC2. An HDAC inhibitor may inhibit HDAC3. An HDAC inhibitor may inhibit HDAC4. An HDAC inhibitor may inhibit HDAC5. An HDAC inhibitor may inhibit HDAC6. An HDAC inhibitor may inhibit HDAC 7. An HDAC inhibitor may inhibit HDAC8. An HDAC inhibitor may inhibit HDAC9. An HDAC inhibitor may inhibit HDAC10. An HDAC inhibitor may inhibit HDAC 11. In some embodiments, the HDAC inhibitor inhibits a class I HDAC. In some embodiments, the HDAC inhibitor inhibits HDAC1. In some embodiments, the HDAC inhibitor inhibits HDAC1 and HDAC2. In some embodiments, the HDAC inhibitor inhibits HDAC1, HDAC2, and HDAC3.

An HDAC inhibitor may be specific for at least one or a combination of HDAC isoforms. Specificity for at least one or a combination of HDAC isoforms may result in more effective targeting to particular cells or targets, enhanced therapeutic activity, reduced toxicity, and/or reduced side effects than other therapies. In some embodiments an HDAC inhibitor may be specific for HDAC1 and HDAC2. In some embodiments an HDAC inhibitor may be specific for HDAC1. In some embodiments an HDAC inhibitor may be specific for HDAC2.

In some embodiments, an HDAC inhibitor comprises a compound of Formula I or Formula II.

a) Compounds of Formula I and II

HDAC inhibitors generally adopt a "monkey wrench" scaffold in which a C5 (or C6 in some cases) linker connects a cap region and a zinc-binding group (ZBG). The cap is relatively flexible and mediates surface-to-surface interactions between drug and protein targets; the ZBG may be important for HDAC inhibitory activity by chelating a zinc ion in the catalytic center of HDACs. The compounds detailed herein were designed to keep a ZBG (the thiol group from FK228/TDPs) and the C5 linker (FIG. 1). As detailed in Example 1, the incorporation of acidic groups into the smaller fragments of the natural compound TDF1 not only improved the solubility compared to the parent compound but interestingly added more potency than SAHA.

In some embodiments, an HDAC inhibitor comprises a compound according to Formula I:

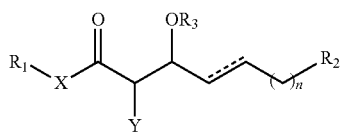

(I)

and stereoisomers and salts thereof;
wherein
X is NH or O or a direct bond;
$R_1$ is H, $C_{1-10}$ alkyl, aryl, heteroaryl, or —NH—$CHR_a$C(O)—$OR_4$;
$R_a$ is an amino acid side chain, H, $C_{1-10}$ alkyl, $C_{1-10}$ heteroalkyl, aryl, or heteroaryl;
$R_4$ is H, $C_{1-10}$ alkyl, heteroaryl or aryl;
$R_2$ is SH, SeH, or C(O)NHOH or the compound can form a disulfide or diselenide dimer at the $R_2$ position;
$R_3$ is H, $C_{1-10}$ alkyl, heteroaryl, aryl or —C(O)$R_5$;
$R_5$ is $C_{1-10}$ alkyl, heteroaryl, aryl, or —CH(N($R_N$)$_2$)(CR'R"$OR_O$);
R' is H or $C_{1-10}$ alkyl, heteroaryl or aryl;
R" is H or $C_{1-10}$ alkyl, heteroaryl or aryl;
each $R_N$ is independently H, $C_{1-10}$ alkyl, heteroaryl, or aryl;
$R_O$ is H, $C_{1-10}$ alkyl, heteroaryl or aryl;
Y is H, $C_{1-10}$ alkyl, heteroaryl, aryl, or halogen;
n is an integer from 0 to 5;

wherein if X is a direct bond, $R_1$ is —NH—$CHR_a$C(O)—$OR_4$; and
wherein the dashed bond indicates the presence of an optional double bond.

In some embodiments, an HDAC inhibitor comprises a compound according to Formula II:

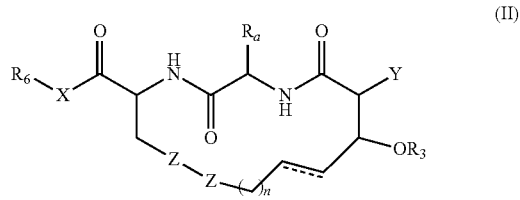

(II)

and stereoisomers and salts thereof;
wherein
Z is S or Se;
X is NH or O or a direct bond;
$R_6$ is H, $C_{1-10}$ alkyl, heteroaryl, aryl, or —NH—$CHR_a$C(O)—$OR_4$;
$R_a$ is an amino acid side chain, H, $C_{1-10}$ alkyl, $C_{1-10}$ heteroalkyl, aryl, or heteroaryl;
$R_4$ is H, $C_{1-10}$ alkyl, heteroaryl, or aryl;
$R_3$ is H, $C_{1-10}$ alkyl, heteroaryl, aryl, or —C(O)$R_5$;
$R_5$ is $C_{1-10}$ alkyl, heteroaryl, aryl, —CH(N($R_N$)$_2$)(CR'R"$OR_O$);
R' is H, $C_{1-10}$ alkyl, heteroaryl, or aryl;
R" is H, $C_{1-10}$ alkyl, heteroaryl, or aryl;
each $R_N$ is independently H, $C_{1-10}$ alkyl, heteroaryl, or aryl;
$R_O$ is H or $C_{1-10}$ alkyl, heteroaryl, or aryl;
Y is H, $C_{1-10}$ alkyl, heteroaryl, aryl, or halogen;
wherein if X is a direct bond, $R_6$ is —NH—$CHR_a$C(O)—$OR_4$;
n is an integer from 0 to 5; and
wherein the dashed bond indicates the presence of an optional double bond.

In some embodiments, X is a direct bond and $R_1$ or $R_6$ is —NH—$CHR_a$C(O)—$OR_4$. In other embodiments, X is NH. In other embodiments, X is O.

In some embodiments, $R_a$ is H, $C_{1-10}$ alkyl, aryl, heteroaryl, or halogen. In some embodiments, $R_a$ is an amino acid side chain. In some embodiments, $R_a$ is an aliphatic amino acid side chain, hydroxyl- or sulfer- or selenium-containing amino acid side chain, cyclic amino acid side chain, aromatic amino acid side chain, or basic amino acid side chain. In some embodiments, $R_a$ is an aliphatic amino acid side chain or a hydroxyl- or sulfer- or selenium-containing amino acid side chain. In some embodiments, $R_a$ is glycine side chain, alanine side chain, isoleucine side chain, leucine side chain, serine side chain, valine side chain, or methionine side chain. In some embodiments, $R_a$ is isoleucine side chain, serine side chain, valine side chain, or methionine side chain.

In some embodiments, $R_1$ is H. In other embodiments, $R_1$ is $C_{1-10}$ alkyl.

In some embodiments, $R_2$ is SH. In some embodiments, $R_2$ is SeH. In some embodiments, the compound of Formula I forms a disulfide dimer at the $R_2$ position. In some embodiments, the compound of Formula I forms a diselenide dimer at the $R_2$ position.

In some embodiments, $R_3$ is H. In some embodiments, $R_3$ is —C(O)$R_5$. In some embodiments, $R_5$ is —CH(N($R_N$)$_2$)

(CR'R"OR$_O$). In some embodiments, at least one R$_N$ is H. In some embodiments, both R$_N$ are H. In some embodiments, R$_O$ is H. In some embodiments, one of R' and R" is H and the other is C$_{1-10}$ alkyl, such as methyl. In some embodiments, both R' and R" are H.

In some embodiments, R$_4$ is H. In some embodiments, R$_4$ is C$_{1-10}$ alkyl, such as methyl or ethyl.

In some embodiments, Y is H.

In some embodiments, Z is S. In some embodiments, Z is Se.

In some embodiments, the optional double bond is present.

Exemplary HDAC inhibitors are shown in Table 1.

TABLE 1

Structures of HDAC inhibitors.

| Compound Name | Compound Structure |
|---|---|
| FK228 (ISTODAX ®) | 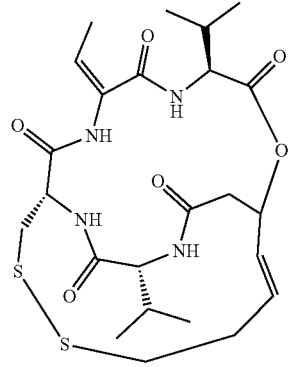 [SMILES: C/C=C1/NC(=O)[C@H]2CSSCC/C=C/C(CC(=O)N[C@H](C(C)C)C(=O)N2)OC(=O)[C@H](C(C)C)NC1=O] |
| SAHA (ZOLINZA ®) | 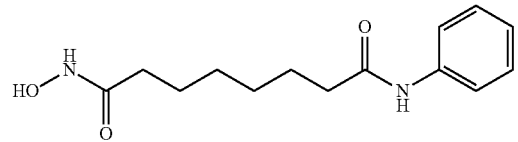 [SMILES: O=C(CCCCCCC(=O)Nc1ccccc1)NO] |
| Thailandepsin A (TDP-A) | 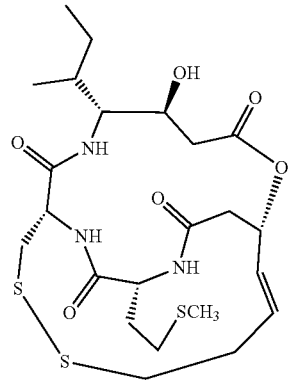 [SMILES: CCC(C)[C@H]1NC(=O)[C@H]2CSSCC/C=C/[C@H](CC(=O)N[C@H](CCSC)C(=O)N2)OC(=O)C[C@@H]1O] |
| Thailandepsin B (TDP-B) | 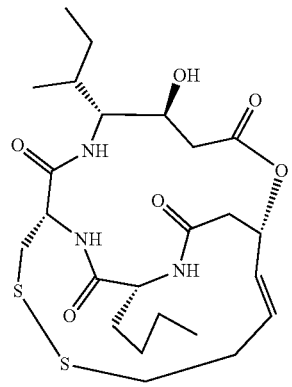 [SMILES: CCCC[C@H]1NC(=O)C[C@H]2/C=C/CCSSC[C@@H](NC1=O)C(=O)N[C@H](C(C)CC)[C@@H](O)CC(=O)O2] |

TABLE 1-continued
Structures of HDAC inhibitors.
| Compound Name | Compound Structure |
|---|---|
| TDC1 | 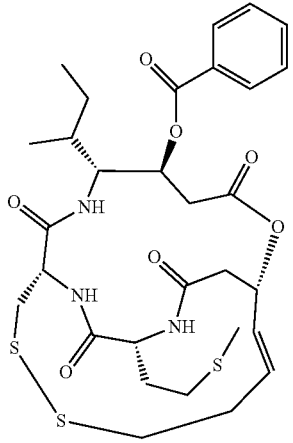 [SMILES: CCC(C)[C@H]1NC(=O)[C@H]2CSSCC/C=C/[C@H](CC(=O)N[C@H](CCSC)C(=O)N2)OC(=O)C[C@@H]1OC(=O)c1ccccc1] |
| TDC2 | 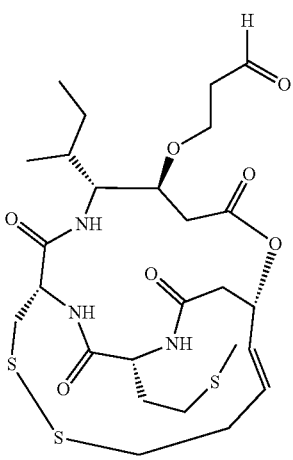 [SMILES: CCC(C)[C@H]1NC(=O)[C@H]2CSSCC/C=C/[C@H](CC(=O)N[C@H](CCSC)C(=O)N2)OC(=O)C[C@@H]1OCCC=O] |
| TDC3 | 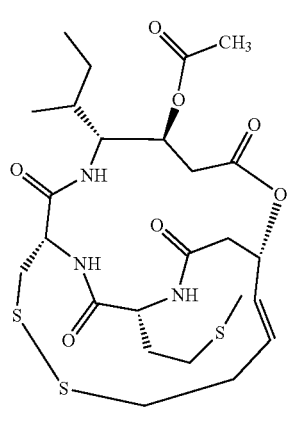 [SMILES: CCC(C)[C@H]1NC(=O)[C@H]2CSSCC/C=C/[C@H](CC(=O)N[C@H](CCSC)C(=O)N2)OC(=O)C[C@@H]1OC(C)=O] |
| TDF3 = Cpd1 | 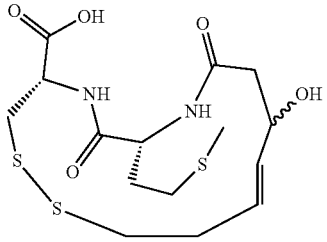 [SMILES: CSCC[C@H]1NC(=O)CC(O)/C=C/CCSSC[C@H](C(=O)O)NC1=O] |

TABLE 1-continued
Structures of HDAC inhibitors.
| Compound Name | Compound Structure |
|---|---|
| TDF3m = Cpd1' | 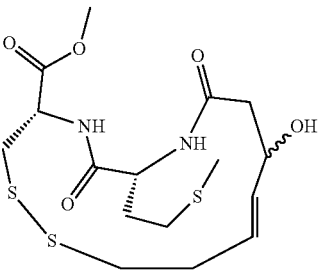 [SMILES: COC(=O)[C@H]1CSSCC/C=C/C(O)CC(=O)N[C@H](CCSC)C(=O)N1] |
| TDF2 = Cpd2 | 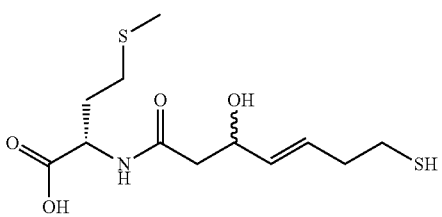 [SMILES: CSCC[C@H](NC(=O)CC(O)/C=C/CCS)C(=O)O] |
| TDF2m = Cpd2' | 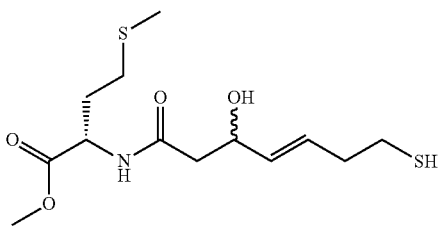 [SMILES: COC(=O)[C@H](CCSC)NC(=O)CC(O)/C=C/CCS] |
| TDF1 = Cpd3 | 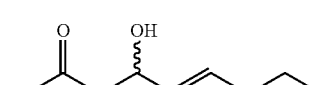 |
| TDF1t = Cpd3' | 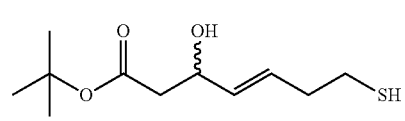 |
| TDF4 = Cpd4 | 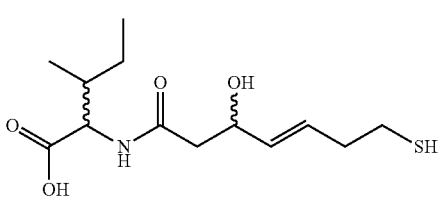 [SMILES: CCC(C)C(NC(=O)CC(O)/C=C/CCS)C(=O)O] |
| TDF4m = Cpd4' | 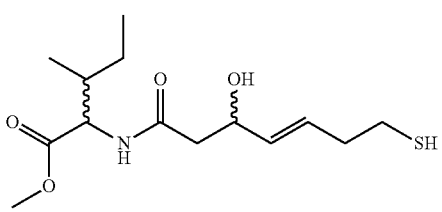 [SMILES: CCC(C)C(NC(=O)CC(O)/C=C/CCS)C(=O)OC] |

TABLE 1-continued

Structures of HDAC inhibitors.

| Compound Name | Compound Structure |
|---|---|
| TDF5 = Cpd5 | 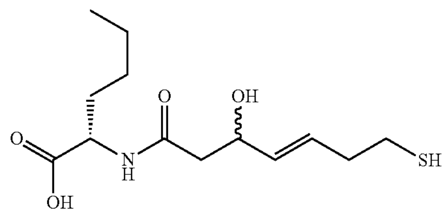 [SMILES: CCCC[C@H](NC(=O)CC(O)/C=C/CCS)C(=O)O] |
| TDF5m = Cpd5' | 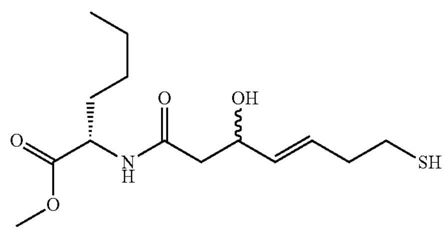 [SMILES: CCCC[C@H](NC(=O)CC(O)/C=C/CCS)C(=O)OC] |
| TDF6 = Cpd6 | 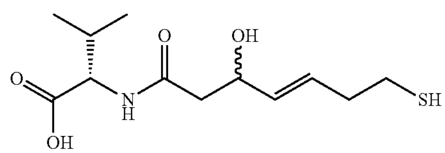 [SMILES: CC(C)[C@H](NC(=O)CC(O)/C=C/CCS)C(=O)O] |
| TDF6m = Cpd6' | 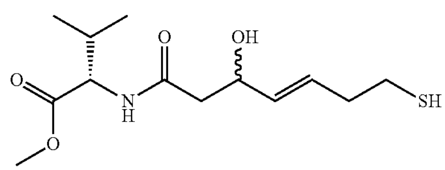 [SMILES: COC(=O)[C@@H](NC(=O)CC(O)/C=C/CCS)C(C)C] |
| TDF7 = Cpd7 | 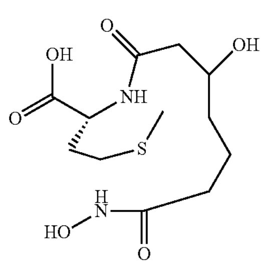 [SMILES: CSCC[C@@H](NC(=O)CC(O)CCCC(=O)NO)C(=O)O] |
| TDF7t = Cpd7' | 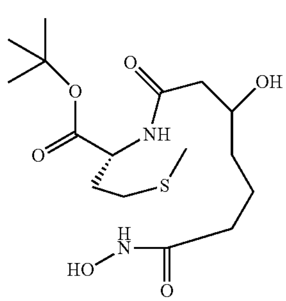 [SMILES: CSCC[C@@H](NC(=O)CC(O)CCCC(=O)NO)C(=O)OC(C)(C)C] |

TABLE 1-continued
Structures of HDAC inhibitors.
| Compound Name | Compound Structure |
|---|---|
| TDF8 = Cpd8 | 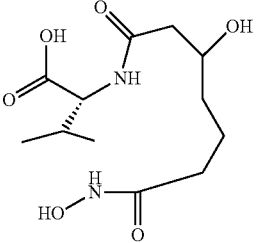 [SMILES: CC(C)[C@@H](NC(=O)CC(O)CCCC(=O)NO)C(=O)O] |
| TDF8m = Cpd8' | 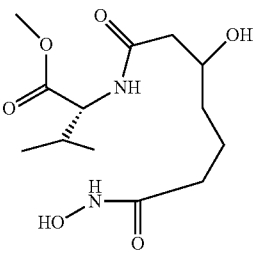 [SMILES: COC(=O)[C@H](NC(=O)CC(O)CCCC(=O)NO)C(C)C] |
| TDF9 = Cpd9 | 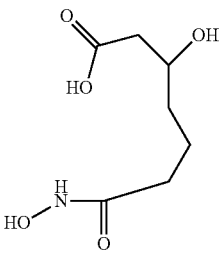 [SMILES: O=C(O)CC(O)CCCC(=O)NO] |
| TDF9t = Cpd9' | 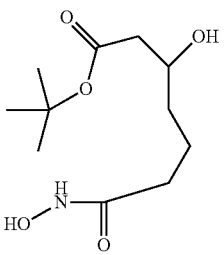 [SMILES: CC(C)(C)OC(=O)CC(O)CCCC(=O)NO] |
| Cpd10 | 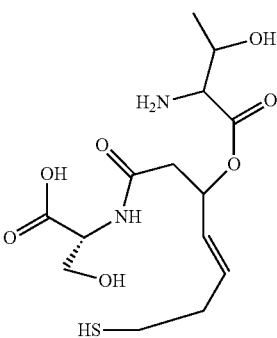 [SMILES: CC(O)C(N)C(=O)OC(/C=C/CCS)CC(=O)N[C@H](CO)C(=O)O] |

TABLE 1-continued

Structures of HDAC inhibitors.

| Compound Name | Compound Structure |
| --- | --- |
| Cpd10' | (structure) |
| Cps11 | (structure) |
| Cpd11' | (structure) |
| Cpd12 | (structure) |
| Cpd12' | (structure) |

In some embodiments, the HDAC inhibitor is selected from the following compounds:
TDC1
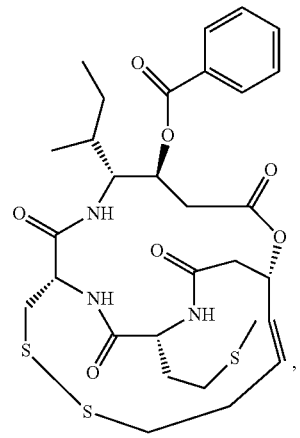
TDC2
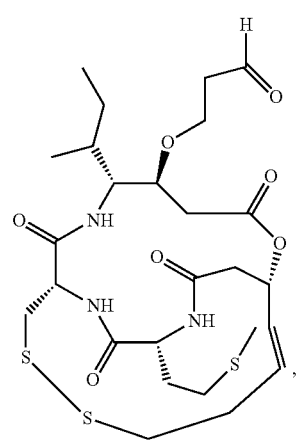
TDC3
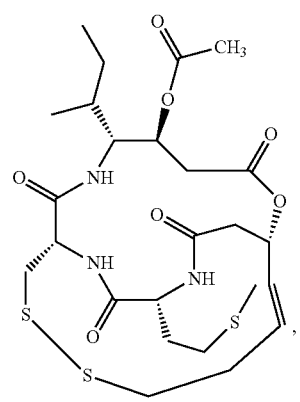
Cpd1
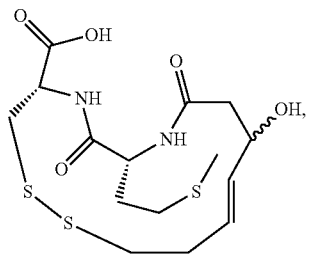
Cpd1'
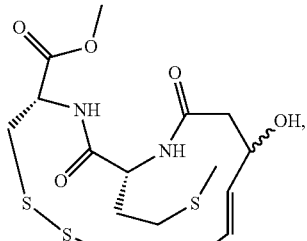
Cpd2
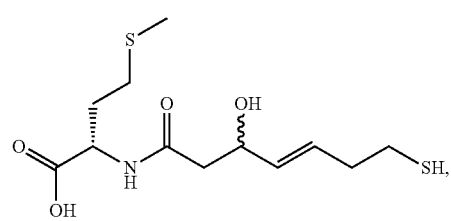
Cpd2'
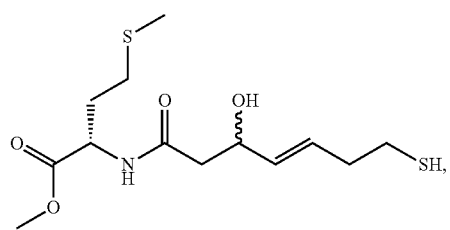
Cpd3
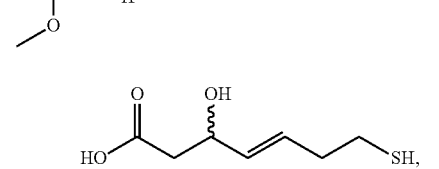
Cpd3'
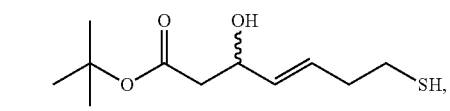
Cpd4
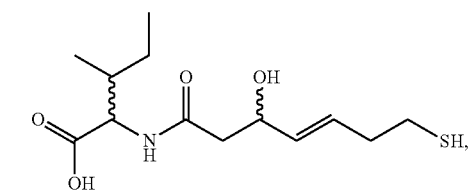
Cpd4'
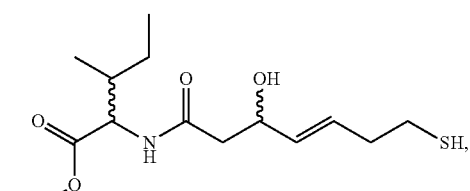
Cpd5
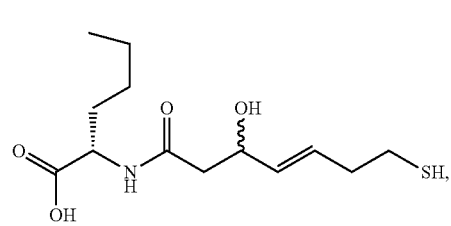

Cpd5'
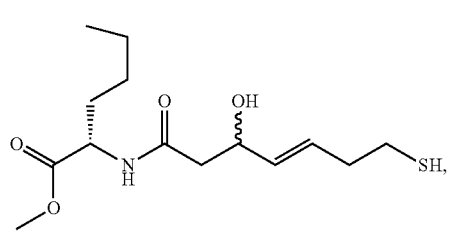
Cpd6
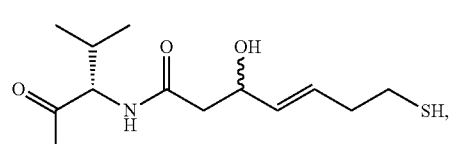
Cpd6'
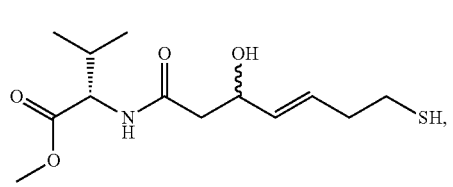
Cpd7
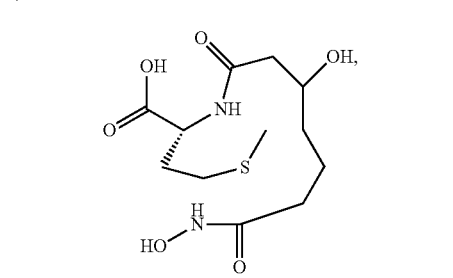
Cpd7'
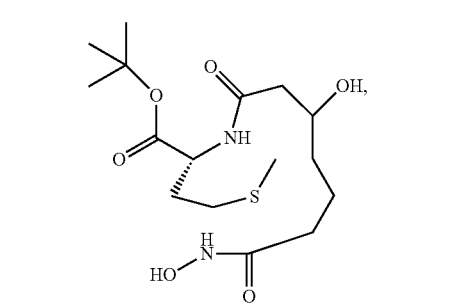
Cpd8
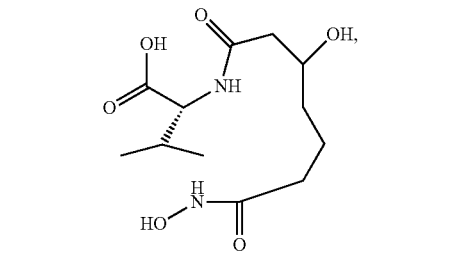
Cpd8'
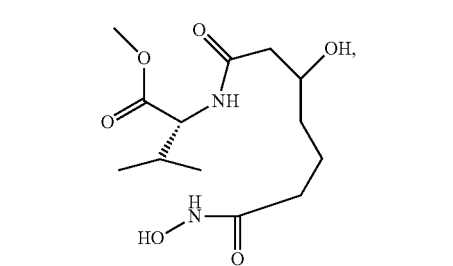
Cpd9
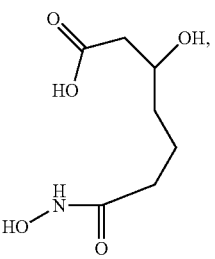
Cpd9'
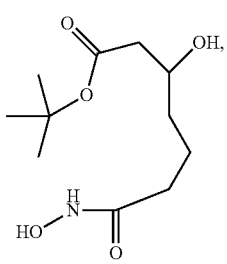
Cpd10
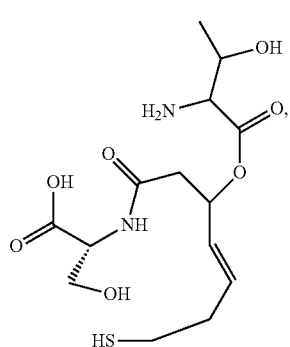
Cpd10'
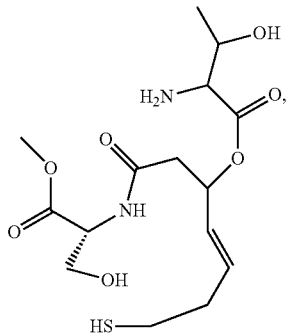
Cpd11
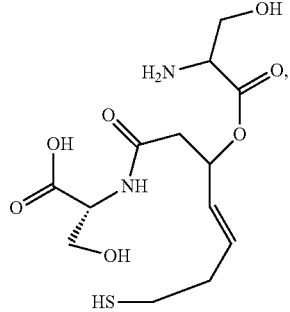

-continued

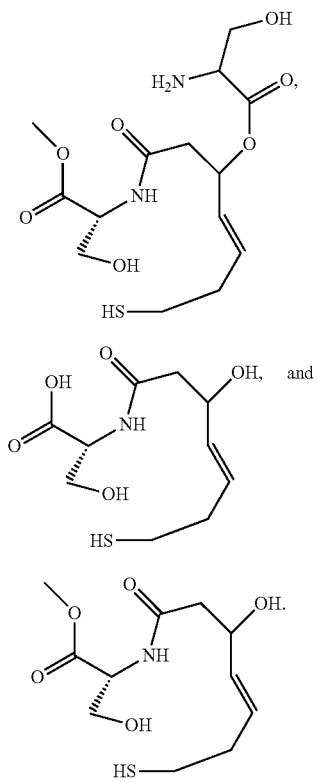

Cpd11'

Cpd12

Cpd12'

In some embodiments, the HDAC inhibitor does not include the following compound:

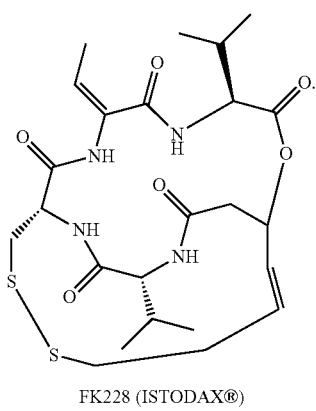 [SMILES: C/C=C1/NC(=O)[C@H]2CSSCC/C=C/C(CC(=O)N[C@H](C(C)C)C(=O)N2)OC(=O)[C@H](C(C)C)NC1=O]

FK228 (ISTODAX®)

In some embodiments, the HDAC inhibitor does not include the following compound:

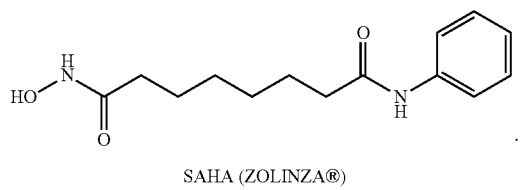 [SMILES: O=C(CCCCCCC(=O)Nc1ccccc1)NO]

SAHA (ZOLINZA®)

In some embodiments, the HDAC inhibitor does not include the following compound:

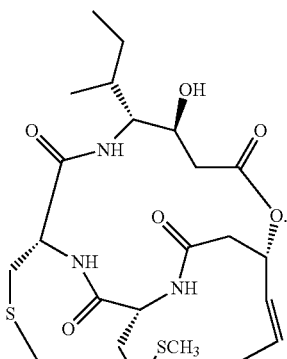

TDP-A

In some embodiments, the HDAC inhibitor does not include the following compound:

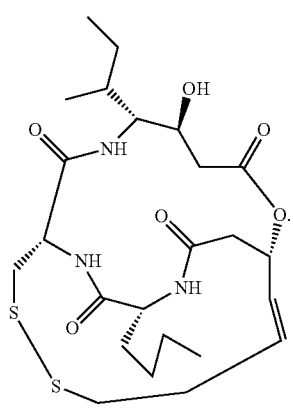

TDP-B

In some embodiments, the HDAC inhibitor does not include the following compound:

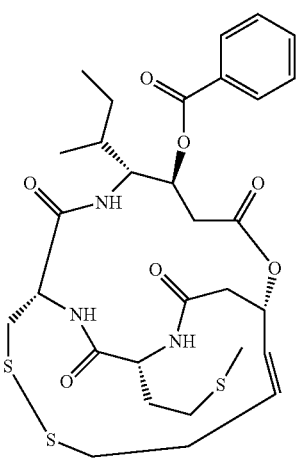

TDC1

In some embodiments, the HDAC inhibitor does not include the following compound:

TDC2

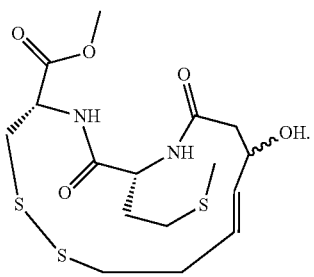

In some embodiments, the HDAC inhibitor does not include the following compound:

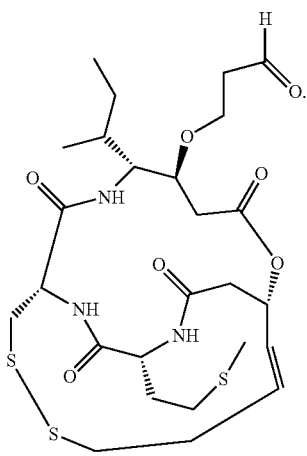

In some embodiments, the HDAC inhibitor does not include the following compound:

Cpd2

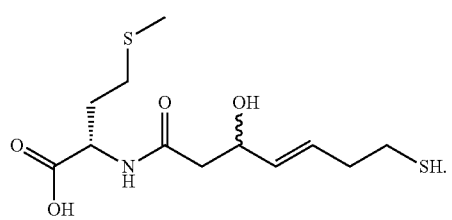

In some embodiments, the HDAC inhibitor does not include the following compound:

TDC3

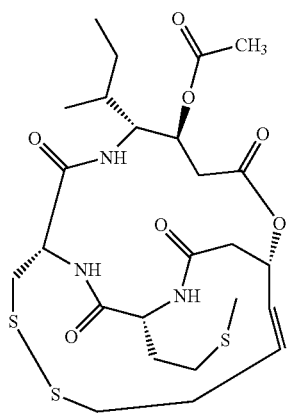

Cpd2'

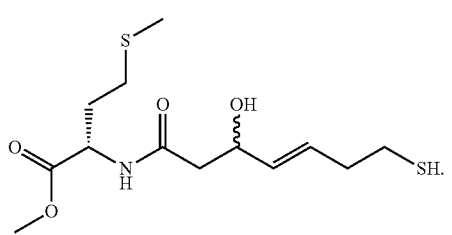

In some embodiments, the HDAC inhibitor does not include the following compound:

In some embodiments, the HDAC inhibitor does not include the following compound:

Cpd3

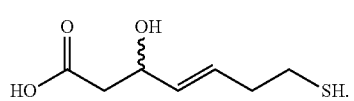

In some embodiments, the HDAC inhibitor does not include the following compound:

Cpd1

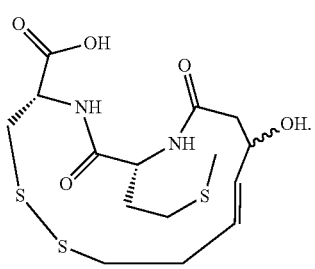

Cpd3'

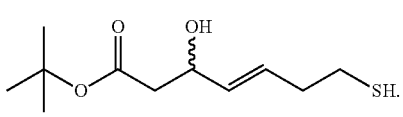

In some embodiments, the HDAC inhibitor does not include the following compound:

In some embodiments, the HDAC inhibitor does not include the following compound:

Cpd4

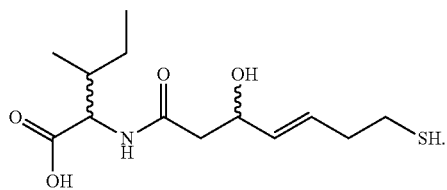

In some embodiments, the HDAC inhibitor does not include the following compound:

Cpd4′

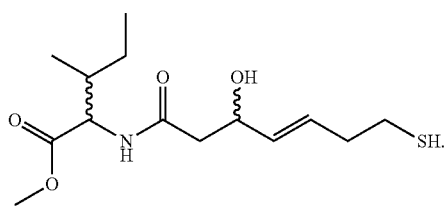

In some embodiments, the HDAC inhibitor does not include the following compound:

Cpd5

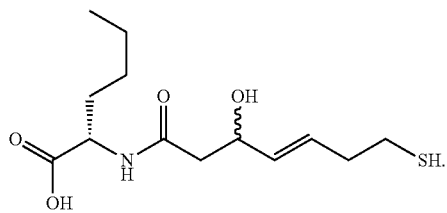

In some embodiments, the HDAC inhibitor does not include the following compound:

Cpd5′

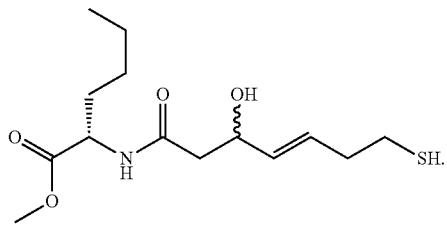

In some embodiments, the HDAC inhibitor does not include the following compound:

Cpd6

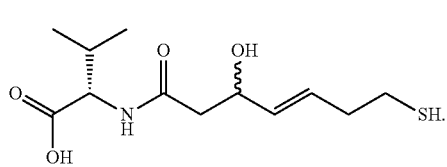

In some embodiments, the HDAC inhibitor does not include the following compound:

Cpd6′

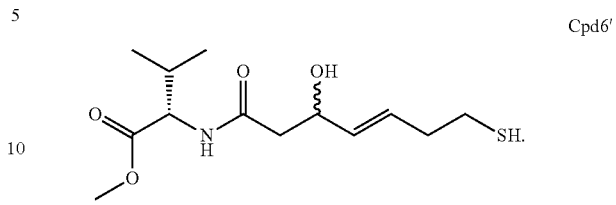

In some embodiments, the HDAC inhibitor does not include the following compound:

Cpd7

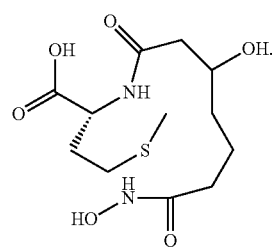

In some embodiments, the HDAC inhibitor does not include the following compound:

Cpd7′

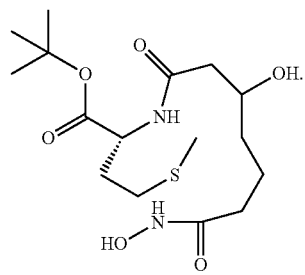

In some embodiments, the HDAC inhibitor does not include the following compound:

Cpd8

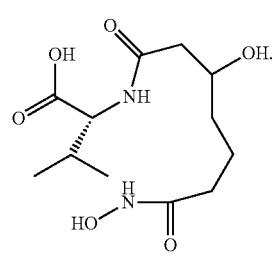

In some embodiments, the HDAC inhibitor does not include the following compound:

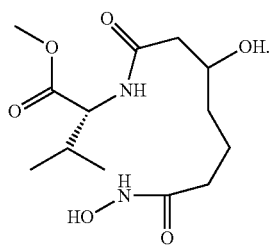

Cpd8'

In some embodiments, the HDAC inhibitor does not include the following compound:

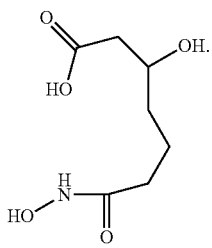

Cpd9

In some embodiments, the HDAC inhibitor does not include the following compound:

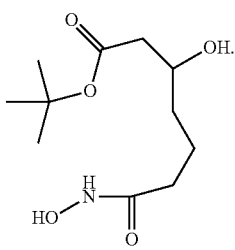

Cpd9' b) Isomers

Certain compounds may exist in one or more particular geometric, optical, enantiomeric, diastereomeric, epimeric, atropic, stereoisomer, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; a- and β-forms; axial and equatorial forms; boat-, chair-, twist-, envelope-, and half chair-forms; and combinations thereof, hereinafter collectively referred to as "isomers" (or "isomeric forms").

In one embodiment, a compound described herein may be an enantiomerically enriched isomer of a stereoisomer described herein. For example, the compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enantiomer, when used herein, refers to either of a pair of chemical compounds whose molecular structures have a mirror-image relationship to each other.

In one embodiment, a preparation of a compound disclosed herein is enriched for an isomer of the compound having a selected stereochemistry, e.g., R or S, corresponding to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In one embodiment, a composition described herein includes a preparation of a compound disclosed herein that is enriched for a structure or structures having a selected stereochemistry, e.g., R or S, at a selected stereocenter. Exemplary R/S configurations can be those provided in an example described herein.

An "enriched preparation," as used herein, is enriched for a selected stereoconfiguration of one, two, three or more selected stereocenters within the subject compound. Exemplary selected stereocenters and exemplary stereoconfigurations thereof can be selected from those provided herein, e.g., in an example described herein. By enriched is meant at least 60%, e.g., of the molecules of compound in the preparation have a selected stereochemistry of a selected stereocenter. In an embodiment it is at least 65%, 70%, 75%, 80%, 85%, 90%, 95%, 96%, 97%, 98%, or 99%. Enriched refers to the level of a subject molecule(s) and does not connote a process limitation unless specified.

Compounds may be prepared in racemic form or as individual enantiomers or diastereomers by either stereo-specific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

Except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_3$-alkyl or propyl includes n-propyl and iso-propyl; C$_4$-alkyl or butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hydroxyazo, and nitro/aci-nitro.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

c) Salt Forms

A compound described herein can be in the form of a salt, e.g., a pharmaceutically acceptable salt. The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds or separately by reacting a compound with a suitable acid or base, depending on the particular substituents found on the compounds described herein. Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure. Examples of pharmaceutically acceptable salts are discussed in Berge et al, 1977, "Pharmaceutically Acceptable Salts." *J. Pharm. Sci. Vol.* 66, pp. 1-19.

Representative acid addition salts can be prepared using various suitable acids for example, including, but are not limited to, acetic, adipic, alginic, citric, aspartic, benzoic, benzenesulfonic, butyric, camphoric, camphorsulfonic, carbonic, digluconic, glycerophosphoric, heptanoic, hexanoic, fumaric, hydrochloric, hydrobromic, hydroiodic, 2-hydroxyethansulfonic (isethionic), lactic, maleic, methanesulfonic, nicotinic, 2-naphthalenesulfonic, oxalic, pamoic, pectinic, persulfuric, 3-phenylpropionic, picric, pivalic, propionic, succinic, sulfuric, tartaric, thiocyanic, phosphoric, glutamatic, p-toluenesulfonic, and undecanoic acids.

Particular examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, tartaric acid, and citric acid.

Basic addition salts can be prepared in situ during the final isolation and purification of compounds by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Unless otherwise specified, a reference to a particular compound also includes salt forms thereof.

d) Chemically Protected Forms

It may be convenient or desirable to prepare, purify, and/or handle an active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999). Unless otherwise specified, a reference to a particular compound also includes chemically protected forms thereof.

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A hydroxy group may be protected as an ether (—OR) or an ester (—OC(O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(O)CH$_3$, -OAc).

An aldehyde or ketone group may be protected as an acetal (RCH(OR)$_2$) or ketal (R$_2$C(OR)$_2$), respectively, in which the carbonyl group (R$_2$C=O) is converted to a diether (R$_2$C(OR)$_2$), by reaction with, for example, a primary alcohol. The aldehyde or ketone group is readily regenerated by hydrolysis using an excess of water in the presence of acid.

An amine group may be protected, for example, as an amide (—NRC(O)R) or a urethane (—NRC(O)OR), for example, as: a methyl amide (—NHC(O)CH$_3$); a benzyloxy amide (—NHC(O)OCH$_2$C$_6$H$_5$, —NH-Cbz); as a t-butoxy amide (—NHC(O)OC(CH$_3$)$_3$, —NH-Boc); a 2-biphenyl-2-propoxy amide (—NHCO(O)C(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2-(phenylsulfonyl)ethyloxy amide (—NH-Psec); or, in suitable cases (e.g., cyclic amines), as a nitroxide radical.

A carboxylic acid group may be protected as an ester, for example, as: an alkyl ester (e.g., a methyl ester; a t-butyl ester); a haloalkyl ester (e.g., a haloalkyl ester); a trialkylsilylalkyl ester; or an arylalkyl ester (e.g., a benzyl ester; a nitrobenzyl ester); or as an amide, for example, as a methyl amide.

A thiol group may be protected as a thioether (—SR), for example, as: a benzyl thioether; or an acetamidomethyl ether (—S—$CH_2NHC(O)CH_3$).

e) Prodrugs and Other Modifications

In addition to salt forms, the present disclosure may also provide compounds that are in a prodrug form. Prodrugs of the compounds described herein are those compounds that readily undergo chemical changes under physiological conditions to provide the compounds described herein. The term "pharmaceutically acceptable prodrug" or "prodrug," as used herein, represents those prodrugs of the compounds which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the disclosure can be rapidly transformed in vivo to a parent compound, for example, by hydrolysis. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

A compound described herein can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include but are not limited to esterification with polyethylene glycols, derivatization with pivolates or fatty acid substituents, conversion to carbamates, hydroxylation of aromatic rings, and heteroatom substitution in aromatic rings.

f) Synthesis

Compounds described herein may be prepared according to a variety of methods. A representative synthesis of exemplary compounds of Formula I is illustrated in FIG. 2. The synthesis started with acrolein 1 and was converted to the trityl (triphenylmethyl) sulfur group containing α,β-unsaturated aldehyde 2 in two steps in 70% yield. The desired aldol product 3 was achieved from 2 using LDA as a base and methyl acetate as the enolate source. The methyl ester 3 was deprotected with lithium hydroxide to yield the β-hydroxy acid 4. It was treated with iodine to form disulfide products of Cpd3 and Cpd3'. A β-hydroxy acids 4 were used due to having both diastereomers available for in vivo and vitro testing. For the synthesis of Cpd1 and Cpd2, the coupling reagent PyBop (benzotriazol-1-yl-oxytripyrrolidino-phosphonium hexafluoro-phosphate) was used to control peptide bond formation and to decrease racemization. From this practical point of view, the aldol sequence is concise, providing disulfide product of Cpd2 in six steps and Cpd1 in eight steps from acrolein 1. The synthesis can routinely be performed on a multigram scale. The overall yield for disulfide products of Cpd2 and Cpd1 was 13.1% and 6.8%, respectively.

Another exemplary synthesis is shown in FIG. 3 for Cpds4-6 and Cpds4'-6'. The synthesis was started with the intermediate 4. Coupling with amino acids containing different hydrophobic R groups in the presence of PyBop provided the desired peptides. Later, the use of LiOH (hydrolysis) and deprotection procedures as described in FIG. 3 gave Cpds4-6 and Cpds4'-6'.

Figure 4A:
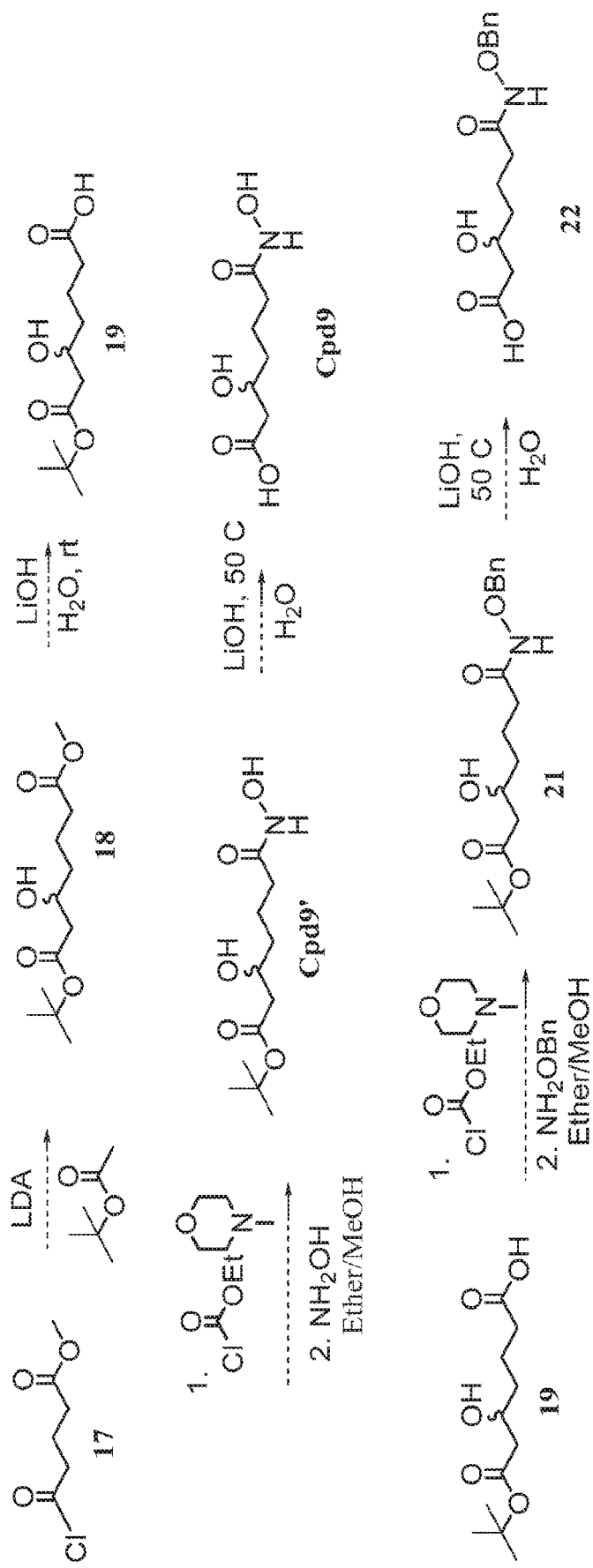
FIG. 4 is a schematic for the synthesis of compounds Cpd7, Cpd7', Cpd8, Cpd8', Cpd9, and Cpd9'.
Figure 4B:
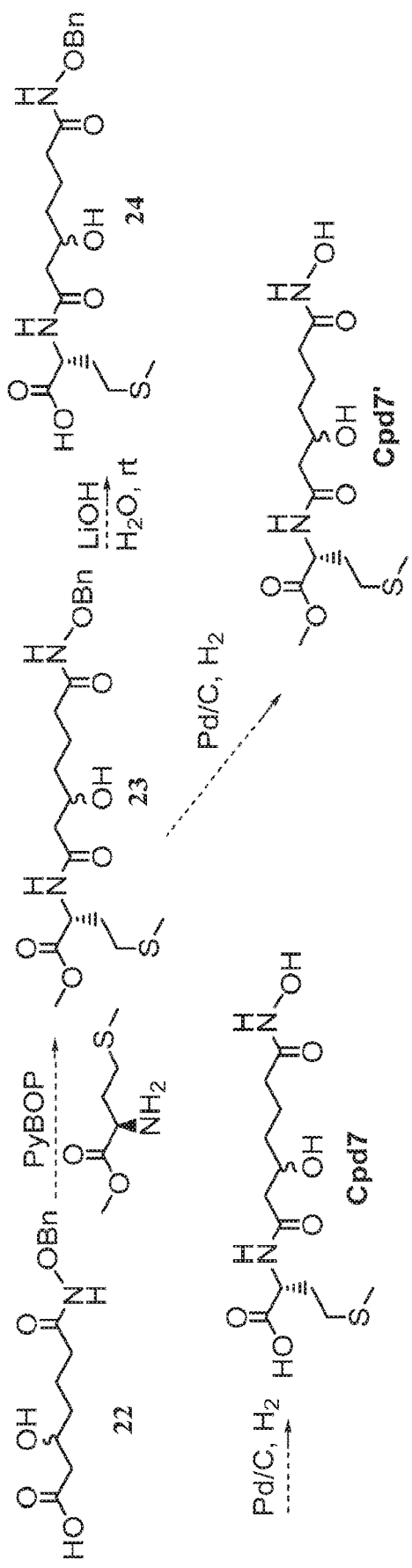
Figure 4C:
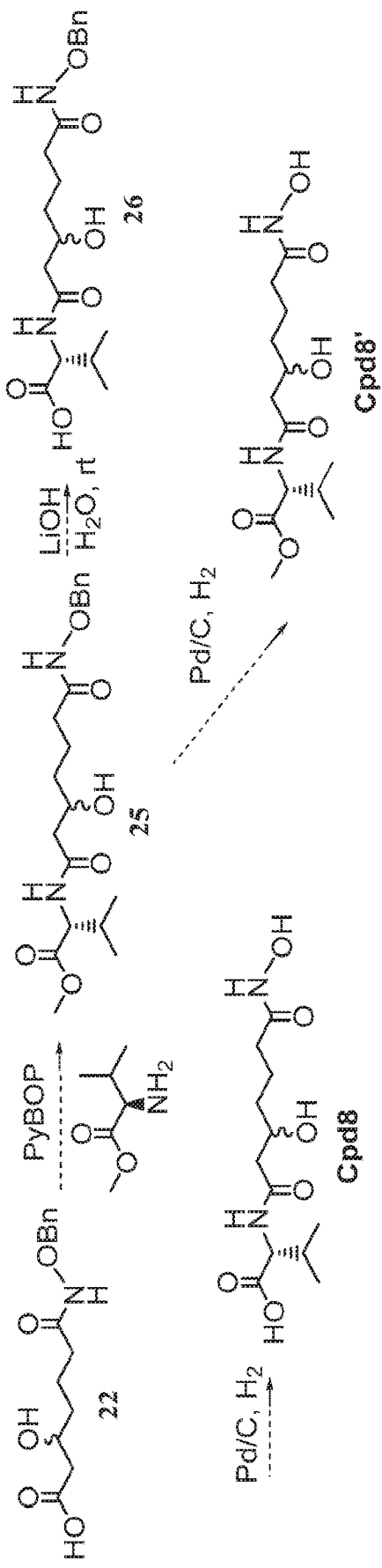
Figure 5A:
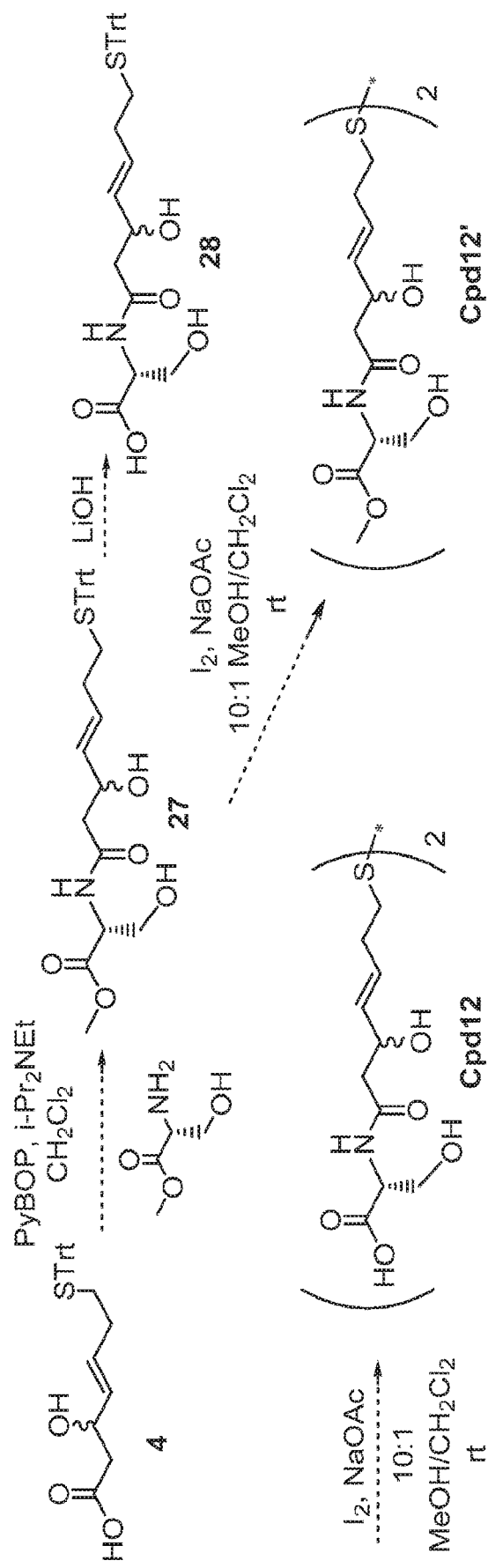
FIG. 5 is a schematic for the synthesis of compounds Cpd10, Cpd10', Cpd11, Cpd11', Cpd12, and Cpd12'.
Figure 5B:
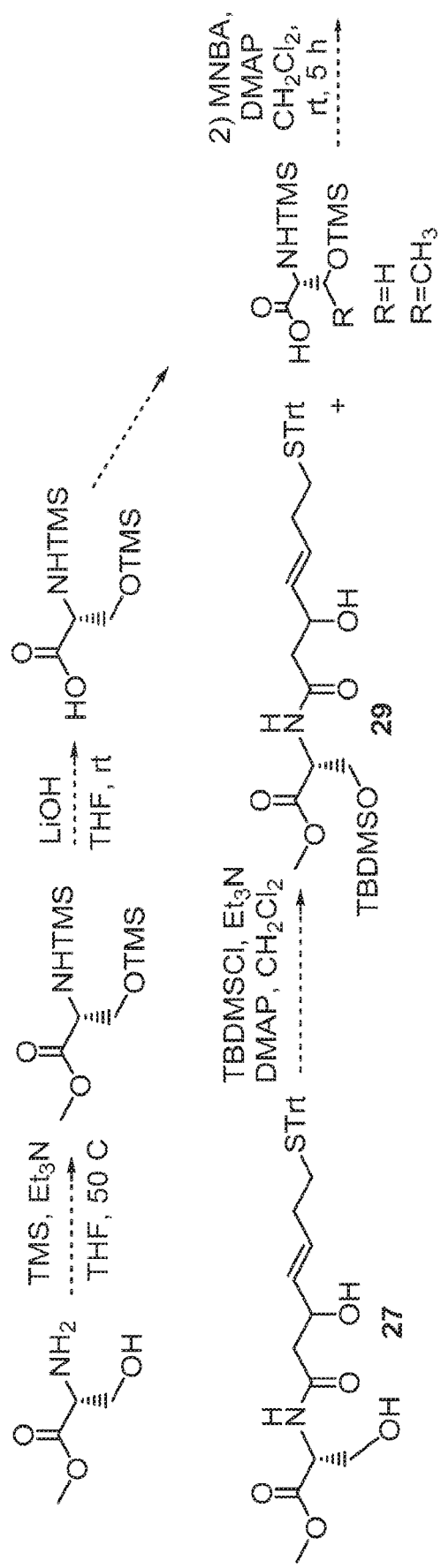
Figure 5C:
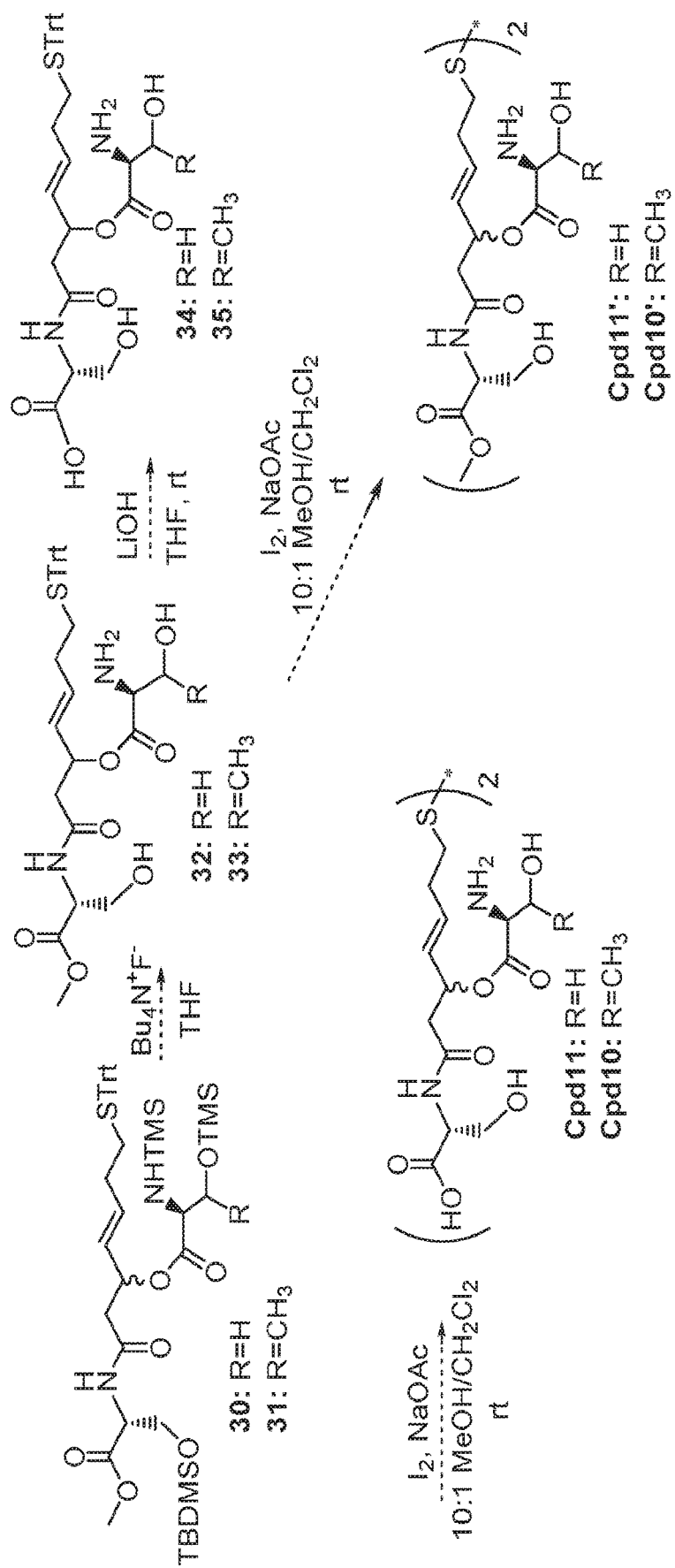

Further exemplary syntheses are shown in FIGS. 4 and 5. Here the thiol motif will be changed to hydroxamic acid to mimic the biological activity of SAHA (ZOLINZA®). In this process, the intermediate 19 is synthesized from 17 using aldol reaction and followed by hydrolysis as described before (FIG. 4). The compound 19 will be converted to hydroxamic acid Cpd9' with ethyl chloroformate in the presence of a base, followed by $NH_2OH$ (50% $H_2O$) in methanol. Hydrolysis of Cpd9' will provide Cpd 9. Next, coupling will be carried out by the same fashion as before mention with the ligand PyBop to synthesize Cpds7'-8' and Cpd7-Cpd8 respectively (FIG. 4). FIG. 5 describes the synthetic route for products Cpd10-12 and Cpd10'-12'. This synthesis will start by coupling the compound 4 (FIG. 2) with amino acid serine and other different derivatives of serine. Deprotection and hydrolysis as described before will produce the desired compounds.

As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents or Organic Synthesis, John Wiley and Sons (1995), and subsequent editions thereof.

5) COMPOSITIONS

The HDAC inhibitors as detailed herein may be present in a composition. The composition may comprise at least on HDAC inhibitor. The composition may comprise at least one HDAC inhibitor in combination with an excipient, diluent, carrier, or combination thereof.

The composition may be in a variety of forms, suitable, for example, for systemic administration (e.g., oral, rectal, nasal, sublingual, buccal, or parenteral) or topical administration (e.g., local application on the skin, ocular, liposome delivery systems, or iontophoresis).

6) ADMINISTRATION

"Administration" or "administering" refers to delivery of the compounds by any appropriate route to achieve the desired effect.

The HDAC inhibitor or composition comprising the HDAC inhibitor may be administered to a subject by any convenient route of administration, whether systemically/peripherally or at the site of desired action, including but not limited to, oral (e.g., by ingestion); topical (including e.g., transdermal, intranasal, ocular, buccal, and sublingual); pulmonary (e.g., by inhalation or insufflation therapy using, e.g., an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

7) METHODS

The novel HDAC inhibitors detailed herein are efficacious in various methods of treatment, for example, for treating cancer and for treating neurological disorders.

c) Methods of Treating Cancer

Class I HDACs are expressed at greater levels in numerous types of cancers such as prostate (HDAC1), ovarian (HDAC1, HDAC2, and HDAC3), breast (HDAC1), colorectal (HDAC1 and HDAC2), lung (HDAC1 and HDAC3), gastric (HDAC1 and HDAC2), pancreatic (HDAC2), and hepatocellular carcinomas, relative to normal cells. Class IIa HDAC6 expression was observed in breast and ovarian cancer. HDAC5 expression was observed to be downregulated in colon cancer and acute myeloid leukemia.

Provided herein is a method of treating cancer. The methods may include administering an effective amount of a HDAC inhibitor as detailed herein to a subject in need thereof. Administration of the HDAC inhibitor may result in inhibition of a HDAC in the subject. Administration of the HDAC inhibitor may result in inhibition of a single or multiple HDAC isoforms in the subject. In some embodiments, the HDAC inhibitor specifically inhibits class I and class II HDACs to treat cancer. In some embodiments, the HDAC inhibitor specifically inhibits class I HDACs to treat cancer. In some embodiments, the HDAC inhibitor specifically inhibits HDAC1 to treat cancer. In some embodiments, the HDAC inhibitor specifically inhibits HDAC2 to treat cancer. In some embodiments, the HDAC inhibitor specifically inhibits HDAC3 to treat cancer. In some embodiments, the HDAC inhibitor specifically inhibits HDAC8 to treat cancer. In some embodiments, the HDAC inhibitor specifically inhibits HDAC1 and HDAC2 to treat cancer.

Inhibition of HDAC has been estimated to alter the expression of approximately 2-10% of genes, with as many genes downregulated as upregulated. Inhibition of HDAC may lead to chromatin remodeling, tumor suppressor gene reactivation, apoptosis, inhibition or regression of cancer proliferation or differentiation, or a combination thereof. CDKNA1 is one example of a gene that may be upregulated by HDAC inhibitors.

The HDAC inhibitor may be used as a single agent or in combination with other cancer therapeutics or anti-cancer agents such as other small molecule compounds, chemotherapy drugs, antibodies, surgery, radiation, or other adjuvant or neoadjuvant therapies. Examples of chemotherapy drugs include, but are not limited to, etoposide, cisplatin, bortezomib, and gemcitabine.

In some embodiments, cancer is selected from the group consisting of sarcoma, carcinoma, lymphoma, adenoma, melanoma, myeloid leukemia, lymphatic leukemia, blastoma, glioma, astrocytoma, mesothelioma, or a germ cell tumor. In some embodiments, cancer is selected from the group consisting of ovarian, lung, small cell lung, head, colorectal, rectal, gastric, heart, liver, pancreatic, bladder, prostate, colon, breast, testicular, brain, skin, esophageal, tracheal, head and neck, lymphoid, leukemia, glioblastoma, vulvar, melanoma, mesothelioma, renal, thyroid, soft tissue, and bone cancer. In some embodiments, cancer is selected from the group consisting of colon, melanoma, ovarian, T cell lymphoma, and renal cancer.

d) Methods of Treating Neurological Disorders

HDAC2 and HDAC3 have been implicated in hippocampal memory formation. Acetylation of histone proteins around which DNA is supercoiled may increase gene transcription and lead to increased synaptic plasticity in the brain and enhanced learning and memory in mouse models of Alzheimer's Disease. Histone acetylation is reduced by HDAC enzymes and can be pharmacologically increased by HDAC inhibitors. Elevated histone acetylation may enhance the formation of object recognition and spatial memories in mice. HDAC inhibitors may increase synaptic plasticity in the brain and enhance learning and memory in mouse models of Alzheimer's disease. Moreover, treatment of mice with an HDAC inhibitor may enhance memory formation and doubles the length of time memories are retained. HDAC inhibitors may reduce cognitive impairment in the elderly and patients with neurodegenerative diseases.

Provided herein is a method of treating a subject with a neurological disorder. The methods may include administering an effective amount of a HDAC inhibitor as detailed above to a subject in need thereof. Administration of the HDAC inhibitor may result in inhibition of a HDAC in the subject. Administration of the HDAC inhibitor may result in inhibition of a single or multiple HDAC isoforms in the subject. Inhibition of HDAC may lead to chromatin remodeling, increased or decreased gene transcription, and/or reactivation or inactivation of certain genes, resulting in treatment of the neurological disorder. The HDAC inhibitor may be used as a single agent or in combination with other therapies.

In some embodiments, the neurological disorder is selected from the group consisting of dementia, memory deficit, memory dysfunction, memory loss, cognition defects, cognitive impairment, amyotrophic lateral sclerosis, Alzheimer's Disease, Parkinson's Disease, Huntington's Disease, mood disorders (such as, for example, depression and bipolar disorder), substance abuse, and schizophrenia. In some embodiments, the neurological disorder is selected from the group consisting of dementia, memory deficit, memory dysfunction, memory loss, cognition defects, cognitive impairment, and Alzheimer's Disease.

e) Methods of Enhancing Memory and/or Improving Cognition

Further provided herein is a method of enhancing memory and/or improving cognition. The methods may include administering an effective amount of a HDAC inhibitor as detailed above to a subject in need thereof. Administration of the HDAC inhibitor may result in inhibition of a HDAC in the subject. Administration of the HDAC inhibitor may result in inhibition of a single or multiple HDAC isoforms in the subject. Inhibition of HDAC may lead to chromatin remodeling, increased or decreased gene transcription, and/or reactivation or inactivation of certain genes, resulting in enhancement of memory and/or improvement in cognition. The HDAC inhibitor may be used as a single agent or in combination with other therapies.

f) Methods of Inhibiting a HDAC in a Subject in Need Thereof

Provided herein is a method of inhibiting a HDAC in a subject in need thereof. The methods may include administering an effective amount of a HDAC inhibitor as detailed herein to a subject in need thereof. Administration of the HDAC inhibitor may result in inhibition of a HDAC in the subject. Administration of the HDAC inhibitor may result in inhibition of a single or multiple HDAC isoforms in the subject. Administration of the HDAC inhibitor may specifically inhibit a single or multiple HDAC isoforms in the subject.

8) EXAMPLES

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

Example 1

Molecular Modelling

HDACs are classified into 11 isoforms. Among them, four isoforms have their X-ray structures in the Protein Data Bank (PDB): HDAC2 (3MAX), HDAC3 (4A69), HDAC7 (3C0Z), and HDAC8 (1T69). Many of these X-ray crystals have their active site bound with small molecules. TDP-A and all fragments were docked in HDAC2 (3MAX), as HDAC 2 is the most potent isoform available.

Figure 6:
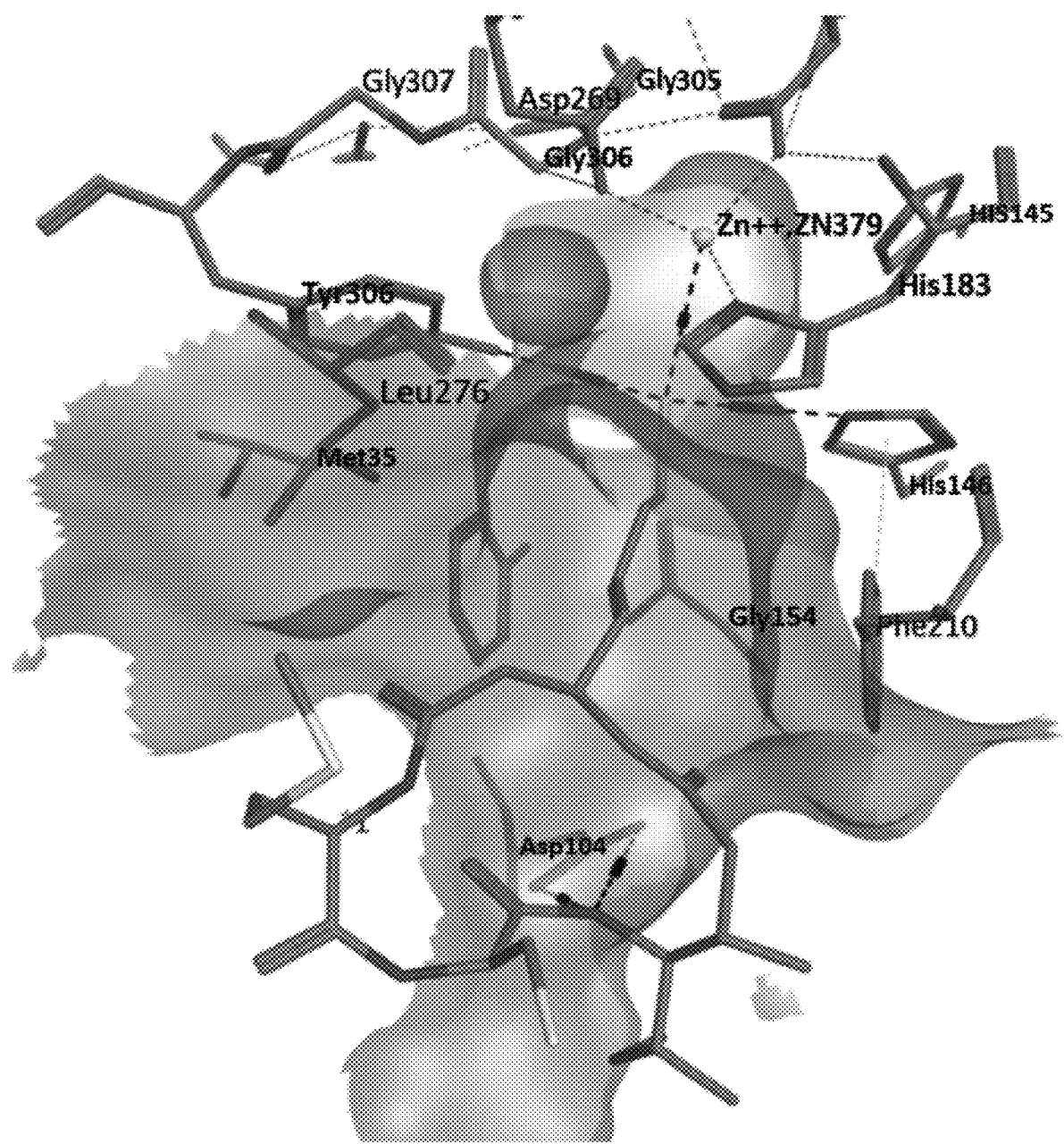
FIG. 6 shows the lowest energy conformation of TDP-A in the HDAC2 catalytic core in surface view.
Figure 7:
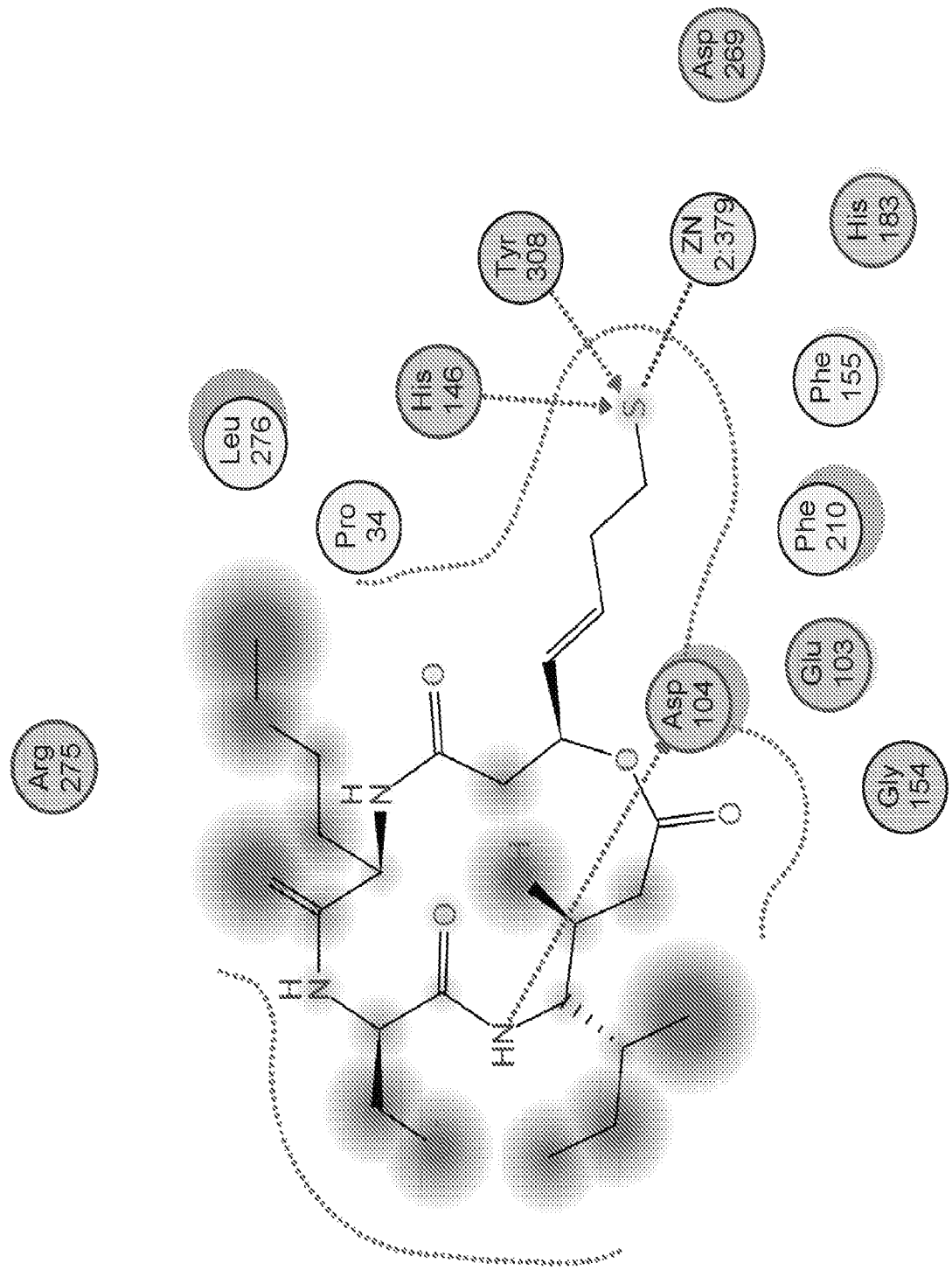
FIG. 7 is schematic representation of TDP-A binding in HDAC2.

Analysis indicated that the natural product TDP-A has similar binding modes and orientation as FK228 and SAHA in the active site. The thiol of TDP-A chelated with the zinc ion and to resdules His 146 and Tyr 308. The residual His 146 played a key role in centering the thiol in the middle of the pocket. It was further concluded that small fragments like TDF1 could chelate to the zinc in reverse manner while the carboxylic acid is hydrogen bonding to the Tyr 29 residual and water. Shown in FIG. 6 and FIG. 7 is the lowest energy conformation of TDP-A in the HDAC2 catalytic core. Natural product TDP-A was docked into a model based on the crystal structure of HDAC 2 (PDB: 3MAX), using the software packages of MOE. FIG. 6 shows the surface view of TDP-A docked in HDAC2 catalytic pocket, and FIG. 7 shows the schematic representation of TDP-A binding in HDAC2.

Example 2

Synthesis of Compounds

All reactions in non-aqueous media were conducted under a positive pressure of dry argon in glassware that had been oven dried prior to use unless noted otherwise. Anhydrous solutions of reaction mixtures were transferred via an oven dried syringe or cannula. All solvents were dried prior to use unless noted otherwise. 1H and 13C Nuclear magnetic resonance spectra (NMR) were obtained on a Varian Unity-Inova 400 MHz or 500 MHz recorded in ppm ($\delta$) downfield of TMS ($\delta$=0). Signal splitting patterns were described as singlet (s), doublet (d), triplet (t), quartet (q), quintet (quint), or multiplet (m), with coupling constants (J) in hertz. High resolution mass spectra (HRMS) were performed by UW Biotech Center on an Electron Spray Injection (ESI) mass spectrometer.

Synthesis of TDC1.

To a stirred solution of TDP-A (27 mg, 0.5 mmol) and DMAP (one crystal) in anhydrous pyridine (1 mL) was added benzoyl chloride (12 mg, 0.75 mmol) at 0° C. The reaction mixture was allowed to warm to room temperature and stirred for 40 h. The reaction mixture was poured into $H_2O$ (20 mL) and extracted with $Et_2O$ (3×10 mL). The combined organic layers were washed with brine (1×10 mL), dried over anhydrous $Na_2SO_4$, filtered and concentrated in vacuo. The residue was purified by flash column chromatography (Hexane/Ethyl acetate=50:50) to yield TDC1 (27 mg, 82%).

$^1$H NMR (400 MHz, $CDCl_3$, TMS): $\delta$ 0.88-0.98 (m, 7H), 1.19-1.28 (m, 1H), 1.39-1.48 (m, 1H), 1.88-1.91 (m, 1H), 2.09-2.16 (m, 1H), 2.21 (s, 3H), 2.30-2.36 (m, 1H), 2.46 (s, 1H), 2.63-2.85 (m, 6H), 2.96 (dd, J=11.6, 3.2 Hz, 1H), 3.20-3.33 (m, 3H), 3.40-3.48 (m, 2H), 4.41-4.44 (m, 1H), 5.00 (s, 1H), 5.59 (s, 1H), 5.71 (d, J=12.8 Hz, 1H), 6.10-6.13 (m, 1H), 6.32 (s, 1H), 6.83 (d, J=7.6 Hz, 1H), 7.43-7.48 (m, 3H), 7.56-7.59 (m, 1H), 7.67 (d, J=2.8 Hz, 1H), 8.10 (d, J=6.8 Hz, 1H). $^{13}$C NMR (100 MHz, $CDCl_3$, TMS): $\delta$ 11.8, 15.5, 15.7, 20.5, 22.5, 27.1, 28.0, 28.6, 31.5, 36.9, 37.3, 41.4, 57.7, 58.1, 59.9, 69.9, 70.2, 109.9, 128.7, 130.0, 130.3, 133.3, 133.3, 165.9, 169.2, 169.4, 170.4, 171.3. HRMS (ESI) m/z calcd for $C_{30}H_{41}N_3O_7S_3$ (M+Na) 674.1999, found 674.2016.

Synthesis of TDC2.

The synthesis of TDC2 was carried out following the procedure described for the synthesis of TDC1 using chloroethyl formate (TDC2, 25 mg, 85%).

$^1$H NMR (400 MHz, CDCl3, TMS): $\delta$ 0.90-0.93 (m, 6H), 1.18-1.27 (m, 2H), 1.33 (t, J=5.6 Hz, 3H), 1.39-1.47 (m, 1H), 1.84-1.87 (m, 1H), 2.05-2.12 (m, 1H), 2.20 (s, 3H), 2.29-2.35 (m, 1H), 2.47 (s, 1H), 2.58-2.66 (m, 2H), 2.66-2.73 (m, 3H), 2.78-2.81 (m, 1H), 2.95 (dd, J=11.6, 3.2 Hz, 1H), 3.05-3.10 (s, 1H), 3.19 (dd, J=10.8, 5.6 Hz, 2H), 3.27-3.31 (m, 1H), 4.20-4.26 (m, 2H), 4.37-4.41 (m, 1H), 4.98 (s, 1H), 5.63 (s, 1H), 5.67-5.72 (m, 2H), 6.33 (s, 1H), 6.76 (d, J=8.0 Hz, 1H), 7.35 (d, J=5.6 Hz, 1H), 7.58 (d, J=3.5 Hz, 1H). $^{13}$C NMR (100 MHz, $CDCl_3$, TMS): $\delta$ 11.8, 14.5, 15.2, 15.8, 27.2, 28.0, 31.6, 36.7, 37.1, 41.4, 57.8, 58.0, 64.5, 70.1, 73.2, 129.6, 133.2, 154.4, 169.0, 169.4, 170.3, 171.2. HRMS (ESI) m/z calcd for $C_{26}H_{41}N_3O_8S_3$ (M+Na) 642.1948, found 642.1959.

Synthesis of TDC3.

The synthesis of TDC3 was carried out following the procedure described for the preparation of TDC1 using acetyl chloride (TDC3, 30 mg, 92%).

$^1$H NMR (400 MHz, CDCl3, TMS): $\delta$ 0.91 (t, J=6.0 Hz, 6H), 1.15-1.31 (m, 1H), 1.37-1.45 (m, 1H), 1.81-1.86 (m, 1H), 2.07-2.12 (m, 1H), 2.13 (s, 3H), 2.20 (s, 3H), 2.28-2.34 (m, 1H), 2.44-2.46 (m, 1H), 2.60-2.72 (m, 5H), 2.78-2.85 (m, 1H), 2.87 (dd, J=8.4, 4.8 Hz, 1H), 3.05-3.12 (s, 1H), 3.20-3.27 (m, 3H), 4.38-4.41 (m, 1H), 4.96 (s, 1H), 5.61 (s, 1H), 5.69 (d, J=12.4 Hz, 1H), 5.79-5.83 (m, 1H), 6.30 (s, 1H), 6.78 (d, J=7.6 Hz, 1H), 7.35 (d, J=5.6 Hz, 1H), 7.62 (d, J=3.5 Hz, 1H). $^{13}$C NMR (100 MHz, $CDCl_3$, TMS): $\delta$ 11.7, 15.4, 15.7, 20.3, 21.5, 22.5, 27.1, 28.0, 28.6, 31.5, 36.7, 36.9, 41.4, 57.7, 58.0, 59.6, 69.7, 70.1, 129.5, 133.2, 169.3, 170.4, 170.5, 171.2. HRMS (ESI) m/z calcd for $C_{25}H_{39}N_3O_7S_3$ (M+Na) 612.1842, found 612.1858.

(E)-5-(tritylthio)pent-2-enal (2). This compound is the precursor for the preparation of compound 4. A round bottom flask was charged with 3-(tritylthio)propanal (3.77 g, 11.3 mmol) and 2-(triphenylphosphoranylidene) (3.8 g, 12.5 mmol, 1.1 equiv.). The flask was put under argon and the contents of the flask were dissolved in benzene (90 mL). The solution was then refluxed overnight. The reaction mixture was allowed to cool to room temperature and was then concentrated in vacuo. The crude product was separated twice via column chromatography. The first column was run with a 20% ethyl acetate/hexane solution until the product spot eluted. A second column was run and the product eluted with 10% ether/hexane to give 2.83 g (70%) of compound 2 as pure product. $^1$H NMR (500 MHz, $CDCl_3$, 25° C.) $\delta$ (ppm) 9.45-9.44 (d, 1H), 7.44-7.24 (m, 15H), 6.64 (t, 1H), 6.02-5.97 (dd, 1H), 2.36-2.32 (m, 4H); <jul12211> Exp 1 $^{13}$C NMR (CDCl$_3$, 150 MHz) δ (ppm) 193.6, 155.6, 144.5, 133.6, 129.5, 127.9, 126.7, 31.6, 29.9 Fuse, et al. Total Synthesis of Spiruchostatin B Aided by an Automated Synthesizer. *Org. Biomol. Chem.* 2011, 9, 3825-3833.

(E)-1-tert-butoxy-4-hydroxy-8-(tritylthio)oct-5-en-2-one (3). This compound is the precursor for the preparation of Cpd3'. To a 50 mL round bottom flask was charged with THF (100 mL) and cooled to −78° C. Next, diisopropylethylamine (DIPEA) (4.86 mL, 27.89 mmol, 5.5 equiv.) and n-butyllithium (12.27 mL, 30.68 mmol, 5.5 equiv.) were added dropwise at −78° C. and let stir for 1 hr. Tert-butyl acetate (3.7 mL, 27.6 mmol, 5 eqv.) was added at −78° C. and was allowed to stir for 1 hr. Lastly, (E)-5-(tritylthio)pent-2-enal (2) (2.0 g, 5.579 mmol, 1 equiv.) was added and let stir for 45 min at −78° C. The reaction was quenched with a saturated solution of NH$_4$Cl (50 mL) at −78° C. and then concentrated in vacuo to remove the organic solvent. Then dichloromethane was added to aqueous mixture and the two phases were separated. Then the aqueous layer was extracted two more times with dichloromethane and the organic layers were combined. The organic layer was washed with NaHCO$_3$, brine, then dried over anhydrous Na$_2$SO$_4$, and concentrated in vacuo. Chromatography on SiO$_2$ (ethyl acetate/hexane, 1:9) gave 2.06 g (78%) of compound 3 as a white solid. $^1$H NMR (300 MHz, CDCl$_3$, 25° C.) δ (ppm) 7.43 (d, 6H), 7.30 (m, 9H), 5.62-5.55 (m, 1H), 5.47-5.40 (dd, 1H), 4.42 (s, 1H), 3.09 (bs, OH), 2.43 (m, 2H), 2.23 (m, 2H), 2.10 (m, 2H), 1.47 (s, 9H); $^{13}$C NMR (75 MHz, CDCl$_3$, 25° C.) δ (ppm) 172.8, 144.9, 132.1, 129.9, 129.6, 127.9, 126.6, 81.3, 69, 66.6, 42.4, 31.5, 31.4, 28.2.

(E)-3-hydroxy-7-(tritylthio)hept-4-enoic acid (4). This compound is the building block for the preparation of compounds Cpd1-6 and Cpd1'-6'. (E)-1-tert-butoxy-4-hydroxy-8-(tritylthio)oct-5-en-2-one (3) (400 mg, 0.843 mmol, 1.0 equiv.) was dissolved in a 4:1 ratio of THF/water (10 mL). Next, lithium hydroxide (620 mg, 25.89 mmol, 25 equiv.) was added. The solution was then heated to 50° C. and stirred for 12 hr. The reaction was then diluted with water (10 mL) and then acidified to a pH of 4-5 with KHSO$_4$. The aqueous layer was extracted with ethyl acetate (10 mL) four times. The organic layers were combined and washed with water, brine, dried over anhydrous sodium sulfate, and concentrated in vacuo. Chromatography on SiO$_2$ (ethyl acetate/hexane, 9:10) gave 353 mg (95%) of compound 4 as a white solid. $^1$H NMR (300 MHz, CDCl$_3$, 25° C.) δ 7.47-7.23 (m, 15H), 5.64-5.57 (m, 1H), 5.49-5.42 (dd, 1H), 4.49 (q, 1H), 2.55 (d, 2H) 2.24 (m, 2H), 2.09 (m, 2H); $^{13}$C NMR (125 MHz, CDCl$_3$, 25° C.) δ (ppm) 171.9, 144.9, 131.7, 130.7, 129.6, 128.0, 126.7, 68.6, 66.7, 41.3, 31.5, 31.4.

(4E,4'E)-7,7'-disulfanediylbis(3-hydroxyhept-4-enoic acid) (Cpd3). Iodine (52.2 mg, 0.206 mmol, 0.5 equiv.) and sodium acetate (33.7 mg, 0.411 mmol, 1.0 equiv.) were dissolved in a 10:1 solution of CH$_2$Cl$_2$/MeOH (10 mL). (E)-3-hydroxy-7-(tritylthio)hept-4-enoic acid (4) (172 mg, 0.411 mmol, 1 equiv.) was dissolved in a 10:1 solution of CH$_2$Cl$_2$/MeOH (5 mL) and was added dropwise at 0° C. over 20 minutes to the solution containing iodine and sodium acetate. This solution was then allowed to stir for 2 hr. The reaction was quenched by adding a saturated sodium thiosulfate (Na$_2$S$_2$O$_3$) solution until the reaction mixture turned clear. Then, brine (5 mL) was added and the phases were separated. The aqueous layer was extracted with dichloromethane (3×15 mL) and then with ethyl acetate (3×15 mL). The organic layers were combined, dried over Na$_2$SO$_4$, and concentrated in vacuo. The crude reaction mixture was first purified by Hi-Flash Column (ODS-C18, 3.0×16.5 cm, 50 um, Yamazen A1-580), 0-20 min 20-100% ACN/H$_2$O 20 mL/min and the detection wave length was set up at 210 nm. The peak was collected at 8-12 min. Then this peak was injected in the HPLC (Varian ProStar) with the column (Prep-C18, 21.2×250 mm, 10 μm) system and 40% ACN/H$_2$O was used to elute the column under the flow rate of 8 mL/min. The wavelength was set at 200 nm to detect the compound and 46 mg of the pure compound (Cpd3) was collected at 12-14.5 min. (31.9% yield.) $^1$H NMR (500 MHz, DMSO, 25° C.) δ (ppm) 5.71 (m, 1H), 5.54 (dd, 1H), 4.43 (m, 1H), 2.69 (m, 2H), 2.48 (m, 2H), 2.38 (m, 2H); $^{13}$C NMR (125 MHz, CD$_3$OD, 25° C.) δ (ppm) 173.6, 133.3, 128.7, 68.6, 42.0, 37.7, 31.5.

Di-tert-butyl 7,7'-disulfanediyl(4E,4'E)-bis(3-hydroxyhept-4-enoate) (Cpd3'). Iodine (58.9 mg, 0.232 mmol, 1.0 equiv.) and sodium acetate (19.0 mg, 0.464 mmol, 2.0 equiv.) were dissolved in a 10:1 solution of CH$_2$Cl$_2$/MeOH (5 mL). (E)-1-tert-butoxy-4-hydroxy-8-(tritylthio)oct-5-en-2-one (3) (110 mg, 0.232 mmol, 1.0 equiv.) was dissolved in a 10:1 solution of CH$_2$Cl$_2$/MeOH (5 mL) and was added dropwise at 0° C. over 20 minutes to the first solution containing iodine and sodium acetate. This solution was then allowed to stir for 2 hr. The reaction was quenched by adding a saturated sodium thiosulfate (Na$_2$S$_2$O$_3$) solution until the reaction mixture turned clear. Then, brine (5 mL) was added and the phases were separated. The aqueous layer was extracted with dichloromethane (3×15 mL) and then with ethyl acetate (3×15 mL). The organic layers were combined, dried over Na$_2$SO$_4$, and concentrated in vacuo. The crude reaction mixture was first purified by Hi-Flash Column (ODS-C18, 3.0×16.5 cm, 50 μm, Yamazen A1-580), 0-20 min 20-100% ACN/H$_2$O 20 mL/min and the detection wave length was set up at 210 nm. The peak was collected at 15-20 min. Then this peak was injected in the HPLC (Varian ProStar) with the column (Prep-C18, 21.2×250 mm, 10 μm) system and 70% ACN/H$_2$O was used to elute the column under the flow rate of 8 mL/min. The wavelength was set at 200 nm to detect the compound and 140 mg of the pure compound (Cpd3') was collected at 22-25 min. (65.5% yield.) $^1$H NMR (300 MHz, CD$_3$OD, 25° C.) δ (ppm) 5.75 (m, 1H), 5.66 (dd, 1H), 4.47 (m, 1H), 2.78 (m, 2H), 2.44 (m, 4H), 1.50 (s, 9H); $^{13}$C NMR (75 MHz, CD$_3$OD, 25° C.) δ (ppm) 170.9, 133.4, 128.8, 80.5, 68.8, 43.4, 37.7, 31.5, 27.1.

Methyl (2R)-2-[(4E)-3-hydroxy-7-[(triphenylmethyl)sulfanyl]hept-4-enamido]-4-(methylsulfanyl)butanoate (6). (E)-3-hydroxy-7-(tritylthio)hept-4-enoic acid (4) (410 mg, 0.980 mmol, 1.2 equiv.) and D-methionine methyl ester hydrochloride salt (163 mg, 0.816, 1.0 equiv.) were dissolved in dichloromethane (anhydrous) (35 mL) under Ar. The reaction was cooled to 0° C. and then benzotriazol-1-yl-oxytripyrrolidinophosphonium hexafluorophosphate (PyBOP) (510 mg, 0.980 mmol, 1.2 equiv.) was added. The solution stirred for 10 min and then DIPEA (0.208 mL, 1.19 mmol, 4 equiv.) was added. The reaction was allowed to warm to 25° C. and stirred for 12 hr. It was then quenched with a saturated NH$_4$Cl, extracted with dichloromethane (3×15 mL), washed with brine, dried over Na$_2$SO$_4$, and then concentrated in vacuo. Chromatography on SiO$_2$ (ethyl acetate/hexane, 2:3) gave 360 mg (81%) of product (6) as a white solid. $^1$H NMR (300 MHz, CDCl$_3$, 25° C.) δ 7.43-7.41 (m, 6H), 7.27 (m, 9H), 6.67 (s, NH), 5.56 (m, 1H), 5.45 (dd, 1H), 4.73 (m, 1H), 4.44 (m, 1H), 3.76 (s, 3H), 3.51 (s, OH), 2.52 (t, 2H), 2.41 (m, 2H), 2.21 (m, 3H), 2.15-1.95 (m, 6H); $^{13}$C NMR (125 MHz, CDCl$_3$, 25° C.) δ (ppm) 172.7, 171.4, 144.9, 132.4, 129.9, 129.6 127.9, 126.7, 69.1, 66.6, 52.7, 51.4, 42.8, 36.7, 31.4, 30.0, 24.8, 15.5.

2R)-2-[(4E)-3-hydroxy-7-[(triphenylmethyl)sulfanyl]hept-4-enamido]-4-(methylsulfanyl)butanoic acid (7). Methyl (2R)-2-[(4E)-3-hydroxy-7-[(triphenylmethyl)sulfanyl]hept-4-enamido]-4-(methylsulfanyl)butanoate (6) (333 mg, 0.591 mmol, 1.0 equiv.) was dissolved in a 4:1 ratio of THF/water (10 mL). Next was added lithium hydroxide (353 mg, 14.8 mmol, 25 equiv.). The solution was then heated to 50° C. and stirred for 12 hr. The reaction was then diluted with water (10 mL) and then acidified to a pH of 4-5 with $KHSO_4$. The aqueous layer was extracted with ethyl acetate (10 mL) four times. The organic layers were combined and washed with water, brine, dried over anhydrous $Na_2SO_4$, and concentrated in vacuo. Chromatography on $SiO_2$ (ethyl acetate/hexane, 1:1) gave 290 mg (89%) of compound 7 as a white solid. $^1$H NMR (500 MHz, $CDCl_3$, 25° C.) δ (ppm) 7.43-7.21 (m, 15H), 6.95-6.85 (m, NH), 5.60 (m, 1H), 5.46 (m, 1H), 4.68 (m, 1H), 4.46 (m, 1H), 4.44 (bs, OH), 2.56 (t, 2H), 2.43 (m, 2H), 2.23 (t, 3H), 2.10 (s, 3H) 2.08 (m, 2H), 2.02 (m, 1H); $^{13}$C NMR (125 MHz, $CDCl_3$, 25° C.) δ (ppm) 174.4, 172.71, 144.9, 132.0, 131.9, 130.4, 130.3, 129.6, 126.7, 69.2, 66.7, 51.8, 43.4, 42.8, 31.4, 31.0, 30.1, 15.4.

Methyl (2R)-2-[(4E)-3-hydroxy-7-{[(3E)-5-hydroxy-6-{[(2R)-1-methoxy-4-(methylsulfanyl)-1-oxobutan-2-yl]carbamoyl}hex-3-en-1-yl]disulfanyl}hept-4-enamido]-4-(methylsulfanyl)butanoate (Cpd2'). Iodine (59.2 mg, 0.233 mmol, 1 equiv.) and sodium acetate (38.2 mg, 0.466 mmol, 2 equiv.) were dissolved in a 10:1 solution of $CH_2Cl_2$/MeOH (5 mL). Methyl (2R)-2-[(4E)-3-hydroxy-7-[(triphenylmethyl)sulfanyl]hept-4-enamido]-4-(methylsulfanyl)butanoate (6) (526 mg, 0.233 mmol, 1 equiv.) was dissolved in a 10:1 solution of $CH_2Cl_2$/MeOH (5 mL) and was added dropwise at 0° C. over 20 minutes to the first solution containing iodine and sodium acetate. This solution was then allowed to stir for 2 hr. The reaction was quenched by adding a saturated sodium thiosulfate ($Na_2S_2O_3$) solution until the reaction mixture turned clear. Then brine (5 mL) was added and the phases were separated. The aqueous layer was extracted with dichloromethane (3×15 mL) and then with ethyl acetate (3×15 mL). The organic layers were combined, dried over $Na_2SO_4$, and concentrated in vacuo. The crude reaction mixture was first purified by Hi-Flash Column (ODS-C18, 3.0×16.5 cm, 50 um, Yamazen A1-580), 0-20 min 20-100% ACN/$H_2O$ 20 mL/min and the detection wavelength was set at 210 nm. The peak was collected at 12-15 min. Then this peak was injected in the HPLC (Varian ProStar) with the column (Prep-C18, 21.2×250 mm, 10 μm) system and 40% ACN/$H_2O$ was used to elute the column under the flow rate of 8 mL/min. The wave length was set at 200 nm to detect the compound and 40 mg of the pure compound (Cpd2') was collected at 19-21 min. (25.7% yield.) $^1$H NMR (300 MHz, $CDCl_3$, 25° C.) δ (ppm) 7.60 (s, NH), 5.77-5.70 (m, 1H), 5.67-5.61 (dd, 1H), 4.62 (m, 1H), 4.49-4.40 (m, 1H), 4.39 (s, OH), 3.71 (s, 3H), 2.86-2.77 (m, 2H), 2.55 (m, 2H), 2.45-2.41 (m, 4H), 2.15-2.05 (m, 1H) 2.09 (s, 3H), 1.96 (m, 1H); $^{13}$C NMR (125 MHz, $(CD_3)_2CO$, 25° C.) δ (ppm) 173.5, 172.4, 135.5, 135.4, 129.1, 129.0, 70.0, 52.8, 52.4, 44.4, 39.3, 33.0, 32.7, 31.0, 15.6.

(2R)-2-[(4E)-7-{[(3E)-6-{[(1R)-1-carboxy-3-(methylsulfanyl)propyl]carbamoyl}-5-hydroxyhex-3-en-1-yl]disulfanyl}-3-hydroxyhept-4-enamido]-4-(methylsulfanyl)butanoic acid (Cpd2). Iodine (66.8 mg, 0.258 mmol, 1 equiv.) and sodium acetate (42.4 mg, 0.517 mmol, 2 equiv.) were dissolved in a 10:1 solution of $CH_2Cl_2$/MeOH (5 mL). (2R)-2-[(4E)-3-hydroxy-7-[(triphenylmethyl)sulfanyl]hept-4-enamido]-4-(methylsulfanyl)butanoic acid (7) (142 mg, 0.258 mmol, 1 equiv.) was dissolved in a 10:1 solution of $CH_2Cl_2$/MeOH (5 mL) and was added dropwise at 0° C. over 20 minutes to the first solution containing iodine and sodium acetate. This solution was then allowed to stir for 2 hr. The reaction was quenched by adding a saturated sodium thiosulfate ($Na_2S_2O_3$) solution until the reaction mixture turned clear. Then brine (5 mL) was added and the phases were separated. The aqueous layer was extracted with dichloromethane (3×15 mL) and then with ethyl acetate (3×15 mL). The organic layers were combined, dried over $Na_2SO_4$, and concentrated in vacuo. The crude reaction mixture was first purified by Hi-Flash Column (ODS-C18, 3.0×16.5 cm, 50 μm, Yamazen A1-580), 0-20 min 20-100% ACN/$H_2O$ 20 mL/min and the detection wave length was set at 210 nm. The peak was collected at 8-12 min. Then this peak was injected in HPLC (Varian ProStar) with the column (Prep-C18, 21.2×250 mm, 10 μm) system and 35% ACN/$H_2O$ was used to elute the column under the flow rate of 8 mL/min. The wavelength was set at 200 nm to detect the compound, and 55 mg of the pure compound (Cpd2) was collected at 16-20 min. (34.8% yield.) $^1$H NMR (300 MHz, $CD_3OD$, 25° C.) δ (ppm) 5.72 (m, 1H), 5.62 (dd, 1H), 4.57 (m, 1H), 4.45 (m, 1H), 2.76 (m, 2H), 2.57 (m, 2H), 2.45 (m, 4H), 2.20-2.14 (m, 1H), 2.11 (s, 3H), 1.96 (m, 1H); $^{13}$C NMR (75 MHz, $CD_3OD$, 25° C.) δ (ppm) 173.8, 172.2, 133.4, 129.1, 69.1, 51.3, 43.4, 37.6, 31.6, 30.9, 29.7 13.8.

Methyl-(2S)-2-[(2R)-2-[(4E)-3-hydroxy-7-[(triphenylmethyl)sulfanyl]hept-4-enamido]-4-(methylsulfanyl)-butanamido]-3-[(triphenylmethyl)sulfanyl]propanoate (8). (2R)-2-[(4E)-3-hydroxy-7-[(triphenylmethyl)sulfanyl]-hept-4-enamido]-4-(methylsulfanyl)butanoic acid (7) (416 mg, 0.757 mmol, 1.2 equiv.) and S-trityl-D-cysteine (275 mg, 0.631 mmol 1.0 equiv.) were dissolved in dichloromethane (anhydrous) (35 mL) under Ar. The reaction was cooled to 0° C. and then benzotriazol-1-yl-oxytripyrrolidinophosphonium hexafluorophosphate (PyBOP) (433 mg, 0.832 mmol, 1.1 equiv.) was added. The solution stirred for 10 min and then DIPEA (0.394 mL, 2.27 mmol, 3.0 equiv.) was added. The reaction was allowed to warm to 25° C. and stirred for 14 hr. It was then quenched with a saturated $NH_4Cl$, extracted with dichloromethane (3×15 mL), washed with brine, dried over $Na_2SO_4$, and then concentrated in vacuo. Chromatography on $SiO_2$ (ethyl acetate/hexane, 2:3) gave 381 mg (55%) of compound 8 as a white solid. $^1$H NMR (500 MHz, $CDCl_3$, 25° C.) δ (ppm) 7.48-7.40 (m, 12H), 7.35-7.21 (m, 18H), 7.20-6.85 (m, 2H, NH), 5.55 (m, 1H), 5.45 (m, 1H), 4.70 (m, 1H), 4.54 (m, 1H), 4.46 (bs, 1H), 3.70 (d, 3H), 3.62-3.28 (bs, OH), 2.80-2.63 (m, 2H), 2.60 (t, 2H), 2.37 (m, 2H), 2.25 (m, 2H), 2.19-2.03 (m, 6H), 1.99 (m, 1H); $^{13}$C NMR (300 MHz, $CDCl_3$, 25° C.) δ (ppm) 171.7, 170.9, 170.7, 144.9, 144.2, 132.5, 130.1, 129.6, 129.5, 128.1, 127.9, 127.0, 126.6, 69.5, 66.9, 66.6, 52.7, 52.1, 51.4, 43.8, 42.7, 33.5, 31.5, 31.2, 30.0, 15.3.

(2S)-2-[(2R)-2-[(4E)-3-hydroxy-7-[(triphenylmethyl)sulfanyl]hept-4-enamido]-4-(methylsulfanyl)-butanamido]-3-[(triphenylmethyl)sulfanyl]propanoic acid (9). Methyl (2S)-2-[(2R)-2-[(4E)-3-hydroxy-7-[(triphenylmethyl)sulfanyl]hept-4-enamido]-4-(methylsulfanyl)butanamido]-3-[(triphenylmethyl)-sulfanyl]-propanoate (8) (400 mg, 0.440 mmol, 1.0 equiv.) was dissolved in a 4:1 ratio of THF/water (50 mL). Next was added lithium hydroxide (263 mg, 11.0 mmol, 25 equiv.). The solution was then stirred for 12 hr. The reaction was then diluted with water (30 mL) and then acidified to a pH of 4-5 with $KHSO_4$. The aqueous layer was extracted with ethyl acetate (15 mL) four times. The organic layers were combined and washed with water, brine, dried over anhydrous $Na_2SO_4$, and concentrated in vacuo. Chromatography on $SiO_2$ (ethyl acetate/hexane, 3:1) gave 327 mg (83%) of compound 9 as a white solid. $^1$H NMR (300

MHz, CDCl₃, 25° C.) δ (ppm) 7.54-7.14 (m, 30H), 7.09 (m, NH), 6.59 (m, NH), 6.48 (bs, OH), 5.54 (m, 1H), 5.42 (dd, 1H), 4.66 (m, 1H), 4.44-4.28 (m, 2H), 2.85-2.65 (m, 2H), 2.52 (t, 2H), 2.38 (m, 2H), 2.24 (m, 2H), 2.15-1.90 (m, 7H); ¹³C NMR (75 MHz, CDCl₃, 25° C.) δ (ppm) 172.4, 172.2, 171.4, 144.9, 144.3, 132.3, 130.0, 129.6, 129.5, 128.2, 127.9, 127.0, 126.7, 69.3, 67.1, 66.7, 52.4, 51.7, 43.4, 33.2, 31.5, 31.4, 31.1, 30.0, 15.3.

(4S,7R,12E)-11-hydroxy-7-[2-(methylsulfanyl)ethyl]-6,9-dioxo-1,2-dithia-5,8-diazacyclopentadec-12-ene-4-carboxylic acid (Cpd1). Iodine (44.5 mg, 0.172 mmol, 1.0 equiv.) and sodium acetate (28.2 mg, 0.344 mmol, 2.0 equiv.) were dissolved in a 10:1 solution of CH₂Cl₂/MeOH (25 mL). (2S)-2-[(2R)-2-[(4E)-3-hydroxy-7-[(triphenylmethyl)-sulfanyl]hept-4-enamido]-4-(methylsulfanyl)butanamido]-3-[(triphenylmethyl)sulfanyl]propanoic acid (9) (154 mg, 0.172 mmol, 1.0 equiv.) was dissolved in a 10:1 solution of CH₂Cl₂/MeOH (5 mL) and was added dropwise at 0° C. over 20 minutes to the first solution containing iodine and sodium acetate. This solution was then allowed to stir for 2 hr. The reaction was quenched by adding a saturated sodium thiosulfate (Na₂S₂O₃) solution until the reaction mixture turned clear. Then brine (5 mL) was added and the phases were separated. The aqueous layer was extracted with dichloromethane (3×15 mL) and then with ethyl acetate (3×15 mL). The organic layers were combined, dried over Na₂SO₄, and concentrated in vacuo. The crude reaction mixture was first purified by Hi-Flash Column (ODS-C18, 3.0×16.5 cm, 50 μm, Yamazen A1-580), 0-20 min 20-100% ACN/H₂O 20 mL/min and the detection wavelength was set at 210 nm. The peak was collected at 8-10 min. Then this peak was injected in the HPLC (Varian ProStar) with the column (Prep-C18, 21.2×250 mm, 10 μm) system and 35% ACN/H₂O was used to elute the column under the flow rate of 8 mL/min. The wavelength was set at 200 nm to detect the compound, and 25 mg of the pure compound was collected at 10-13.5 min. (35.6% yield.) ¹H NMR (500 MHz, CD₃OD, 25° C.) δ (ppm) 5.74 (m, 1H), 5.62-5.42 (m, 1H), 4.79 (bs, 2 OH), 4.64-4.20 (m, 3H), 2.93-2.78 (m, 2H), 2.78-2.65 (m, 2H), 2.64-2.44 (m, 4H), 2.42-2.31 (m, 2H), 2.14-2.08 (d, 3H), 2.05-1.87 (m, 2H); ¹³C NMR (125 MHz, CD₃OD, 25° C.) δ (ppm) 172.3, 170.7, 169.3, 133.2, 129.8, 70.0, 52.4, 51.9, 43.8, 39.3, 33.0, 31.4, 29.4, 28.7, 13.6.

Methyl (4S,7R,12E)-11-hydroxy-7-[2-(methylsulfanyl)ethyl]-6,9-dioxo-1,2-dithia-5,8-diazacyclopentadec-12-ene-4-carboxylate (Cpd1'). Iodine (93 mg, 0.364 mmol, 1.1 equiv.) and sodium acetate (52 mg, 0.661 mmol, 2 equiv.) were dissolved in a 10:1 solution of CH₂Cl₂/MeOH (25 mL). Methyl (2S)-2-[(2R)-2-[(4E)-3-hydroxy-7-[(triphenylmethyl)sulfanyl]hept-4-enamido]-4-(methylsulfanyl)butanamido]-3-[(triphenylmethyl)sulfanyl]-propanoate (8) (300 mg, 0.330 mmol, 1 equiv.) was dissolved in a 10:1 solution of CH₂Cl₂/MeOH (5 mL) and was added dropwise at 0° C. over 20 minutes to the first solution containing iodine and sodium acetate. This solution was then allowed to stir for 2 hr. The reaction was quenched by adding a saturated sodium thiosulfate (Na₂S₂O₃) solution until the reaction mixture turned clear. Then brine (5 mL) was added and the phases were separated. The aqueous layer was extracted with dichloromethane (3×15 mL) and then with ethyl acetate (3×15 mL). The organic layers were combined, dried over Na₂SO₄, and concentrated in vacuo. The crude reaction mixture was first purified by Hi-Flash Column (ODS-C18, 3.0×16.5 cm, 50 μm, Yamazen A1-580), 0-20 min 20-100% ACN/H₂O 20 mL/min and the detection wavelength was set up at 210 nm. The peak was collected at 12-15 min. Then this peak was injected in the HPLC (Varian ProStar) with the column (Prep-C18, 21.2×250 mm, 10 μm) system, and 40% ACN/H₂O was used to elute the column under the flow rate of 8 mL/min. The wavelength was set up at 200 nm to detect the compound, and 41 mg of the pure compound (Cpd1') was collected at 17-19 min. (29.4% yield.) ¹H NMR (300 MHz, (CD₃)₂SO, 25° C.) δ (ppm) 8.85-8.30 (m, NH), 8.15-7.95 (m, NH), 5.65-5.48 (m, 1H), 5.48-5.26 (m, 1H), 5.06-4.73 (m, OH), 4.72-4.51 (m, 1H), 4.50-4.32 (m, 1H), 4.31-4.10 (m, 1H), 3.70-3.60 (m, 3H), 3.26-3.10 (m, 2H), 2.96-2.69 (m, 2H), 2.67-2.12 (m, 6H), 2.04 (s, 3H), 1.92-1.65 (m, 2H); ¹³C NMR (75 MHz, (CD₃)₂SO, 25° C.) δ (ppm) 172.2, 171.3, 170.4, 133.9, 128.7, 70.0, 52.8, 51.6, 51.2, 44.8, 40.0, 33.5, 32.7, 32.2, 29.7, 16.5.

Methyl (2R)-2-[(4E)-3-hydroxy-7-[(triphenylmethyl)sulfanyl]hept-4-enamido]-3-methylbutanoate. (E)-3-hydroxy-7-(tritylthio)hept-4-enoic acid (150 mg, 0.358 mmol, 1.2 equiv.) and D-valine methyl ester hydrochloride salt (50 mg, 0.298 mmol, 1.0 equiv.) were dissolved in dichloromethane (anhydrous) (25 mL) under Ar. The reaction was cooled to 0° C. and then benzotriazol-1-yl-oxytripyrrolidinophosphonium hexafluorophosphate (PyBOP) (186 mg, 0.298 mmol, 1.2 equiv.) was added. The solution stirred for 10 min and then DIPEA (0.208 mL, 1.19 mmol, 4 equiv.) was added. The reaction was allowed to warm to 25° C. and stirred for 14 hr. It was then quenched with a saturated NH₄Cl, extracted with dichloromethane (3×15 mL), washed with brine, dried over Na₂SO₄, and then concentrated in vacuo. Chromatography on SiO₂ (ethyl acetate/hexane, 3:7) gave 127 mg (82%) of product as a white solid. ¹H NMR (300 MHz, CDCl₃, 25° C.) δ (ppm) 7.50-7.25 (m, 15H), 6.41 (m, NH), 5.57 (m, 1H), 5.46 (dd, 1H), 4.57 (m, 1H), 4.44 (m, 1H), 3.76 (s, 3H), 3.36 (s, OH), 2.43 (m, 2H), 2.20-2.11 (m, 5H), 0.94 (m, 6H); ¹³C NMR (75 MHz, CDCl3, 25° C.) δ (ppm) 172.6, 171.8, 144.9, 132.2, 130.2, 129.6, 127.9, 126.6, 69.3, 66.6, 56.9, 52.3, 43.0, 31.5, 31.4, 31.0, 19.0, 17.8.

(2R)-2-[(4E)-3-hydroxy-7-[(triphenylmethyl)sulfanyl]hept-4-enamido]-3-methylbutanoic acid. Methyl (2R)-2-[(4E)-3-hydroxy-7-[(triphenylmethyl)sulfanyl]hept-4-enamido]-3-methylbutanoate (122 mg, 0.229 mmol, 1.0 equiv.) was dissolved in a 4:1 ratio of THF/water (15 mL). Next was added lithium hydroxide (137 mg, 5.74 mmol, 25 equiv.). The solution was then stirred for 12 hours. The reaction was then diluted with water (10 mL) and then acidified to a pH of 4-5 with KHSO₄. The aqueous layer was extracted with ethyl acetate (15 mL) four times. The organic layers were combined and washed with water, brine, dried over anhydrous Na₂SO₄, and concentrated in vacuo. Chromatography on SiO₂ (ethyl acetate/hexane, 1:2) gave 99.5 mg (83%) of product as a white solid. ¹H NMR (300 MHz, CDCl₃, 25° C.) δ (ppm) 7.41 (m, 6H), 7.29 (m, 9H), 6.95-6.82 (m, NH), 5.54 (m, 1H), 5.45 (dd, 1H), 4.62-4.38 (m, 2H), 2.44 (m, 2H), 2.22 (m, 3H), 2.07 (m, 2H), 0.95 (m, 6H); ¹³C NMR (75 MHz, CDCl₃, 25° C.) δ (ppm) 173.9, 172.4, 144.9, 132.18, 130.1, 129.6, 127.9, 126.6, 69.3, 66.6, 56.9, 43.0, 31.5, 31.4, 30.6, 19.0, 17.8.

(2R)-2-[(4E)-7-{[(3E)-6-{[(1R)-1-carboxy-2-methylpropyl]carbamoyl}-5-hydroxyhex-3-en-1-yl]disulfanyl}-3 hydroxyhept-4-enamido]-3-methylbutanoic acid. Iodine (128 mg, 0.504 mmol, 1.1 equiv.) and sodium acetate (75.1 mg, 0.916 mmol, 2.0 equiv.) were dissolved in a 10:1 solution of CH₂Cl₂/MeOH (7 mL). (2R)-2-[(4E)-3-hydroxy-7-[(triphenylmethyl)sulfanyl]hept-4-enamido]-3-methylbutanoic acid (237 mg, 0.458 mmol, 1.0 equiv.) was dissolved in a 10:1 solution of CH₂Cl₂/MeOH (5 mL) and was added dropwise at 0° C. over 20 minutes to the first solution containing iodine and sodium acetate. This solution was then allowed to stir for 2 hours. The reaction was quenched by adding a saturated sodium thiosulfate ($Na_2S_2O_3$) solution until the reaction mixture turned clear. Then, brine (5 mL) was added and the phases were separated. The aqueous layer was extracted with dichloromethane (3×15 mL) and then with ethyl acetate (3×15 mL). The organic layers were combined, dried over $Na_2SO_4$, and concentrated in vacuo. The crude reaction mixture was first purified by Hi-Flash Column (ODS-C18, 3.0×16.5 cm, 50 µm, Yamazen A1-580), 0-20 min 20-100% $ACN/H_2O$ 20 mL/min and the detection wavelength was set at 210 nm. The peak was collected at 8-12 min. Then this peak was injected in HPLC (Varian ProStar) with the column (Prep-C18, 21.2×250 mm, 10 µm) system, and 35% $ACN/H_2O$ was used to elute the column under the flow rate of 8 mL/min. The wavelength was set at 200 nm to detect the compound, and 40 mg of the pure compound was collected at 13-18.5 min. (15.5% yield.) $^1H$ NMR (300 MHz, $CD_3OD$, 25° C.) δ (ppm) 5.75 (m, 1H), 5.62 (m, 1H), 4.49 (m, 1H), 4.37 (m, 1H), 2.75 (t, 2H), 2.58-2.37 (m, 4H), 2.25 (m, 1H), 1.00 (m, 6H); $^{13}C$ NMR (75 MHz, $CDCl_3/CD_3OD$, 25° C.) δ (ppm) 178.0, 176.2, 136.8, 133.2, 72.9, 61.3, 42.9, 35.6, 34.7, 34.6, 22.9, 21.5.

Methyl 2-[(4E)-3-hydroxy-7-{[(3E)-5-hydroxy-6-[(1-methoxy-3-methyl-1-oxobutan-2-yl)carbamoyl]hex-3-en-1-yl]disulfanyl}hept-4-enamido]-3-methylbutanoate. Iodine (118 mg, 0.465 mmol, 1.1 equiv.) and sodium acetate (69.4 mg, 0.846 mmol, 2 equiv.) were dissolved in a 10:1 solution of $CH_2Cl_2$/MeOH (15 mL). Methyl (2R)-2-[(4E)-3-hydroxy-7-[(triphenylmethyl)sulfanyl]hept-4-enamido]-3-methylbutanoate (225 mg, 0.423 mmol, 1 equiv.) was dissolved in a 10:1 solution of $CH_2Cl_2$/MeOH (5 mL) and was added dropwise at 0° C. over 20 minutes to the first solution containing iodine and sodium acetate. This solution was then allowed to stir for 2 hours. The reaction was quenched by adding a saturated sodium thiosulfate ($Na_2S_2O_3$) solution until the reaction mixture turned clear. Then brine (5 mL) was added and the phases were separated. The aqueous layer was extracted with dichloromethane (3×15 mL) and then with ethyl acetate (3×15 mL). The organic layers were combined, dried over $Na_2SO_4$, and concentrated in vacuo. The crude reaction mixture was first purified by Hi-Flash Column (ODS-C18, 3.0×16.5 cm, 50 µm, Yamazen A1-580), 0-20 min 20-100% $ACN/H_2O$ 20 mL/min, and the detection wavelength was set up at 210 nm. The peak was collected at 12-15 min. Then this peak was injected in the HPLC (Varian ProStar) with the column (Prep-C18, 21.2×250 mm, 10 um) system, and 50% $ACN/H_2O$ was used to elute the column under the flow rate of 8 mL/min. The wavelength was set up at 200 nm to detect the compound, and 90 mg of the pure compound was collected at 12-17 min. (37.0% yield.) $^1H$ NMR (300 MHz, $CD_2Cl_2$, 25° C.) δ (ppm) 6.82 (m, NH), 5.75 (m, 1H), 5.62 (dd, 1H), 4.49 (m, 2H), 3.95 (bs, OH), 3.75 (s, 3H), 2.79 (t, 2H), 2.54-2.39 (m, 4H), 2.25 (m, 1H), 0.95 (m, 6H); $^{13}C$ NMR (75 MHz, $CD_2Cl_2$, 25° C.) δ (ppm) 172.3, 171.8, 133.2, 129.1, 69.1, 57.1, 52.1, 42.7, 38.3, 31.7, 31.1, 18.9, 17.6.

Methyl (2R)-2-[(4E)-3-hydroxy-7-[(triphenylmethyl)sulfanyl]hept-4-enamido]hexanoate. (E)-3-hydroxy-7-(tritylthio)hept-4-enoic acid (1.0 g, 2.39 mmol, 1.0 eqv.) and D-norleucine methyl ester hydrochloride salt (346 g, 0.264 mmol, 1.1 equiv.) were dissolved in dichloromethane (anhydrous) (75 mL) under Ar. The reaction was cooled to 0° C. and then benzotriazol-1-yl-oxytripyrrolidinophosphonium hexafluorophosphate (PyBOP) (1.5 g, 2.88 mmol, 1.2 equiv.) was added. The solution stirred for 10 min and then DIPEA (1.51 mL, 8.32 mmol, 3.5 equiv.) was added. The reaction was allowed to warm to 25° C. and stirred for 14 hours. It was then quenched with a saturated $NH_4Cl$, extracted with dichloromethane (3×50 mL), washed with brine, dried over $Na_2SO_4$, and then concentrated in vacuo. Chromatography on $SiO_2$ (ethyl acetate/hexane, 3:7) gave 1.12 g (86%) of product as a white solid. $^1H$ NMR (300 MHz, $CDCl_3$, 25° C.) δ (ppm) 7.50-7.20 (m, 15H), 6.61 (t, 1H), 5.65 (m, 1H), 5.46 (dd, 1H) 4.62 (m, 1H), 4.45 (m, 1H), 3.74 (s, 3H), 2.40 (m, 2H), 2.23 (m, 2H), 2.10 (m, 2H), 1.83 (m, 1H), 1.68 (m, 1H), 1.32 (m, 4H), 0.91 (t, 3H); $^{13}C$ NMR (75 MHz, $CDCl_3$, 25° C.) δ (ppm) 172.5, 171.7, 144.9, 132.2, 129.9, 129.1, 127.5, 126.6, 69.2, 66.6, 52.5, 52.3, 43.2, 31.5, 31.4, 30.0, 27.9, 22.2, 14.2.

2R)-2-[(4E)-3-hydroxy-7-[(triphenylmethyl)sulfanyl]hept-4-enamido]hexanoic acid. Methyl (2R)-2-[(4E)-3-hydroxy-7-[(triphenylmethyl)sulfanyl]hept-4-enamido]hexanoate (320 mg, 0.586 mmol, 1.0 equiv.) was dissolved in a 4:1 ratio of THF/water (15 mL). Next was added lithium hydroxide (351 mg, 14.7 mmol, 25 equiv.). The solution was then stirred for 12 hours. The reaction was then diluted with water (10 mL) and then acidified to a pH of 4-5 with $KHSO_4$. The aqueous layer was extracted with ethyl acetate (15 mL) four times. The organic layers were combined and washed with water, brine, dried over anhydrous $Na_2SO_4$, and concentrated in vacuo. Chromatography on $SiO_2$ (ethyl acetate/hexane, 4:6) gave 296 mg (95%) of product as a white solid. $^1H$ NMR (300 MHz, $CDCl_3$, 25° C.) δ (ppm) 7.50-7.15 (m, 15H), 7.03-6.91 (m, 1H), 5.55 (m, 1H), 5.44 (dd, 1H), 4.56 (q, 1H), 4.45 (m, 1H), 2.43 (m, 2H), 2.24 (m, 2H), 2.10 (m, 2H), 1.87 (m, 1H), 1.71 (m, 1H), 1.35-1.26 (m, 4H), 0.91 (t, 3H); $^{13}C$ NMR (75 MHz, $CDCl_3$, 25° C.) δ (ppm) 175.4, 172.5, 145.1, 132.0, 129.7, 129.6, 127.9, 126.7, 69.2, 66.6, 52.5, 43.4, 31.5, 31.4, 30.4, 27.5, 22.3, 13.9.

(2R)-2-[(4E)-7-{[(3E)-6-{[(1R)-1-carboxypentyl]carbamoyl}-5-hydroxyhex-3-en-1-yl]disulfanyl}-3-hydroxyhept-4-enamido]hexanoic acid. Iodine (134 mg, 0.562 mmol, 1.0 equiv.) and sodium acetate (173 mg, 1.12 mmol, 2.0 equiv.) were dissolved in a 10:1 solution of $CH_2Cl_2$/MeOH (10 mL). (2R)-2-[(4E)-3-hydroxy-7-[(triphenylmethyl)sulfanyl]hept-4-enamido]hexanoic acid (280 mg, 0.526 mmol, 1.0 equiv.) was dissolved in a 10:1 solution of $CH_2Cl_2$/MeOH (5 mL) and was added dropwise at 0° C. over 20 minutes to the first solution containing iodine and sodium acetate. This solution was then allowed to stir for 2 hours. The reaction was quenched by adding a saturated sodium thiosulfate ($Na_2S_2O_3$) solution until the reaction mixture turned clear. Then brine (5 mL) was added and the phases were separated. The aqueous layer was extracted with dichloromethane (3×15 mL) and then with ethyl acetate (3×15 mL). The organic layers were combined, dried over $Na_2SO_4$, and concentrated in vacuo. The crude reaction mixture was first purified by Hi-Flash Column (ODS-C18, 3.0×16.5 cm, 50 µm, Yamazen A1-580), 0-20 min 20-100% $ACN/H_2O$ 20 mL/min and the detection wavelength was set at 210 nm. The peak was collected at 8-12 min. Then this peak was injected in the HPLC (Varian ProStar) with the column (Prep-C18, 21.2×250 mm, 10 µm) system, and 40% $ACN/H_2O$ was used to elute the column under the flow rate of 8 mL/min. The wavelength was set at 200 nm to detect the compound and 75 mg of the pure compound was collected at 17-24.5 min. (24.1% yield.) $^1H$ NMR (500 MHz, DMSO, 25° C.) δ (ppm) 5.62 (m, 1H), 5.49 (m, 1H), 4.35 (s, 2H), 2.60 (t, 2H), 2.37 (m, 4H), 1.75 (m, 1H), 1.57 (m, 1H), 1.23 (m, 4H), 0.75 (m, 3H); $^{13}C$ NMR (75 MHz, $CD_3OD$, 25° C.) δ (ppm) 174.2, 172.1, 133.2, 128.9, 69.0, 52.2, 43.3, 37.6, 31.6, 29.4, 27.6, 22.0, 13.0.

methyl (2R)-2-[(4E)-3-hydroxy-7-{[(3E)-5-hydroxy-6-{[(2R)-1-methoxy-1-oxohexan-2-yl]carbamoyl}hex-3-en-1-yl]disulfanyl}hept-4-enamido]hexanoate. Iodine (169 mg, 0.669 mmol, 1.1 equiv.) and sodium acetate (99.7 mg, 1.22 mmol, 2.0 equiv.) were dissolved in a 10:1 solution of $CH_2Cl_2$/MeOH (15 mL). Methyl (2R)-2-[(4E)-3-hydroxy-7-[(triphenylmethyl)sulfanyl]hept-4-enamido]hexanoate (332 mg, 0.608 mmol, 1.0 equiv.) was dissolved in a 10:1 solution of $CH_2Cl_2$/MeOH (5 mL) and was added dropwise at 0° C. over 20 minutes to the first solution containing iodine and sodium acetate. This solution was then allowed to stir for 2 hours. The reaction was quenched by adding a saturated sodium thiosulfate ($Na_2S_2O_3$) solution until the reaction mixture turned clear. Then brine (5 mL) was added and the phases were separated. The aqueous layer was extracted with dichloromethane (3×15 mL) and then with ethyl acetate (3×15 mL). The organic layers were combined, dried over $Na_2SO_4$, and concentrated in vacuo. The crude reaction system was first purified by Hi-Flash Column (ODS-C18, 3.0×16.5 cm, 50 μm, Yamazen A1-580), 0-20 min 20-100% ACN/$H_2O$ 20 mL/min and the detection wavelength was set up at 210 nm. The peak was collected at 12-15 min. Then this peak was injected in the HPLC (Varian ProStar) with the column (Prep-C18, 21.2×250 mm, 10 μm) system, and 50% ACN/$H_2O$ was used to elute the column under the flow rate of 8 mL/min. The wavelength was set up at 200 nm to detect the compound, and 135 mg of the pure compound was collected at 27-32 min. (36.7% yield.) $^1H$ NMR (300 MHz, $CD_2Cl_2$, 25° C.) δ (ppm) 7.11 (d, 1H), 5.71 (m, 1H), 5.58 (dd, 1H), 4.53 (m, 1H), 4.45 (m, 1H), 4.18 (bs, OH), 3.73 (s, 3H), 2.76 (t, 2H), 2.44 (m, 4H), 1.88 (m, 1H), 1.68 (m, 1H), 1.32 (m, 4H), 0.91 (t, 3H); $^{13}C$ NMR (75 MHz, $CD_2Cl_2$, 25° C.) δ (ppm) 173.1, 171.9, 133.3, 128.9, 69.1, 52.2, 52.1, 42.9, 38.2, 31.8, 31.7, 27.5, 22.3, 13.7.

Methyl 2-[(4E)-3-hydroxy-7-[(triphenylmethyl)sulfanyl]hept-4-enamido]-3-methylpentanoate. (E)-3-hydroxy-7-(tritylthio)hept-4-enoic acid (600 mg, 1.43 mmol, 1.0 eqv.) and DL-isoleucine methyl ester (188 mg, 1.43 mmol, 1.0 equiv.) were dissolved in dichloromethane (anhydrous) (40 mL) under Ar. The reaction was cooled to 0° C. and then benzotriazol-1-yl-oxytripyrrolidinophosphonium hexafluorophosphate (PyBOP) (821 mg, 1.58 mmol, 1.1 equiv.) was added. The solution stirred for 10 min and then DIPEA (0.781 mL, 4.30 mmol, 3.0 equiv.) was added. The reaction was allowed to warm to 25° C. and stirred for 14 hours. It was then quenched with a saturated $NH_4Cl$, extracted with dichloromethane (3×20 mL), washed with brine, dried over $Na_2SO_4$, and then concentrated in vacuo. Chromatography on $SiO_2$ (ethyl acetate/hexane, 3:7) gave 457 mg (58%) of product as a white solid. $^1H$ NMR (300 MHz, $CDCl_3$, 25° C.) δ (ppm) 7.44-7.15 (m, 15H), 6.48 (m, 1H), 5.54 (m, 1H), 5.45 (dd, 1H), 4.75-4.58 (m, 1H), 4.43 (m, 1H), 3.9 (m, OH), 3.74 (s, 3H), 2.40 (m, 2H), 2.22 (q, 2H), 2.09 (m, 2H), 1.90 (m, 1H), 1.39 (m, 1H), 1.16 (m, 1H), 0.95 (m, 6H); $^{13}C$ NMR (75 MHz, $CDCl_3$, 25° C.) δ (ppm) 172.8, 171.8, 144.9, 132.2, 130.1, 129.5, 127.9, 126.6, 69.2, 66.6, 56.3, 52.2, 43.0, 37.7, 31.5, 31.4, 26.3, 16.3, 11.6.

2-[(4E)-3-hydroxy-7-[(triphenylmethyl)sulfanyl]hept-4-enamido]-3-methylpentanoic acid. Methyl 2-[(4E)-3-hydroxy-7-[(triphenylmethyl)sulfanyl]hept-4-enamido]-3-methylpentanoate (456 mg, 0.836 mmol, 1.0 equiv.) was dissolved in a 4:1 ratio of THF/water (15 mL). Next was added lithium hydroxide (500 mg, 20.9 mmol, 25 equiv.). The solution was then stirred for 12 hours. The reaction was then diluted with water (15 mL) and then acidified to a pH of 4-5 with $KHSO_4$. The aqueous layer was extracted with ethyl acetate (20 mL) four times. The organic layers were combined and washed with water, brine, dried over anhydrous sodium sulfate, and concentrated in vacuo. Chromatography on $SiO_2$ (ethyl acetate/hexane, 4:6) gave 422 mg (95%) of product as a white solid. $^1H$ NMR (300 MHz, $CDCl_3$, 25° C.) δ (ppm) 7.43 (m, 6H), 7.30-7.25 (m, 9H), 7.08-6.79 (m, 1H), 5.55 (m, 1H), 5.46 (m, 1H), 4.67-4.55 (m, 1H), 4.48 (m, 1H), 2.44 (m, 2H), 2.22 (m, 2H), 2.00 (m, 2H), 1.97-1.85 (m, 1H), 1.40 (m, 1H), 1.20 (m, 1H), 0.91 (m, 6H); $^{13}C$ NMR (75 MHz, $CDCl_3$, 25° C.) δ (ppm) 175.8, 172.3 145.1, 132.0, 130.3, 129.6, 127.9, 126.6, 69.3, 66.5, 56.5, 43.2, 37.3, 31.4, 29.7, 26.3, 16.8, 11.6.

2-[(4E)-7-{[(3E)-6-[(1-carboxy-2-methylbutyl)carbamoyl]-5-hydroxyhex-3-en-1-yl]disulfanyl}-3-hydroxyhept-4-enamido]-3-methylpentanoic acid. Iodine (200 mg, 0.788 mmol, 1.0 equiv.) and sodium acetate (129 mg, 1.57 mmol, 2.0 equiv.) were dissolved in a 10:1 solution of $CH_2Cl_2$/MeOH (15 mL). 2-[(4E)-3-hydroxy-7-[(triphenylmethyl)sulfanyl]hept-4-enamido]-3-methylpentanoic acid (420 mg, 0.788 mmol, 1.0 equiv.) was dissolved in a 10:1 solution of $CH_2Cl_2$/MeOH (5 mL) and was added dropwise at 0° C. over 20 minutes to the first solution containing iodine and sodium acetate. This solution was then allowed to stir for 2 hr. The reaction was quenched by adding a saturated sodium thiosulfate ($Na_2S_2O_3$) solution until the reaction mixture turned clear. Then brine (5 mL) was added and the phases were separated. The aqueous layer was extracted with dichloromethane (3×15 mL) and then with ethyl acetate (3×15 mL). The organic layers were combined, dried over $Na_2SO_4$, and concentrated in vacuo. The crude reaction mixture was first purified by Hi-Flash Column (ODS-C18, 3.0×16.5 cm, 50 μm, Yamazen A1-580), 0-20 min 20-100% ACN/$H_2O$ 20 mL/min and the detection wavelength was set up at 210 nm. The peak was collected at 8-12 min. Then this peak was injected in the HPLC (Varian ProStar) with the column (Prep-C18, 21.2×250 mm, 10 um) system, and 40% ACN/$H_2O$ was used to elute the column under the flow rate of 8 mL/min. The wavelength was set up at 200 nm to detect the compound, and 63 mg of the pure compound was collected at 15.5-21 min. (13.9% yield.) $^1H$ NMR (300 MHz, $CD_3OD$, 25° C.) δ (ppm) 5.75 (m, 1H), 5.61 (m, 1H), 4.57-4.40 (m, 2H), 3.37 (s, OH), 2.75 (t, 2H), 2.47 (m, 4H), 2.01-1.88 (m, 1H), 1.60-1.40 (m, 1H), 1.27 (m, 1H), 0.96 (m, 6H) <ju062112> Exp 1; $^{13}C$ NMR (75 MHz, $CD_3OD$, 25° C.) δ (ppm) 173.5, 172.0, 133.3, 129.0, 69.0, 56.7, 43.1, 37.6, 37.0, 31.6, 26.4, 15.3, 10.7.

Methyl 2-[(4E)-3-hydroxy-7-{[(3E)-5-hydroxy-6-[(1-methoxy-3-methyl-1-oxopentan-2-yl)carbamoyl]hex-3-en-1-yl]disulfanyl}hept-4-enamido]-3-methylpentanoate.
Iodine (134 mg, 0.529 mmol, 1.0 equiv.) and sodium acetate (86.8 mg, 1.06 mmol, 2.0 equiv.) were dissolved in a 10:1 solution of $CH_2Cl_2$/MeOH (10 mL). Methyl 2-[(4E)-3-hydroxy-7-[(triphenylmethyl)sulfanyl]hept-4-enamido]-3-methylpentanoate (289 mg, 0.529 mmol, 1.0 equiv.) was dissolved in a 10:1 solution of $CH_2Cl_2$/MeOH (5 mL) and was added dropwise at 0° C. over 20 minutes to the first solution containing iodine and sodium acetate. This solution was then allowed to stir for 2 hours. The reaction was quenched by adding a saturated sodium thiosulfate ($Na_2S_2O_3$) solution until the reaction mixture turned clear. Then brine (5 mL) was added and the phases were separated. The aqueous layer was extracted with dichloromethane (3×15 mL) and then with ethyl acetate (3×15 mL). The organic layers were combined, dried over $Na_2SO_4$, and concentrated in vacuo. The crude reaction mixture was first purified by Hi-Flash Column (ODS-C18, 3.0×16.5 cm, 50 μm, Yamazen A1-580), 0-20 min 20-100% ACN/$H_2O$ 20 mL/min and the detection wave length was set at 210 nm.

The peak was collected at 12-15 min. Then this peak was injected in the HPLC (Varian ProStar) with the column (Prep-C18, 21.2×250 mm, 10 μm) system and 50% ACN/H$_2$O was used to elute the column under the flow rate of 8 mL/min. The wavelength was set at 200 nm to detect the compound and 52 mg of the pure compound was collected at 25-31 min. (16.3% yield.) $^1$H NMR (300 MHz, CD$_2$Cl$_2$, 25° C.) δ (ppm) 6.60 (s, NH), 5.74 (m, 1H), 5.65 (dd, 1H), 4.70-4.54 (m, 1H), 4.53-4.43 (s, 1H), 3.75, (s, 3H), 3.70 (bs, OH), 2.78 (t, 2H), 2.56-2.35 (m, 4H), 1.90 (m, 1H), 1.45 (m, 1H), 1.23 (m, 1H), 0.99-0.89 (m, 6H); $^{13}$C NMR (75 MHz, CD$_2$Cl$_2$, 25° C.) δ (ppm) 172.4, 171.6, 133.1, 129.2, 69.2, 56.4, 52.2, 42.6, 38.3, 37.7, 31.7, 26.2, 15.3, 11.3.

(2R)-1-methoxy-4-(methylsulfanyl)-1-oxobutan-2-aminium chloride. Chlorotrimethylsilane (8.51 mL, 67.02 mmol, 2 equiv.) was added dropwise to a round bottom flask containing D-methionine hydrochloride (5.00 g, 33.51 mmol, 1.0 equiv.) under Ar. Then anhydrous methanol (50 mL) was added, and the solution was stirred for 22 hours. The contents of the flask were then concentrated in vacuo. $^1$H NMR (300 MHz, D$_2$O, 25° C.) δ (ppm) 4.24 (t, 1H), 3.79 (s, 3H), 2.62 (t, 2H), 2.33-2.09 (m, 2H), 2.05 (s, 3H); $^{13}$C NMR (125 MHz, D$_2$O, 25° C.) δ (ppm) 170.51, 53.67, 51.72, 28.72, 28.44, 13.87.

1-methoxy-3-methyl-1-oxopentan-2-aminium chloride. Chlorotrimethylsilane (1.93 mL, 15.25 mmol, 2 equiv.) was added dropwise to a round bottom flask containing DL-Isoleucine hydrochloride (1.0 g, 7.62 mmol, 1.0 equiv.) under Ar. Then anhydrous methanol (20 mL) was added and the solution was stirred for 22 hours. The contents of the flask were then concentrated in vacuo. $^1$H NMR (300 MHz, D$_2$O, 25° C.) δ (ppm) 4.05 (m, 1H), 3.76 (s, 3H), 2.15-1.94 (m, 1H), 1.49-1.32 (m, 1H), 1.32-1.16 (m, 1H), 0.95-0.81 (m, 6H); $^{13}$C NMR (75 MHz, D$_2$O, 25° C.) δ (ppm) 170.20, 57.22, 53.40, 35.50, 24.87, 14.01, 10.68.

(2R)-1-methoxy-1-oxohexan-2-aminium chloride. Chlorotrimethylsilane (1.93 mL, 15.247 mmol, 2 equiv.) was added dropwise to a round bottom flask containing D-norleucine hydrochloride (1.00 g, 7.62 mmol, 1.0 equiv.) under Ar. Then anhydrous methanol (20 mL) was added and the solution was stirred for 22 hr. The contents of the flask were then concentrated in vacuo. $^1$H NMR (300 MHz, D2O, 25° C.) δ (ppm) 4.06 (t, 1H), 3.76 (s, 3H), 1.95-1.75 (m, 2H), 1.35-1.27 (m, 4H), 0.79 (t, 3H); $^{13}$C NMR (75 MHz, D2O, 25° C.) δ (ppm) 171.0, 53.4, 52.9, 29.3, 26.1, 21.4, 12.8.

Methyl (2S)-2-{[(9H-fluoren-9-ylmethoxy)carbonyl]amino}-3-[(triphenylmethyl)sulfanyl]propanoate. Chlorotrimethylsilane (2.17 mL, 15.07 mmol, 2 equiv.) was added dropwise to a round bottom flask containing (2S)-2-{[(9H-fluoren-9-ylmethoxy)carbonyl]amino}-3-[(triphenylmethyl)sulfanyl]propanoic acid (5.00 g, 8.54 mmol, 1.0 equiv.) under Ar. Then anhydrous methanol (40 mL) was added and the solution was stirred for 22 hr. The contents of the flask were then concentrated in vacuo.

Methyl (2R)-2-amino-2-[(triphenylmethyl)sulfanyl]acetate. (9H-fluoren-9-yl)methyl (R)-(methoxycarbonyl)(tritylthio)methylcarbamate (450 mg, 0.750 mmol, 1 equiv.) was dissolved in anhydrous acetonitrile (10 mL). Then, excess diethylamine (2 mL) was added and the solution was stirred for 2 hours. The contents of the flask were concentrated in vacuo. The solid was re-dissolved in chloroform and the solvent was removed in vacuo. $^1$H NMR (300 MHz, CDCl$_3$, 25° C.) δ (ppm) 7.50-7.20 (m, 15H), 3.66 (s, 3H), 3.24 (t, 1H), 2.63 (m, 1H), 2.51 (m, 1H), 2.00-1.42 (bs, NH$_2$); $^{13}$C NMR (125 MHz, CDCl$_3$, 25° C.) δ (ppm) 171.0, 144.8, 129.1, 128.0, 126.8, 66.5, 53.8, 52.1, 37.0.

Synthesis of Cdp4-6 and Cpd4'-6'. Derivatives Cpd4, Cpd5, and Cpd6, which have different aliphatic side chain amino acids, were synthesized by a similar sequence using the β-hydroxy acid and PyBop coupling agent to attach the amino acid followed by deprotection of the methyl esters with lithium hydroxide to produce 14, 15, and 16 (FIG. 3). Then carboxylic acids 14, 15, 16 were treated in iodine and sodium acetate conditions to yield disulfide products Cpd4 (25.4%), Cpd5 (32.4%), and Cpd6 (42.4%). The corresponding methyl esters 11, 12, 13 were reacted using similar iodine/sodium acetate conditions to yield the disulfide dimers Cpd4' (52%), Cpd5' (34%), and Cpd6' (15%), respectively.

Example 3

In Vitro HDAC Inhibitor Activity

The purified compounds of all fragments and natural product derivatives were evaluated for inhibitory effects on three different classes of HDAC proteins (class I, IIa, and IIb). The natural products FK228, SAHA, TDP-A, and TDP-B were used as a positive control. All activity was determined by using a fluorescence-based in vitro assay. Class I HDAC proteins that were evaluated were HDAC1, HDAC2, HDAC3, HDAC8, HDAC4, and HDAC6. Class IIa HDAC protein were HDAC4 and the Class IIb HDAC protein were HDAC6.

HDAC-Glo™ I/II Assay and Screening System (Promega) was used to determine the HDAC inhibitory activity. Recombinant human HDAC1, HDAC2, HDAC3, HDAC4, HDAC6 and HDAC8 were purchased from BPS Bioscience Inc. The inhibitory activities of the test compounds against recombinant HDAC were performed according to reagent suppliers' protocols.

All test compounds were firstly dissolved in DMSO to make 10 mM stock solution. A certain amount of stock solution was diluted to 1 mM by DMSO and then reduced by tris(2-carboxyethyl)phosphine hydrochloride (TCEP) in a molar ration of 1:1.5 for 20 min at ambient temperature prior to being assayed. After reduction, a series of fivefold dilutions of each reduced compound were prepared with HDAC-Glo buffer and 25 μL of each dilution was added into a well on a 96-well plate. HDAC enzymes were diluted to the desired concentrations with HDAC-Glo buffer and 25 μL of each diluted enzyme was dispensed into a well to mix with 25 μL of testing compound at room temperature for 30-60 seconds. After the reaction mixture had been incubated at room temperature for 1 hour, 50 μL of HDAC-Glo reagent was added to each reaction well and mixed up for 30-60 seconds. Finally, the plate was incubated at room temperature for an additional 30 minutes before the luminescence was measured on a Synergy HT plate reader (Bio-Tek). The luminescence intensity data were analyzed using GraphPad Prism 5 (GraphPad Software). In the absence of any test compound, the luminescence intensity (I100) in each data set was defined as 100% activity. In the absence of both of HDAC enzymes and test compound, the luminescence intensity (I0) in each data set was defined as 0% activity. The relative activity (%) in the presence of each compound was calculated according to the following equation: % activity=(I−I0)/(I100−I0), where I=the luminescence intensity if a compound is present in the reaction. Experiments were performed in triplicate and the calculated mean values were used for plotting.

The results of the enzyme assays are shown in Table 2. The first group designed and analyzed was the natural product derivatives TDC1, TDC2, and TDC3, which had different aliphatic groups on the alcohol. TDC1 had the largest group (benzoyl), while TDC3 had the smallest chain (acetyl group), and TDC2 had a medium chain attached (ethyl formate). All showed similar HDAC inhibition compared to the natural products to all class of HDAC proteins (HDAC I, IIa, and IIb). TDC3 had the greatest inhibition of the three derivatives. A large group like a benzoyl group on the hydroxyl handle in TDC1 nearly abolished selectivity toward Class IIb isofrom (HDAC4). This would be most likely due to the cap group interacting with the protein surface outside the catalytic pocket.

Next, with the linker and ZBG groups very specific for binding in our natural products (TDP-A, TDP-B, and FK228) the cap group was investigated. The first fragment designed was TDF1, which had the same linker and ZBG as the natural products. TDF1 had very potent inhibitory activity to HDAC1 and HDAC2 (nanomolar concentrations) while exhibiting very poor activity against Class IIa (HDAC4) and IIb (HDAC 6). A t-butyl group was added to the carboxylic acid cap end (TDF1t) to increase the selectivity for HDAC1 and HDAC2 inhibition, but this change resulted in increased inhibition of HDAC6 (class IIa) by 4.5-fold.

Referring to the initial results with the simple linker and ZBG, two amino acids (methione first, cysteine second) were added in sequence for the next four fragments (TDF2, TDF2m, TDF3, and TDF3m). In general HDAC inhibition for this set of fragments was similar to that observed for TDF1. Interestingly, while TDF2 and TDF2m showed some inhibitory activity toward the Class II HDAC isoform HDAC6 (high micromolar), TDF3 and TDF3m showed no inhibitory activity. TDF3 and TDF3m are closed ring fragments, as it was stipulated that a closed ring would give better selectivity than the previous linear fragments due to reports from Ganesan et al. (REF) describing that the cysteine sulfur is important for its role in packaging the peptide for cellular uptake and is equally important as the sulfur that binds to zinc.

The last set of compounds that were designed was based on the first fragment TDF1, which had the best selectivity for class I HDACs. TDF4, TDF5, and TDF6 tested the different aliphatic side chains to see the importance between the natural product side chains (TDP-A: R=SCH3, TDP-B: R=CH2CH3) with norleucine and valine. All of the methyl esters (TDF4m, TDF5m and TDF6m) were about 10-fold less active toward all class I HDACs.

In summary, TDC3 had the greatest inhibition for the natural product derivatives, and the fragments TDF1t and TDF5 showed similar inhibition. All fragments showed highly selective inhibition of Class I over Class II HDACs. All fragments showed 100-1000-fold better selectivity than SAHA for HDAC1 to HDAC8 ratio. The inhibition of HDAC4 or HDAC6 was dramatically less, which means that the novel compounds are more specific inhibitors for HDAC1-3 and HDAC8 and may show reduced in vivo toxicity.

TABLE 2

HDAC inhibitory activity ($IC_{50}$ in μM)

| Compound | Class I HDAC | | | | Class IIb HDAC | Class IIa HDAC | Class I selectivity | Class I vs. Class IIa |
| | $IC_{50}$ of HDAC1 | $IC_{50}$ of HDAC2 | $IC_{50}$ of HDAC3 | $IC_{50}$ of HDAC8 | $IC_{50}$ of HDAC4 | $IC_{50}$ of HDAC6 | Ratio HDAC 1/HDAC8 | Ratio HDAC 1/HDAC6 |
| --- | --- | --- | --- | --- | --- | --- | --- | --- |
| SAHA | 0.0207 | 0.0694 | 0.1697 | 7.04 | 116.73 | 0.1794 | 0.01399 | 0.12 |
| FK228 | 0.0038 | 0.0183 | 0.0187 | 1.48 | 2.37 | 0.5075 | 0.00035 | 0.0075 |
| TDP-B | 0.0022 | 0.0256 | 0.0482 | 10.90 | 27.93 | 0.6503 | 0.00026 | 0.0034 |
| TDP-A | 0.0024 | 0.0081 | 0.0077 | 8.44 | 20.48 | 0.2734 | 0.00065 | 0.0088 |
| TDC1 | 0.0109 | 0.0510 | 0.6398 | 3.67 | ~500 | 5.49 | 0.00252 | 0.0020 |
| TDC2 | 0.0096 | 0.0370 | 0.7010 | 4.33 | 134.57 | 1.49 | 0.00096 | 0.0064 |
| TDC3 | 0.0027 | 0.0442 | 0.2452 | 10.03 | 40.48 | 1.34 | 0.00006 | 0.0020 |
| TDF1, Cpd3 | 0.0068 | 0.0443 | 0.5791 | 41.91 | >1000 | 165.94 | 0.00020 | 0.00004 |
| TDF1t, Cpd3' | 0.0044 | 0.0245 | 0.5401 | 34.21 | ~500 | 41.31 | 0.00016 | 0.0001 |
| TDF2, Cpd2 | 0.0095 | 0.0902 | 0.8098 | 27.03 | >1000 | 166.37 | 0.00043 | 0.00006 |
| TDF2m, Cpd2' | 0.0109 | 0.0726 | 0.3528 | 22.31 | >1000 | 46.32 | 0.00017 | 0.00024 |
| TDF3, Cpd1 | 0.0229 | 0.0875 | 0.8186 | 62.85 | >1000 | >1000 | 0.00036 | N/A |
| TDF3m, Cpd1' | 0.0125 | 0.0942 | 0.6226 | 63.03 | >1000 | >1000 | 0.00028 | N/A |
| TDF4, Cpd4 | 0.0039 | 0.0365 | 0.7135 | 43.89 | >1000 | >1000 | 0.00003 | N/A |
| TDF4m, Cpd4' | 0.0303 | 2.12 | 0.0971 | 116.90 | >1000 | >1000 | 0.00061 | N/A |
| TDF5, Cpd5 | 0.0026 | 0.0459 | 0.8393 | 49.38 | >1000 | >1000 | 0.00002 | N/A |
| TDF5m, Cpd5' | 0.0265 | 1.66 | 0.1241 | 133.30 | >1000 | >1000 | 0.00159 | N/A |
| TDF6, Cpd6 | 0.0035 | 0.1106 | 0.0416 | 16.63 | >1000 | >1000 | 0.00003 | N/A |
| TDF6m, Cpd6' | 0.0302 | 1.93 | 0.1002 | 100.41 | >1000 | >1000 | N/A | N/A |

Example 4

In Vivo HDAC Inhibitor Activity

The compounds will be tested for their ability to enter cells and inhibit intracellular HDAC activity. HCT-116 cells will be treated with increasing concentrations of a compound, SAHA (positive control), or vehicle alone for 4 hrs, or with a single (IC50) concentration for increasing lengths of time. Changes in histone acetylation will be measured by Western blot as described before (Shi, et al. *Drug Discoveries and Therap.* 2013, 7, 129; Kelly, et al. *J. Clin. Oncol.* 2005, 23, 3923; Plumb, et al. *Mol. Cancer Therap.* 2003, 2, 721; and Zhaoyang, et al. *Journal of Pharmaceutical and Biomedical Analysis* 2000, 22, 33). The same concentrations and dosing schedule will also be used to simultaneously measure in vitro anticancer activities against a tumor cell line as detailed below. Together, these data will allow the determination of whether intracellular inhibition of HDAC activity correlates with anticancer activity.

Example 5

Anti-Proliferative Activity

The anti-proliferative activities of the compounds described above were tested against colon (HCT-116), cervical (HeLa), and renal (RFX393) tumor cell lines in an MTT assay using the natural products FK228, SAHA, TDP-A and TDP-B as positive controls.

The cytotoxicity of the compounds against the HeLa (cervical cancer, ATCC), RXF393 (renal cancer, ATCC) and HCT-116 (colon cancer, ATCC), SKOU-3 (ovarian cancer, ATCC), DU-145 (prostate cancer, ATCC), MDA-MB-231 (breast cancer, ATCC), and COLO-205 (colon cancer, ATCC) cell lines was determined using the MTT assay as previously described (REF). Briefly, the tumor cells (1×10$^4$ cells/well) were seeded in 96-well microtiter plates and incubated for 24 h at 37° C. Following incubation, the media was replaced with fresh media containing the above compounds at concentrations ranging from 1 μM to 1 pM diluted in DMSO and incubated for an additional 48 h. Drugs were run in duplicate or triplicate and control cells received fresh media with DMSO concentration equivalent to the treatment groups. Thereafter, the wells were washed twice with warm PBS and incubated for another 4 hours with RPMI 1640 media containing 250 μg/mL of MTT. After aspirating the culture medium, 200 μL of DMSO was added to dissolve the precipitate and the resulting solution was measured for absorbance at 570 nm with a reference wavelength of 690 nm using a microplate reader (Infinite M200 Pro TECAN). Results were used to determine the growth inhibition—50% (GI50) of each drug.

Surprisingly, modifications of TDP-A (TDC1, TDC2, and TDC3) increased the GI50 by 100 to 1000 fold despite having similar HDAC inhibition profiles (Table 3). The synthetic compounds TDF1t, TDF3, TDF3m, and TDF5 had GI50 values 8-fold lower (GI50 values of 0.5 μM, 0.6 μM, 0.4 μM and 0.5 μM, respectively) against all three tumor cell lines than SAHA, a synthetic analogue known to have GI50 values in the range of 2.5-3 μM. By contrast, TDF2, TDF2m, TDF4 and TDF6 had moderate levels of anti-proliferative activity with GI50 values within 2 μM, 6 μM, 5 μM and 4 μM, respectively, against all three tumor cell lines. Since different tumor cells are known to have different sensitivity to HDAC inhibitor the top four fragments (TDC1, TDF1t, TDF3m, and TDF5) were tested against four other tumor cell lines derived from ovavian, prostate, breast and colon cancers. In general, the results of these studies were consistent with those obtained using the other tumor cell lines. Specifically, TDP-A showed the strongest antiproliferative activity and all of the fragments showing great inhibitory activity than SAHA (Table 4).

TABLE 3

Antiproliferative Activity (GI$_{50}$ in μM).

| Compound | Colon HCT-116 | Cervical HeLa | Renal RFX393 |
|---|---|---|---|
| SAHA | 2.7 | 2.8 | 2.5 |
| FK228 | 0.0012 | 0.0013 | 0.0012 |
| TDP-B | 0.002 | 0.0021 | 0.0022 |
| TDP-A | 0.00093 | 0.00036 | 0.00047 |
| TDC1 | 0.0247 | 0.2248 | 0.0351 |
| TDC2 | 0.056 | 0.1412 | 0.0510 |
| TDC3 | 0.1205 | 0.332 | 0.1067 |
| TDF1 = Cpd3 | 2.1 | 1.4 | 1.1 |
| TDF1t = Cpd3' | 0.3 | 0.2 | 0.4 |
| TDF2 = Cpd2 | 1.4 | 1.1 | 1.9 |
| TDF2m = Cpd2' | 2.3 | 2.6 | 5.9 |
| TDF3 = Cpd1 | 0.3 | 0.6 | 0.2 |
| TDF3m = Cpd1' | 0.2 | 0.4 | 0.3 |
| TDF4 = Cpd4 | 3.7 | 4.8 | 4.1 |
| TDF4m = Cpd4' | 31 | 20.1 | 32.1 |
| TDF5 = Cpd5 | 0.4 | 0.4 | 0.5 |
| TDF5m = Cpd5' | 32.6 | 30.2 | 40.1 |
| TDF6 = Cpd6 | 1.3 | 3.6 | 3.1 |
| TDF6m = Cpd6' | 28.4 | 25.6 | 31.7 |

* Individual values were derived from the average of triplicate experiments with standard error within 20% margin.

TABLE 4

Antiproliferative Activity (GI$_{50}$ in μM).

| Compound | Ovarian SKOV-3 | Prostate DU-145 | Breast MDA-MB-231 | Colon COLO-205 |
|---|---|---|---|---|
| SAHA | 1.5 | 2 | 1.5 | 0.5 |
| TDP-A | 0.002 | 0.001 | 0.003 | 0.0035 |
| TDC1 | 0.03 | 0.08 | 0.04 | 0.07 |
| TDF1t = Cpd3' | 0.5 | 0.6 | 0.5 | 0.8 |
| TDF3m = Cpd1' | 0.5 | 0.3 | 0.6 | 0.9 |
| TDF5 = Cpd5 | 0.7 | 0.6 | 0.5 | 0.9 |

* Individual values were derived from the average of triplicate experiments with standard error within 20% margin.

Example 6

In Vivo Antitumor Activity

The antitumor activity of compounds will be assessed in both intact murine tumor models and human tumor xenograft models in nude mice. Tumor models will include a colorectal cancer model. The drug testing dosage (starting with one-fifth of MTD) and IV injection will all depend on the assay results detailed in Example 4. The efficacy value will be calculated with statistical analyses.

For the intact model, the 4T1 murine breast carcinoma cell model will be used in wild type BALB/c mice. This tumor is metastatic when injected into BALB/c mice, with spontaneous metastasis to the lung, liver, lymph nodes, and brain. 4T1 cells (1×10$^4$ in 50 μL RPMI media) will be injected into the abdominal mammary gland of female BALB/c mice 98-12 weeks old).

For the xenograft model, studies will use human tumor xenografts in nude BALB/c mice to determine the applicability of the results to cancer patients. Groups of 10 tumor-bearing wild type or BALB/c nude mice will be injected subcutaneously (1×10$^5$ to 1×10$^6$ in 50 μL RPMI media) in one flank with tumor cells. Tumor cells may include HCT-116 colon, U-87MG glioblastoma, MDA-MB-231 breast, RXF393 kidney, and SKOV-3 ovarian tumor cells. Primary tumor growth will be monitored daily by palpation with the total tumor volume being determined using caliper measurements. Tumor volume will be calculated using the formula W×L$^2$/2, wherein L is the major axis of the tumor and W is the minor axis. Once palpable tumors appear, animals will be given daily intraperitoneal injections of 50 or 100 μg/kg of one compound. For control, mice will receive vehicle only or 50 μg/kg of SAHA, which has been shown to be an effective non-toxic antitumor dose. Tumor size and animal weights (as a measure of drug toxicity) will be measured twice weekly until significant morbidity begins to appear. At this time, final tumor size and animal weight will be measured, animals sacrificed, and tumors removed and snap frozen in liquid nitrogen for later analysis of histone acetylation by Western blot. In the event that tumors completely regress upon treatment, the ability of the HDAC inhibitors to inhibit histone acetylation in mice can be assessed in blood cells as described in mouse and human trials of other HDAC inhibitors.

Example 7

Maximum Tolerated Dose (MTD) and Solubility

Synthetic compounds demonstrated significantly higher MTD levels than the natural products.

BALB/c mice were purchased from The Jackson Laboratory (Bar Harbor, Me.) and used between 7 and 10 weeks of age. Mice were housed in a conventional animal vivarium and were given free access to food and water. All studies and procedures were approved by the Animal Care and Use Committee of the University of Wisconsin, Milwaukee.

Each animal was initially weighed using a digital scale and then intraperitoneally (IP) injected with the compounds (listed in Table 2). A single mouse was given a single IP dose of 200 mg/kg, body weight, a second mouse received a dose of 100 mg/kg and a third mouse received a single dose of 50 mg/kg. The mice were observed and weighed every other day for a period of 2 weeks. They were euthanized if they lost more than 20% of their body weight or if there were other signs of significant toxicity. If none of the mice survived with the first three doses, the next 3 dose levels (100 mg/kg, 50 mg/kg, and 25 mg/kg; or 25 mg/kg, 12.5 mg/kg, and 6.25 mg/kg; or 12.5 mg/kg, 6.25 mg/kg, and 3.125 mg/kg) were tested in a similar manner. This process was repeated until a tolerated dose was found, and the MTD value was determined.

To determine the MTD in vivo, the compounds listed above were injected intraperitoneally into BALB/c mice and morbidity and mortality were monitored over two weeks. The parental compounds TDP-A, TDP-B and FK228 were used as positive controls and showed very high toxicity with the animals only being able to tolerate doses of 6.25 mg/kg for both TDP-A and TDP-B and 3.25 mg/kg for FK228 (Table 5). This is due to the natural products inhibiting all types of histones. By contrast, the synthetic compounds were found to be much less toxic to the animals with a MTD of more than 200 mg/kg for all except natural product derivatives TDC1 and TDC2. Solubility increased for all fragments that contained an acidic carboxylic acid group (Table 5). Generally, the smaller molecules were much more soluble as well. In particular, three compounds, Cpd1', Cpd3', and Cpd5, were found to be especially promising based on in vitro studies detailed above and on the fact that they were all much less toxic than the parental TDPs with MTD values greater than 200 mg/kg.

TABLE 5

Solubility and MTD (mg/kg).

| Compound | Solubility | MTD (toxicity in healthy BALB/c mice in mg/kg) |
|---|---|---|
| SAHA | Not soluble | >200 |
| FK228 | Partially soluble | 3.125 |
| TDP-B | Not soluble | 6.25 |

TABLE 5-continued

Solubility and MTD (mg/kg).

| Compound | Solubility | MTD (toxicity in healthy BALB/c mice in mg/kg) |
|---|---|---|
| TDP-A | Not soluble | 6.25 |
| TDC1 | Not soluble | 50 |
| TDC2 | Not soluble | 12.5 |
| TDC3 | Not soluble | >200 |
| TDF1 = Cpd3 | Soluble | >200 |
| TDF1t = Cpd3' | Mostly soluble | >200 |
| TDF2 = Cpd2 | Soluble | >200 |
| TDF2m = Cpd2' | Partially soluble | >200 |
| TDF3 = Cpd1 | Soluble | >200 |
| TDF3m = Cpd1' | Partially soluble | >200 |
| TDF4 = Cpd4 | Mostly soluble | >200 |
| TDF4m = Cpd4' | Soluble | >200 |
| TDF5 = Cpd5 | Mostly soluble | >200 |
| TDF5m = Cpd5' | Soluble | >200 |
| TDF6 = Cpd6 | Soluble | >200 |
| TDF6m = Cpd6' | Soluble | >200 |

* 10 mg/mL cpd in 20% DMSO/saline and in healthy BALB/c mice, IP. Individual values were derived from the average of triplicate experiments with standard error within 20% margin.

Example 8

In Vivo Pharmacokinetics and Metabolism

To obtain pharmacokinetic and metabolic data, groups of 12 BALB/c mice will be given single intraperitoneal (ip) injections a compound at 100 mg/kg body weight. Blood samples will be collected from individual mice at 0 (baseline), 1, 2, 3, 4, 5, 6, 8, 10, 12, 18, and 24 hrs. The serum concentration of the drug and metabolite levels will be analyzed by liquid chromatography-mass spectrometry using a LCMS-8040 mass spectrometer. Pharmacokinetic parameters will be determined by noncompartmental methods (Sandhu, et al. Drug Metab. Letters, 2007, 1, 153).

Example 9

The HDAC Inhibitor TSA Enhances Memory

Figure 8A:
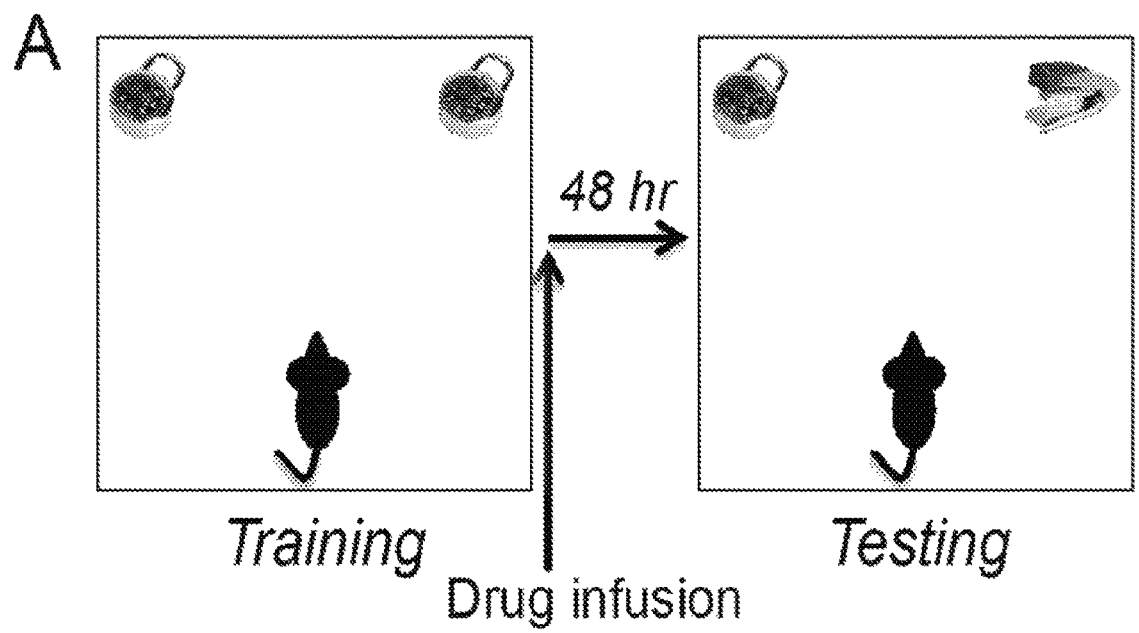
FIG. 8A is an illustration of the object recognition (OR) test.
Figure 8B:
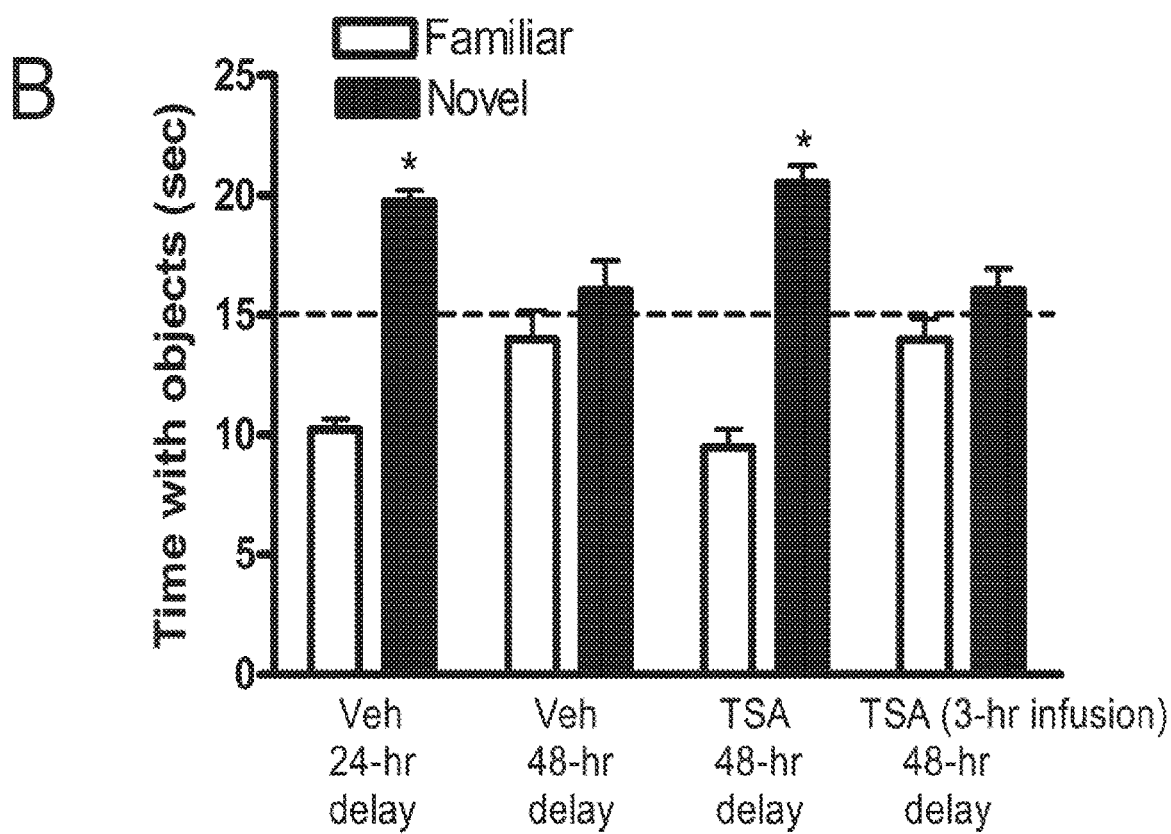
FIG. 8B is a graph of time with objects showing that vehicle-treated mice forget the objects within 48 hours, and mice treated with the HDAC inhibitor TSA spent more time than chance (15 sec) with the novel object 48 hours after training, showing that TSA enhanced memory formation.

The HDAC inhibitor trichostatin-A (TSA) enhances object recognition (OR) memory formation in adult mice (Zhao et al. Proc. Natl. Acad. Sci. USA 2010, 107, 5605-10). Mice were first required to accumulate 30 s exploring 2 identical objects in an open arena (FIG. 8A). Immediately after training, mice received a single treatment with vehicle or the HDACi trichostatin-A (TSA; 16.5 mM). This post-training treatment allowed the pinpointing of effects of compounds on memory consolidation, which occurs within 3 h of the learning experience. Forty-eight h after treatment, mice explored 1 novel and 1 familiar object (FIG. 8A). Because mice are inherently drawn to novelty, mice that remember the familiar object spend significantly more time than chance (15 s) exploring the novel object. Vehicle-treated mice exhibited intact object recognition memory 24 h after training, but not 48 h after training (FIG. 8B). In contrast, mice treated with TSA displayed completely intact object recognition memory 48 h after training (FIG. 8B), demonstrating that the HDACi enhanced object recognition memory formation and rendered this memory more persistent than normal. This effect was specific to formation of object recognition memory, as indicated by the fact that delaying TSA treatment for 3 h after training did not enhance memory (FIG. 8B).

Example 10

Figure 9:
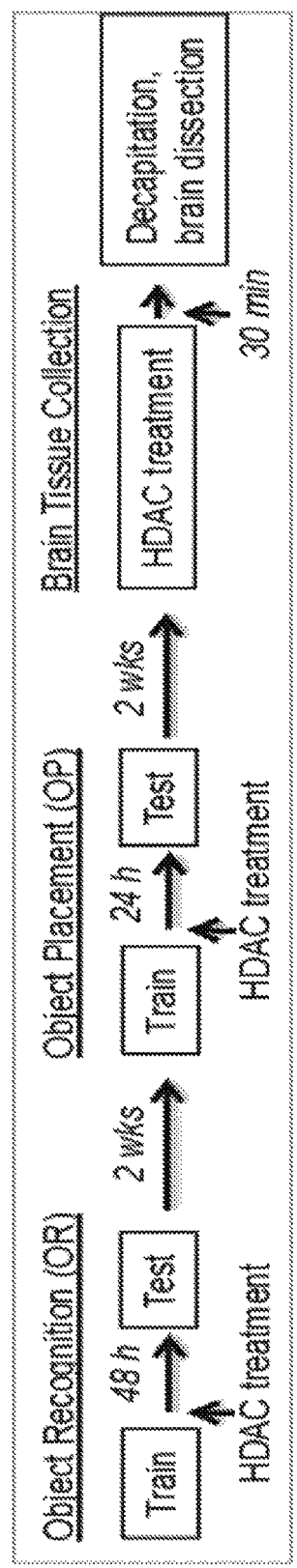
FIG. 9 is a schematic illustration of the timing of behavioral testing and tissue collection for object placement (OP) and object recognition (OR).

Examination of the Ability of HDAC Inhibitors to Enhance Object Recognition and Spatial Memory in Mice C57BL/6 mice will receive training in two memory tasks, object recognition and object placement (OP). For example, ten week-old male mice may be used. OP uses the same apparatus and general procedure as OR, but during testing, 1 training object moves to a lower corner of the box instead of being replaced with a new object (Boulware et al. J. Neurosci. 2013, 33, 15184-94.). OR and OP will be tested using post-training delays (48 h and 24 h, respectively because OP memory decays faster than OR memory) at which vehicle-infused mice do not remember the training objects (FIG. 9) to allow the observation of HDACi-induced memory enhancements.

Mice will be trained in the OR and OP tasks, and then immediately receive an intraperitoneal (i.p.) injection of vehicle or one of the HDAC inhibitors at doses of 50, 100, or 150 µg/kg. As a positive control, another group of mice will be injected with 0.6 g/kg TSA. Groups of mice will be tested for each HDAC inhibitor. For example, 5 groups of mice (n=15/group, n=75/expt) may be tested for each of 3 HDAC inhibitors for a total of 225 mice.

Memory will be tested 48 hours later in OR and 24 hours later in OP, at which point the time spent with each object will be recorded; more time than chance (15 s) with the novel/moved object indicates intact memory for the familiar/unmoved object. Data will be analyzed with one-sample t-tests to determine if the time spent with the novel/moved object differed from 15 s13. Elapsed time to accumulate 30 s of exploration will be recorded to control for group differences in activity, and analyzed with one-sample t-tests, one-way analysis of variance (ANOVA), and post-hoc tests. Testing in OR and OP will be separated by about 2 weeks to allow any effect of the HDACis to dissipate prior to subsequent testing.

Confirmation of histone deacetylation by HDAC inhibitors. To confirm that the lead compounds exhibit HDACi activity in the brain, brain tissue will be collected about 2 weeks after the completion of OP testing. Mice will be injected with vehicle or a dose of HDAC inhibitor, and then be cervically dislocated and decapitated for collection of fresh brain tissue about 30 min later. Regions of the brain essential for OR and OP memory, including the dorsal hippocampus and medial prefrontal cortex, will be dissected and frozen for later Western blot analysis of histone acetylation. At the 30 min time point, it has been shown that TSA increases the acetylation of histones H3 and H4 in the mouse dorsal hippocampus (Zhao et al. Proc. Natl. Acad. Sci. USA 2010, 107, 5605-10). Acetylation of all 4 core histones (H2A, H2B, H3, H4) will be measured using Western blotting. Western blot data will be analyzed with one-way ANOVA followed by post-hocs tests to compare between groups. ADME studies of effective novel HDACi compounds, as well efficacy testing in memory-impaired aged mice, would be conducted in future studies.

Example 11

Examination of the Types of Memory Affected by the HDAC Inhibitors

To identify the kinds of memory that are influenced by the HDAC inhibitors, memory will be tested in any of the following behavioral tasks: Morris water maze, water-motivated radial arm maze, object recognition, object placement, spatial/object novelty, matrix crossings, reflexes, elevated plus maze, forced swim task, contextual fear conditioning, and inhibitory avoidance.

Morris water maze. This task is designed to test for spatial learning and memory of the sort one would use to navigate in a new city. Briefly, mice must swim in a large circular maze to find a square escape platform located just underneath the surface of the water. Because the mice cannot see the platform, they must navigate to it using spatial cues outside of the maze. Each mouse is run in up to 8 trials per day, with intertrial intervals lasting anywhere from 10-15 seconds to 20 minutes. Several versions of this task are run to test different types of spatial and non-spatial (a control cued task) memory. The apparatus and procedures are described below.

Apparatus: The maze is a circular tank (97 or 180 cm in diameter) filled with water (24+/−2 degrees C.). The water is made opaque by the addition of non-toxic water-soluble paint to obscure the escape platforms. Mice are placed in their home cage under a heat lamp to keep them warm until the next trial.

1) Shaping: Prior to water maze testing, all animals are habituated to the water using a four-trial shaping procedure in which a smaller training ring is inserted inside of the larger testing ring to decrease the total swimming area. Each animal is first placed on a visible platform for 10 sec, and then placed at three progressively further distances from the platform where it is allowed 10 sec to escape onto it. No data are collected during this procedure.

2) Spatial task: Animals are placed into the tank and allowed 120 sec to escape onto a hidden platform. If the animal does not escape within 120 sec, then it is manually placed on the platform and allowed to remain there for 10-15 sec. Each animal is placed in its home cage for an intertrial interval of approximately 20 min. Six trials are conducted on each day. Animals receive one training session/day for 5 consecutive days.

3) Spatial reversal: This task tests how well animals can learn a new platform location. The procedure is identical to the spatial task, except for the location of the hidden platform. Six trials/animal are conducted for 3 consecutive days. The intertrial interval is 20 min.

4) Cued task: This control task tests how well animals can learn to find a platform they can see (so no memory is required for this task, which controls for sensorimotor and motivational aspects of task performance). Animals are required to swim to a visible platform to escape from the water. The visible platform is moved to a different quadrant for each trial of each session. Six trials/animal are conducted for 3 consecutive days.

5) One-day water maze protocol: This protocol allows us to test spatial learning and memory within a single extended test session to enable us to better correlate memory performance and brain function. In this protocol, the spatial and cued tasks are conducted within 3 hours in a single day. Twelve 60 sec spatial trials are conducted (3 blocks of 4 consecutive trials, each block separated by 30 min), followed 30 min later by one spatial probe trial, followed 20 min later by four cued trials. Mice are placed in their home cages in between blocks.

6) Two day water maze protocol: We use this protocol to examine the effects of hormones on memory consolidation. Animals are trained on day 1 for 8 trials (60 sec each) in the spatial version of the water maze. In between trials, the animals are placed in a holding cage for 30-45 seconds.

Immediately or two hours after the completion of testing, animals receive an injection of a vehicle substance or hormone. Twenty-four hours later, animals are returned to the maze for 4 spatial retention trials (no drugs will be administered) and 4 cued trials.

Water-motivated Radial Arm Maze. This modification of the Morris water maze task involves inserting a lucite 8-arm radial arm maze into the water maze (see (Gresack and Frick, 2003, 2004, 2006a)). This maze looks like a wheel with a round central arena from which 8 arms radiate like spokes in a wheel. Four of the 8 arms contain hidden escape platforms at the end and 4 arms never contain escape platforms. Ideally, each animal will visit each arm with a platform only once (the platform is removed once found) and will never visit the arms without platforms. The numbers of errors made into the arms without platforms allow us to measure long-term (reference) memory, whereas the platformed arms allow us to measure short-term (working) memory.

Apparatus: The apparatus consists of a round central arena (constructed of opaque lucite) from which eight clear Plexiglas arms radiate equidistantly. The arms are placed at equal distances around the central arena. Neither the central arena nor the arms are enclosed at the top. All arms are enclosed at the far end. At the ends of the arms are located submerged escape platforms, such that when the animal swims to the end of the arm, it can escape from the water by climbing onto the platform. Each platform is 10×10 cm and is located just underneath the surface of the water. The entire radial arm maze is located in a stainless steel tank, 6 feet in diameter. The tank is filled each day with water at 24±2 degrees C. The water is made opaque by the addition of white nontoxic tempera paint.

Shaping: Shaping involves one session of 5 trials. This procedure very similar to that approved for our standard water maze procedure. For the first 5 trials, all 8 arms are closed and animals are tested within the confines of one of the closed arms. The maximum time for each trial is 20 seconds and the animals are allowed to remain on the platform for 10-15 seconds at the completion of each trial. The intertrial interval is about 1 minute. On the first trial, animals are placed directly on the platform at the end of the arm. On trial 2, they are placed with their front paws on the platform and allowed to climb onto it. On trial 3, they are placed halfway between the platform and the opposite end of the arm and allowed to swim to the platform. On trial 4, they are placed at the end of the arm opposite the platform. On trial 5, the barrier blocking the arm from the central arena is removed; animals are placed in the center of the arena and allowed to find the platform in the open arm. On trials 6 and 7, all barriers are removed and the animals are allowed to find a platform in any arm.

Testing: To examine reference memory, 4 of the arms remain "unplatformed" (do not contain a platform at the end of the arm) for the duration of testing. To examine working memory, 4 of the arms contain a platform, each of which is removed after a mouse finds it. The sequence of platformed and unplatformed arms varies from animal to animal but stays constant for each animal. Each session consists of 4 consecutively run trials. One of the unplatformed arms is designated the "start arm". Each animal is placed into the maze at the far end of this arm. It is then allowed to swim into the central arena and select an arm to enter. If the animal finds a platform within 120 seconds, then the trial is ended, the animal is allowed 15 seconds to remain on the platform, and then it is removed to a delay cage for a 30 second intertrial interval (animals are dried with a towel after removal from the water). If the animal does not find the platform within 60 seconds, then it is led to the nearest platform by the experimenter (it then receives the same treatment as an animal that has found the platform). During the intertrial interval, the platform vacated by the animal is removed from the maze. Trials 2-4 continue in the same way until each animal has located all 4 platforms. The animal is then returned to its home cage. Testing continues for 15 consecutive days.

Object recognition. The purpose of this task is to examine how well a rodent can remember the identity and location of objects (Fernandez et al., 2008; Fan et al., 2010; Boulware et al., 2013; Fortress et al., 2013b; Fortress et al., 2013a; Fortress et al., 2014; Fortress et al., 2015).

Apparatus: The apparatus is a wooden box, painted white (60 cm wide by 60 cm long by 47 cm high). The top of the box is open. Either one or two boxes are used at a time. The boxes are placed on a table in a room lit by four halogen lamps so that the lighting is fairly dim. Inside the box is placed 2 objects of varying shapes and textures. Each object is 6-7 cm wide and high. Data are recorded using a camera mounted on the ceiling connected to a computer outside of the room running custom written software. During habituation and testing, the door to the room is closed and the experimenter remains outside of the room. Prior to and during habituation, animals are handled and a small Lego Duplo block is placed in their cage for several days to habituate the mice to objects.

Procedure: The task lasts for 4 sessions. During sessions 1 and 2, each animal is habituated to the empty box by allowing them 5 minutes to roam around the box (during which time matrix crossings are recorded; see below). Between animals, the box is cleaned with 70% ethyl alcohol (EtOH). During session 3, each animal is placed in the box with two identical objects positioned near the corners of one side. The animal is allowed to freely investigate the objects. The trial ends when the animal has accumulated 30 seconds of total time investigating the objects (investigating involves behavior directed at the object). The animal is then placed in its home cage. For some experiments, an intraperitoneal drug injection or intracranial drug infusion will be given immediately after completion of the trial to examine drug effects on consolidation of memory. Between animals, the box is cleaned with 70% EtOH. During session 4, each animal is placed in the box with two objects, this time an object seen on day 1 (familiar) and a new object (novel). If the animal remembers the familiar object, then it should spend more time investigating the novel object (rodents have a natural affinity for new things). Again, the animals are allowed to investigate the objects until 30 seconds of total time has been accumulated investigating the objects. The animals are then placed back in their home cages. Between animals, the box is cleaned with 70% ethyl alcohol.

Object placement. The purpose of this task is to examine how well a rodent can remember the location of a particular object (Boulware et al., 2013). The apparatus and procedure is identical to object recognition except that during session 4, no new objects are introduced, but one of the familiar objects is moved to the opposite corner of the testing box.

Spatial/object novelty. This version of the object task tests both spatial and object recognition within the same extended test session (Ricceri et al., 2000; Frick and Gresack, 2003). Testing consists of 7 successive 6 min sessions, separated by 3 min delays during which the subjects are returned to their home-cage. Three objects are simultaneously presented in a square arena. During session 1, each animal is placed into the empty open field for habituation. During sessions 2-4, three objects are placed at the periphery of the arena and the amount of exploration of each is recorded. In session 5, the spatial configuration is changed by moving one object, thereby testing detection of spatial novelty. In session 6, the configuration of the objects remains unchanged. In the last session, one of the familiar objects is replaced by a new object at the same location, thereby testing detection of object novelty.

Matrix crossings. This task is used in conjunction with the object recognition tasks as a control to measure locomotor activity. Matrix crossings are recorded during the habituation trial for the object recognition task. One 5-minute session is conducted inside of the object recognition box. Each animal is placed in the box for 5 minutes. During this time, the number of times the animal crosses the lines in a grid superimposed on a computer image of the box are recorded. At the completion of the single trial, the animal is placed back in its home cage. In between animals, the container is cleaned with 70% ethyl alcohol (EtOH). Drugs or hormones are never administered in conjunction with this task.

Reflexes. Two basic reflexes are tested as a control for sensorimotor function (Frick et al., 2000). The righting reflex is tested by holding each animal by its tail and attempting to flip it on its back. A score of 1 indicates the presence of a righting reflex and a score of 0 means the mouse can be flipped over. The placing reflex is tested by holding each animal by its tail and lowering it towards a table. If the animal extends its forearms towards the table, a score of 1 is recorded. If not, a score of 0 is recorded.

Elevated plus maze. This task is a common method of measuring anxiety (Frick et al., 2000). It consists of a wooden maze with a central platform and four arms radiating out in a plus shape. Two opposite arms have walls and are painted black, whereas the other opposite arms do not have walls and are painted white. The maze is elevated 90 cm above the floor. One session is conducted in which each animal is placed in the central platform and allowed to freely explore the maze for 5 min. An experimenter located outside of the room will record where the animal spends its time. Testing is conducted in a quiet, dimly lit room. Drugs or hormones will be administered 30 min before testing.

Forced swim task. This classic model of depression will be used to test for depressive-like behavior (Mitchell and Meaney, 1991). Animals will be placed in a plexiglas cylinder (18 cm in diameter and 50 cm high) filled with water to a depth of 38 cm at a temperature of 22-23 degrees C. There is no way for the animals to escape; they must swim or float on the water. Testing will be conducted over the course of two days. On day 1, the animals are placed in the water for 15 min to introduce them to the water and apparatus. The animals are then dried using a heat lamp and returned to their home cage. On day 2, the animals are placed in the water for 6 min, and immobility (floating) time is recorded. The duration of immobility is defined as floating in without additional activity other than that necessary for the animal to keep its head above water. Water will be changed in the cylinder after every other animal is tested. Drugs or hormones will be administered 30 min prior to testing on day 2.

Contextual fear conditioning. This task is a standard method of measuring emotional memory. Fear conditioning and testing will take place in a standard operant chamber equipped with speaker module that is located in an acoustic isolation room. On day 1, animals will be placed in the chamber. After 3 min, animals will be presented with 3 co-terminating tone-footshock pairings (tone: 2.9 kHz, 82 dB, 15 sec; footshock: 1 mA, 1 sec) with 1 min intertrial intervals. The pain associated with this footshock feels like a quick pin-prick or a shock from static electricity. Animals will be removed 1 min after the termination of the last shock and returned to their home cages. On day 2, all animals will undergo a context fear retention test; subjects will be placed back into the trained context for 8 minutes in the absence of any tone or shock. On day 3, all animals will undergo a tone fear retention test in a novel context. The test will consist of a 1 min baseline period followed by 8 min of continuous tone. The tone and shock presentations will be controlled, and the freezing data collected, by an IBM-PC computer equipped with the Coulbourn LabLinc Habitest Universal Linc System. A 24-cell infrared activity monitor that detects movement of the animals' emitted infrared (1300 nm) body heat image in the x, y, and z axes will be used to assess freezing behavior.

Inhibitory avoidance. This is another task to measure emotional memory. Animals will be individually placed in the lit side of the two connected compartment chamber (a standard inhibitory avoidance apparatus). Once the animal enters the dark compartment (which is innately preferred), a single brief footshock (1 mA for 1 sec) will be administered. Afterwards, the animal will be placed back in the homecage. The next day the animal will be placed back in the lit side of the chamber. The latency to enter the dark compartment will be measured (in absence of footshock).

Example 12

Examination of HDAC Inhibitor Distribution in the Body

The extent of the HDACi distribution in the brain and perhaps other tissues of the body will be determined in vivo. Male and female mice will be injected with vehicle or HDAC inhibitor and tissues will be collected at various times afterwards. Tissue will be dissected and analyzed in various ways. Histone acetylation will be measured in tissue homogenates using Western blotting. Alternatively or in addition, matrix-assisted laser desorption/ionization imaging mass spectroscopy (MALDI-IMS) will be used to examine compound distribution in tissue slices from male and female mice. For this procedure, ultrathin sections will be cut and mounted onto MALDI glass slides, which will then be vacuum dessicated and stored at −80° C. until analysis by MALDI-IMS. MALDI matrix deposition and MALDI-IMS analysis will be conducted using the Shimadzu CHIP-1000 chemical ink-jet printer and Axima MALDI-IMS system.

The invention claimed is:

1. A compound according to Formula (I):

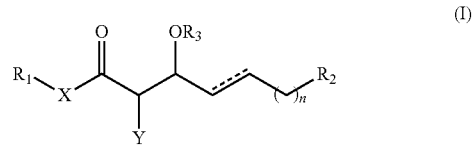

or a stereoisomer or salt thereof;
wherein X is NH or O or a direct bond;
$R_1$ is H, $C_{1-10}$ alkyl, aryl, heteroaryl, or —NH—CHR$_a$C(O)—OR$_4$;
$R_a$ is an amino acid side chain, H, $C_{1-10}$ alkyl, $C_{1-10}$ heteroalkyl, aryl, or heteroaryl;
$R_4$ is H, $C_{1-10}$ alkyl, heteroaryl or aryl;

R₂ is SH, SeH, or C(O)NHOH, or the compound forms a disulfide or diselenide dimer at the R₂ position;

R₃ is H, C$_{1-10}$ alkyl, heteroaryl, aryl, or —C(O)R₅;

R₅ is C$_{1-10}$ alkyl, heteroaryl, aryl, or —CH(N(R$_N$)₂)(CR'R"OR$_O$);

R' is H or C$_{1-10}$ alkyl, heteroaryl, or aryl;

R" is H or C$_{1-10}$ alkyl, heteroaryl, or aryl;

each R$_N$ is independently H, C$_{1-10}$ alkyl, heteroaryl, or aryl;

R$_O$ is H, C$_{1-10}$ alkyl, heteroaryl, or aryl;

Y is H, C$_{1-10}$ alkyl, heteroaryl, aryl, or halogen;

n is an integer from 0 to 5;

wherein if X is a direct bond, then R₁ is —NH—CHR$_a$C(O)—OR₄; and wherein the dashed bond indicates the presence of an optional double bond.

2. The compound according to claim 1 selected from the group consisting of

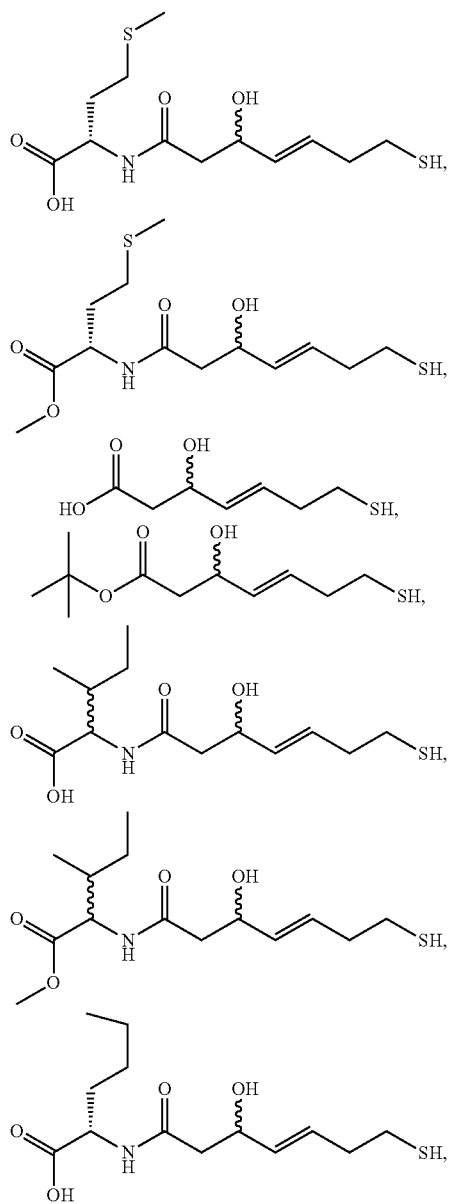

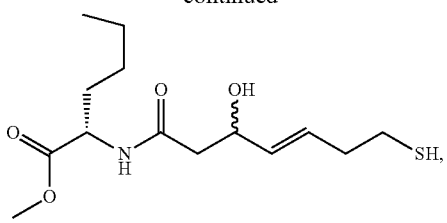

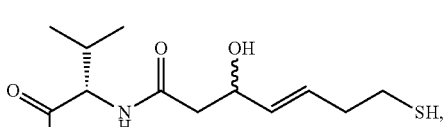

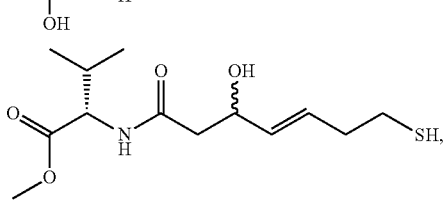

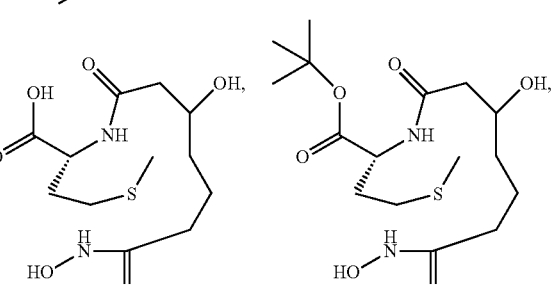

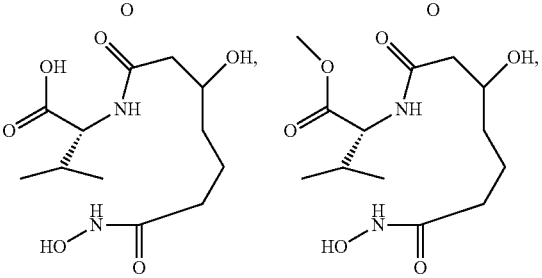

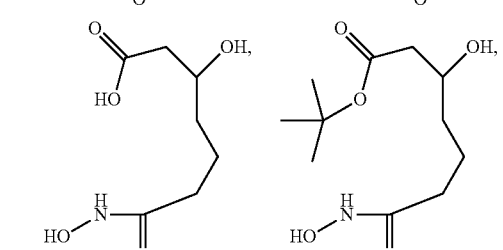

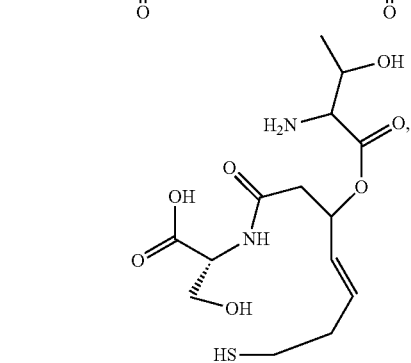

-continued

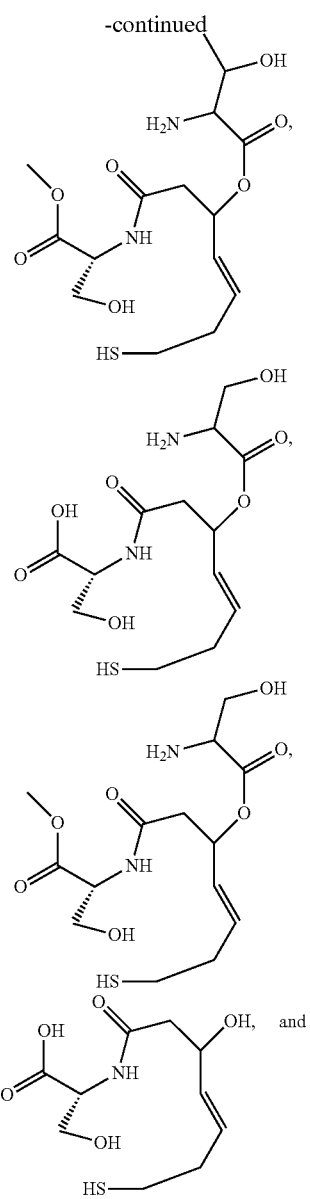

-continued

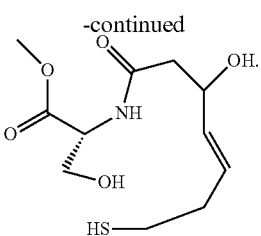

or a stereoisomer or salt thereof.

3. The compound according to claim 1, or a stereoisomer or salt thereof, wherein X is a direct bond and $R_1$ is —NH—$CHR_a$C(O)—$OR_4$.

4. The compound according to claim 3, or a stereoisomer or salt thereof, wherein $R_2$ is SH or C(O)NHOH.

5. The compound according to claim 3, or a stereoisomer or salt thereof, wherein Y is H and $R_3$ is H or —C(O)$R_5$.

6. The compound according to claim 1, or a stereoisomer or salt thereof, wherein X is O and $R_1$ is H, $C_{1-10}$ alkyl, aryl, or heteroaryl.

7. The compound according to claim 6, or a stereoisomer or salt thereof, wherein $R_2$ is SH or C(O)NHOH.

8. The compound according to claim 6, or a stereoisomer or salt thereof, wherein Y is H and $R_3$ is H or —C(O)$R_5$.

9. The compound according to claim 6, or a salt or stereoisomer thereof, wherein the optional double bond is present.

10. The compound according to claim 6, or a stereoisomer or salt thereof, wherein $R_2$ is SH.

11. The compound according to claim 6, or a stereoisomer or salt thereof, wherein Y is H and $R_3$ is H.

12. The compound according to claim 6, or a stereoisomer or salt thereof, wherein $R_1$ is $C_{1-10}$ alkyl.

13. The compound according to claim 6, or a stereoisomer or salt thereof, wherein $R_1$ is $C_{1-4}$ alkyl.

14. The compound according to claim 13, or a stereoisomer or salt thereof, wherein $R_2$ is SH and n is 2.

15. The compound according to claim 14, or a stereoisomer or salt thereof, wherein Y is H and $R_3$ is H.

16. The compound according to claim 15, or a salt or stereoisomer thereof, wherein the optional double bond is present.

* * * * *